US010722696B2

(12) United States Patent
Goodall et al.

(10) Patent No.: US 10,722,696 B2
(45) Date of Patent: Jul. 28, 2020

(54) NANO-SCALE COATINGS AND RELATED METHODS SUITABLE FOR IN-VIVO USE

(71) Applicant: NANOMEDICAL SYSTEMS, INC., Austin, TX (US)

(72) Inventors: Randy Goodall, Austin, TX (US); Sharath Hosali, Austin, TX (US)

(73) Assignee: NANOMEDICAL SYSTEMS, INC., Austin, TX (US)

( * ) Notice: Subject to any disclaimer, the term of this patent is extended or adjusted under 35 U.S.C. 154(b) by 223 days.

(21) Appl. No.: 15/352,691

(22) Filed: Nov. 16, 2016

(65) Prior Publication Data

US 2017/0189658 A1    Jul. 6, 2017

Related U.S. Application Data

(63) Continuation of application No. 13/111,368, filed on May 19, 2011, now abandoned.

(60) Provisional application No. 61/346,372, filed on May 19, 2010.

(51) Int. Cl.
| | | |
|---|---|---|
| *A61M 31/00* | (2006.01) | |
| *B82Y 5/00* | (2011.01) | |
| *A61L 27/30* | (2006.01) | |
| *B01L 3/00* | (2006.01) | |

(52) U.S. Cl.
CPC ......... *A61M 31/002* (2013.01); *A61L 27/306* (2013.01); *B82Y 5/00* (2013.01); *A61L 2300/608* (2013.01); *A61L 2400/12* (2013.01); *A61M 2205/025* (2013.01); *A61M 2205/0238* (2013.01); *A61M 2205/04* (2013.01); *A61M 2207/00* (2013.01); *B01L 3/502707* (2013.01)

(58) Field of Classification Search
CPC .... A61M 2205/0238; A61M 2205/025; A61M 2205/04; A61M 2207/00; A61M 31/002
See application file for complete search history.

(56) References Cited

U.S. PATENT DOCUMENTS

| | | | |
|---|---|---|---|
| 3,731,681 | A | 5/1973 | Blackshear et al. |
| 4,834,704 | A | 5/1989 | Reinicke |
| 4,955,861 | A | 9/1990 | Enegren et al. |
| 5,651,900 | A | 7/1997 | Keller et al. |
| 5,728,396 | A | 3/1998 | Peery et al. |
| 5,769,823 | A | 6/1998 | Otto |
| 5,770,076 | A | 6/1998 | Chu et al. |
| 5,798,042 | A | 8/1998 | Chu et al. |

(Continued)

FOREIGN PATENT DOCUMENTS

| | | |
|---|---|---|
| DE | 10 2006 014476 | 7/2007 |
| EP | 1 977 775 | 10/2008 |

(Continued)

OTHER PUBLICATIONS

"The Economic Costs of Drug Abuse in the United States," www.whitehousedrugpolicy.gov, Sep. 2001.

(Continued)

*Primary Examiner* — Imani N Hayman
(74) *Attorney, Agent, or Firm* — Parker Highlander PLLC

(57) ABSTRACT

A nano-scale device and method of manufacturing and use. The nano-scale device may be used in-vivo and may comprise a fluid path with an inlet microchannel, an outlet microchannel, and a nanochannel. The fluid path comprises a bio-robust material. In certain embodiments, the bio-robust material may be coated over a material that is not bio-robust.

6 Claims, 57 Drawing Sheets

(56) References Cited

U.S. PATENT DOCUMENTS

| | | | |
|---|---|---|---|
| 5,893,974 | A | 4/1999 | Keller et al. |
| 5,938,923 | A | 8/1999 | Tu et al. |
| 5,948,164 | A | 9/1999 | Iida et al. |
| 5,985,328 | A | 11/1999 | Chu et al. |
| 6,044,981 | A | 4/2000 | Chu et al. |
| 6,592,519 | B1 | 7/2003 | Martinez |
| 7,025,871 | B2 | 4/2006 | Broadley et al. |
| 7,326,561 | B2 | 2/2008 | Goodman et al. |
| 7,413,846 | B2 | 8/2008 | Maloney et al. |
| 2002/0087120 | A1 | 1/2002 | Rogers et al. |
| 2002/0156462 | A1 | 10/2002 | Stultz |
| 2003/0010638 | A1 | 1/2003 | Hansford et al. |
| 2003/0064095 | A1 | 4/2003 | Martin et al. |
| 2004/0038260 | A1 | 2/2004 | Martin et al. |
| 2004/0082908 | A1 | 4/2004 | Whitehurst et al. |
| 2004/0116905 | A1 | 6/2004 | Pedersen et al. |
| 2004/0262159 | A1 | 12/2004 | Martin et al. |
| 2005/0118229 | A1 | 6/2005 | Boiarski |
| 2006/0001039 | A1 | 1/2006 | Zamanian |
| 2006/0180469 | A1 | 8/2006 | Han et al. |
| 2006/0191831 | A1 | 8/2006 | Hansford et al. |
| 2006/0204738 | A1 | 9/2006 | Dubrow et al. |
| 2007/0066138 | A1 | 3/2007 | Ferrari et al. |
| 2007/0077273 | A1 | 4/2007 | Martin et al. |
| 2010/0152699 | A1 | 6/2010 | Ferrari et al. |
| 2011/0137596 | A1 | 6/2011 | Grattoni et al. |

FOREIGN PATENT DOCUMENTS

| | | |
|---|---|---|
| WO | WO 2000/74751 | 12/2000 |
| WO | WO 2006/113860 | 10/2006 |
| WO | WO 2007/047539 | 4/2007 |
| WO | WO 2007/089483 | 8/2007 |
| WO | WO 2008/019886 | 9/2008 |
| WO | WO 2008/109886 | 9/2008 |
| WO | WO 2009/149362 | 12/2009 |
| WO | WO 2010/056986 | 5/2010 |
| WO | WO 2010/120817 | 10/2010 |

OTHER PUBLICATIONS

"Under the Counter: The Diversion and Abuse of Controlled Prescription Drugs in the US," *The National Center on Addiction and Substance Abuse (CASA) at Columbia University*, New York, NY, CASA, Jul. 2005.

Christensen et al., "Tantalum oxide thin films as protective coatings for sensors," *J. Micromech. Microeng.*, 9:113-118, 1999.

Extended European Search Report issued in European application No. 11784219.5, dated Jul. 8, 2014.

Extended European Search Report issued in European Patent Application No. 10765046, dated Oct. 1, 2012.

Fine et al., "A robust nanofluidic membrane with tunable zero-order release for implantable dose specific drug delivery," *Lab on a Chip*, 10(2): 3074-3083, 2010.

Hammerle et al., "Biostability of micro-photodiode arrays for subretinal implantation," *Biomaterials*, 23:797-804, 2002.

Hess et al., "PECVD silicon carbide as a thin film packaging material for microfabricated neural electrodes," *Mater. Res. Soc. Symp. Proc.*, 1009-U04-03, 2007.

International Search Report and Written Opinion issued in PCT/US2011/037094, dated Jan. 13, 2012.

Narayan et al., "Mechanical and biological properties of nanoporous carbon membranes," *Biomed. Mater.*, 3:034107, 2008.

Nath et al., "Buprenorphine pharmacokinetics: relative bioavailability of sublingual tablet and liquid formulations," *J. Clin. Pharmacol.*, 39:619-623, 1999.

Nurdin et al., "Haemocompatibility evaluation of DLC-and SIC-coated surfaces," *Eur Cells Mat.*, 5: 17-28, 2003.

Office Communication issued in U.S. Appl. No. 13/111,368, dated May 21, 2014.

Office Communication issued in U.S. Appl. No. 13/111,368, dated Oct. 7, 2014.

Office Communication issued in U.S. Appl. No. 13/111,368, dated Apr. 21, 2015.

Office Communication issued in U.S. Appl. No. 13/111,368, dated Jul. 6, 2015.

Office Communication issued in U.S. Appl. No. 13/111,368, dated Aug. 10, 2015.

Office Communication issued in U.S. Appl. No. 13/111,368, dated May 17, 2016.

Report: Stakeholder Workshop on a National Buprenorphine Program, Health Canada, Nov. 18, 2004.

Samhsa, "Overview of Findings from the 2002 National Survey on Drug Use and Health," Rockville, MD, DHHS publication, SMA 03-3774, published 2003.

Samhsa, "Results from the 2003 National Survey on Drug Use and Health: National Findings," Rockville, MD, DHHS publication, SMA 04-3964, published 2004.

Samhsa, "The DAWN Report: oxycodaone, hydrocodone, and polydrug use," 2002. Jul. 2004 http://oas.samhsa.gov/2k4/oxycodone/oxycodone.cfm.

Schmitt et al., "Passivation and corrosion of microelctrode arrays," *Electrochimica Acta*, 44:3865-3883, 1999.

Voskerician et al., "Biocompatibility and biofouling of MEMS drug delivery devices," *Biomaterials*, 24:1959-1967, 2003.

Yakimova et al., "Surface functionalization and biomedical applications based on SiC," *J Physics D*, 40: 6435- 6442, 2007.

Zorman et al., "Silicon carbide as a material for biomedical Microsystems," *DIT*, Apr. 1-3, 2009.

Office Communication issued in European Patent Application No. 11784219.5, dated Jun. 18, 2018.

Filatova, Ekaterina A., et al. "Investigating routes toward atomic layer deposition of silicon carbide: Ab initio screening of potential silicon and carbon precursors." *Journal of Vacuum Science & Technology A*, vol. 35, Issue 1. 01B103 (2016); https://doi.org/10.1116/1.4964890.

NANO-SCALE COATINGS AND RELATED METHODS SUITABLE FOR IN-VIVO USE

CROSS-REFERENCE TO RELATED APPLICATIONS

This application is a continuation of co-pending U.S. patent application Ser. No. 13/111,368, filed May 19, 2011, which claims priority to U.S. Provisional Patent Application Ser. No. 61/346,372, filed May 19, 2010. The entire contents of each of the above-referenced disclosures are incorporated herein by reference.

BACKGROUND INFORMATION

Considerable advances have been made in the field of therapeutic agent (e.g. drug) delivery technology over the last three decades, resulting in many breakthroughs in clinical medicine. The creation of therapeutic agent delivery devices that are capable of delivering therapeutic agents in controlled ways is still a challenge. One of the major requirements for an implantable drug delivery device is controlled release of therapeutic agents, ranging from small drug molecules to larger biological molecules. It is particularly desirable to achieve a continuous passive drug release profile consistent with zero order kinetics whereby the concentration of drug in the bloodstream remains constant throughout an extended delivery period.

These devices have the potential to improve therapeutic efficacy, diminish potentially life-threatening side effects, improve patient compliance, minimize the intervention of healthcare personnel, reduce the duration of hospital stays, and decrease the diversion of regulated drugs to abusive uses.

A nano-scale device may be used in drug delivery products for the effective administration of drugs. In particular embodiments, the nano-scale device may be a nanochannel delivery device (NDD). In addition, nanochannel delivery devices can be used in other applications where controlled release of a substance over time is needed. Further, an NDD may be used as a filter within a fluidic pathway. In many embodiments a nano-scale device may have dimensional, structural, surface, or other properties required for proper function that must remain stable against micrometer or nanometer range modification for extended durations, e.g., months or even years.

In certain embodiments, a nano-scale device (including, e.g. an NDD) may be part of an apparatus that is implanted into a human or animal body, for example, to provide a therapeutic agent. In certain embodiments, the nano-scale device may be used to provide a controlled release of the therapeutic agent from the implanted apparatus. Both the therapeutic agent and the body, however, contain fluids and chemical compounds that may attack over time certain materials used in the construction of an nano-scale device, which can affect the structural stability of the nano-scale device and/or the ability of the nano-scale device to control the release of the therapeutic agent. The materials in the nano-scale device "fluid path" (e.g., the path that a therapeutic molecule travels passing through the nano-scale device) and any and all other surfaces of the nano-scale device that might be exposed to bodily fluids, therapeutic agents, or other potentially deleterious environmental factors, should therefore be resistant to any and all degradation in form and function from those fluids, agents, and factors.

SUMMARY

In the following, the term "nano-scale device" comprises a device that includes features or aspects with dimensions that are less than 1 μm.

The term "nanochannel delivery device" (or "NDD") as used herein comprises, but is not limited to, any of the exemplary nanochannel devices disclosed in U.S. patent application Ser. No. 12/618,233 (the "'233 application") filed Nov. 13, 2009 and entitled "Nanochanneled Device and Related Methods" and International Patent Application Number PCT/US10/30937 (the "'937 Application") filed Apr. 13, 2010 and entitled "Nanochanneled Device and Method of Use", both of which are incorporated herein by reference.

The term "bio-fluid" as used herein comprises bodily fluid of any kind and location within a human or animal body, as well as equivalent fluid with similar properties that may be a functional, testing, or diagnostic environment for a nano-scale device, and any therapeutic or other proximate agents in fluid or solid form. The term "bio-robust" as used herein comprises materials configured to withstand bio-fluids at mammalian body temperature (e.g., approximately 37 degrees Celsius) or elevated temperatures for extended periods of time.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The term "inlet microchannel" is defined as a microchannel providing direct fluid communication between an internal nanochannel and the entry side of a nanochanneled delivery device.

The term "outlet microchannel" is defined as a microchannel providing direct fluid communication between an internal nanochannel and the exit side of a nanochanneled delivery device.

The term "nanochannel" is defined as a channel with a cross-section having at least one dimension (e.g. height, width, diameter, etc.) that is less than 200 nm.

The term "macrochannel" is defined as a channel with a cross-section having a maximum dimension (e.g. height, width, diameter, etc.) that is greater than about 10 μm.

As used herein, the term "direct fluid communication" is interpreted as fluid communication between two bodies that are directly connected, e.g. such that fluid may exit one body and immediately enter the second body without flowing through an intermediate body. For example, in the embodiment shown in FIGS. 3A-3G of the '233 and '937 Applications, outlet 70 is in direct fluid communication with nanochannel 25. However, outlet 70 is not in direct fluid communication with inlet 30, because fluid must flow through an intermediate body (nanochannel 25) after exiting inlet 30 and before entering outlet 70.

Furthermore, as used herein, the term "inlet" is interpreted as a chamber or reservoir within a nanochannel delivery device that initially retains a substance being delivered via the nanochannel delivery device. Similarly, an "outlet" is interpreted as a chamber or reservoir within a nanochannel delivery device that retains a substance immediately prior to the substance exiting the nanochannel delivery device.

Certain embodiments comprise a nanochannel delivery device comprising: an inlet microchannel; an outlet microchannel; and a nanochannel in fluid communication with the inlet microchannel and the outlet microchannel, wherein the inlet microchannel comprises a non-bio-robust material coated with a bio-robust material. In particular embodiments, the bio-robust material comprises tantalum oxide. In certain embodiments, the bio-robust material comprises silicon carbide.

In specific embodiments, the non-bio-robust material comprises silicon nitride. In particular embodiments, the non-bio-robust material comprises silicon. In certain embodiments, the nanochannel is in direct fluid communication with the inlet microchannel and the outlet microchannel.

Particular embodiments may comprise a macrochannel in fluid communication with the inlet microchannel, where the macrochannel comprises a non-bio robust material coated with a bio-robust material.

Certain embodiments may comprise: a multi-layered structure comprising an inlet surface and an outlet surface; and a fluid path extending from the inlet surface to the outlet surface, where the fluid path includes an inlet microchannel, a nanochannel, and an outlet microchannel, wherein a first portion of the fluid path comprises a bio-robust material coating over a non-bio-robust material. In certain embodiments, the first portion of the fluid path comprises the inlet microchannel.

Particular embodiments may comprise a method of fabricating a nanochannel delivery device, where the method comprises forming a nanochannel delivery device comprising an inlet microchannel, an outlet microchannel, and a nanochannel, where the nanochannel is in fluid communication with the inlet microchannel and the outlet microchannel, and where the nanochannel, the inlet microchannel and the outlet microchannel form a fluid path through the nanochannel delivery device. The method may also comprise coating a first portion and the second portion of the fluid path with a bio-robust material. In certain embodiments, the first portion of the fluid path coated with a bio-robust material comprises the inlet microchannel. In certain embodiments, the second portion of the fluid path coated with a bio-robust material comprises the nanochannel. In particular embodiments, the bio-robust material coating of the first portion comprises tantalum oxide. In certain embodiments, the bio-robust material can be used to coat silicon. In particular embodiments, the bio-robust material can be used to coat polysilicon. In certain embodiments, the second portion of the fluid path coated with a bio-robust material comprises the outlet microchannel. In specific embodiments, the bio-robust material can be used to coat silicon oxide. In particular embodiments, the bio-robust material can be used to coat silicon nitride or polysilicon.

Certain embodiments comprise a method of providing dimensional stability to a nano-scale device, where the method comprises forming the nano-scale device with a first material that is not bio-robust, and coating the first material with a second material that is bio-robust. In particular embodiments, the nano-scale device comprises a nanochannel delivery device.

Specific embodiments may also comprise a method of forming a microchannel or a macrochannel, where the method comprises: etching a microchannel or a macrochannel in a non-bio-robust material, and coating the microchannel or a macrochannel with a bio-robust material.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
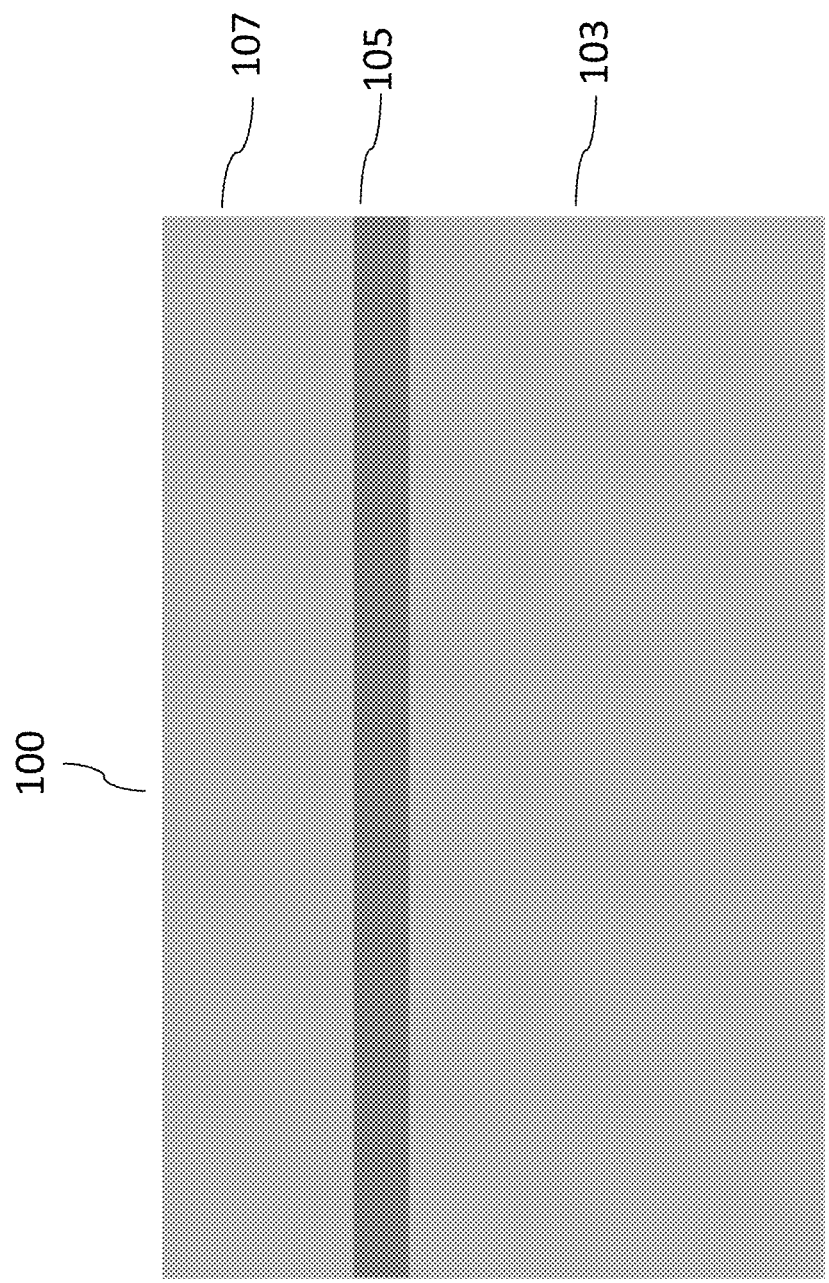
FIGS. 1-57 are schematic views of manufacturing processes according to exemplary embodiments.

As previously mentioned, in certain applications a nanochannel delivery device may be implanted into a human or animal body. It is therefore desirable that the materials exposed to bio-fluids be resistant to attack from those fluids. In certain applications, materials used in the construction of an NDD may not be resistant to bio-fluids.

For example, bio-fluids may cause corrosion or erosion of silicon, silicon dioxide and silicon nitride. The NDD embodiments disclosed in the '233 and '937 Applications incorporate silicon nitride and silicon as the "ceiling" and "floor" of the nanochannels. While silicon nitride provides good tensile strength, it does not generally exhibit good corrosion/erosion resistance in certain applications in the human body (11,12)

Therefore, it can be desirable to provide a coating of material that is "bio-robust" over a material that provides beneficial mechanical strength. As used herein, bio-robust materials include materials configured to withstand bio-fluids at body temperature (e.g., approximately 37 degrees Celsius) or elevated temperatures for extended periods of time. In specific embodiments, bio-robust materials maintain nanometer scale dimensions within 10 percent of their original dimensions over 1,000 days when exposed body fluids or equivalent at body temperature. These materials may include, for example, silicon carbide (SiC), tantalum oxide ($Ta_2O_5$), and other materials. Such materials may be deposited by chemical vapor deposition (CVD), atomic layer deposition (ALD), sputtering or by spin-on deposition, or a combination of these methods. In the exemplary embodiment described below, tantalum oxide is used to provide a bio-robust material in the inlet microchannels, while silicon carbide or Tantalum oxide/silicon carbide bilayer is used to provide a bio-robust material in other areas of the NDD that could be exposed to bio-fluids.

Embodiments of the present disclosure do not require that the structural material of the NDD be both bio-robust and structurally adequate. Instead, materials that are not bio-robust, but structurally sound (e.g., possessing the required tensile, compressive, and/or shear strengths) can be coated or covered with bio-robust materials. The bio-protection of this structural material (with the weak bio-robustness) comes from the application of a second layer which is used as a lining, whose primary purpose is to provide bio-robustness. This lining layer material can then have a relaxed requirement of structural adequacy. This allows for use of a material with limited strength/stress but adequate bio-robustness with a material with limited bio-robustness, but with adequate strength/stress.

Exemplary embodiments use a sacrificial channel material that can be selectively removed after the full device fabrication to create a nanochannel. Any material that can be wet-etched with a high selectivity with respect to other materials in the system can be used as the nanochannel material. The exemplary embodiment described below is based on Protocol 3 ("Monolithically-Fabricated Capping Layer") disclosed in the '233 and '937 Applications.

Figure 2:
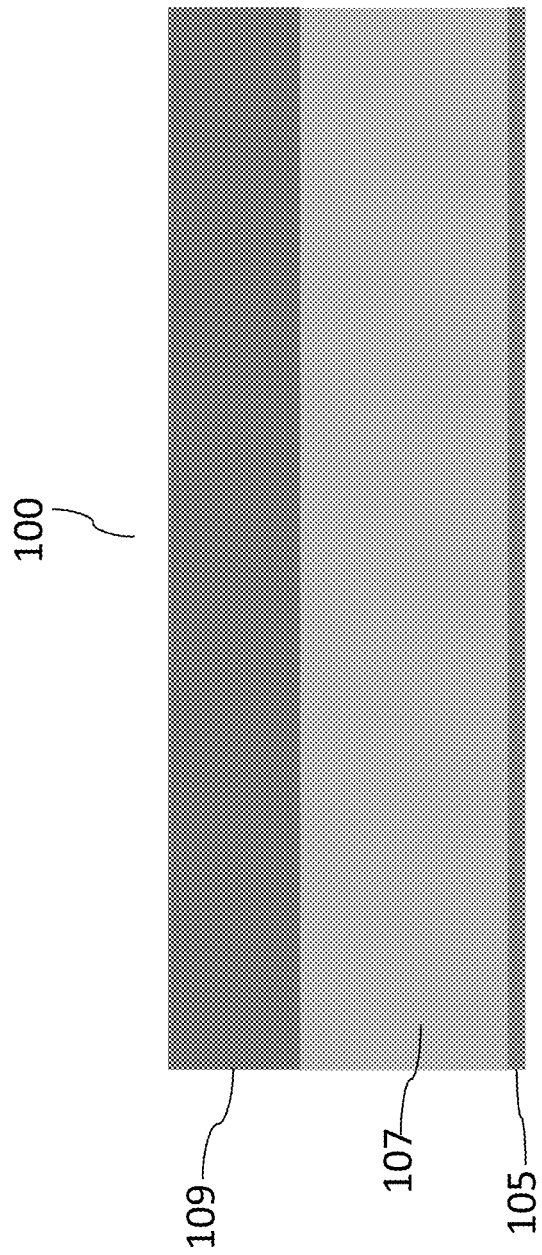
Figure 3:
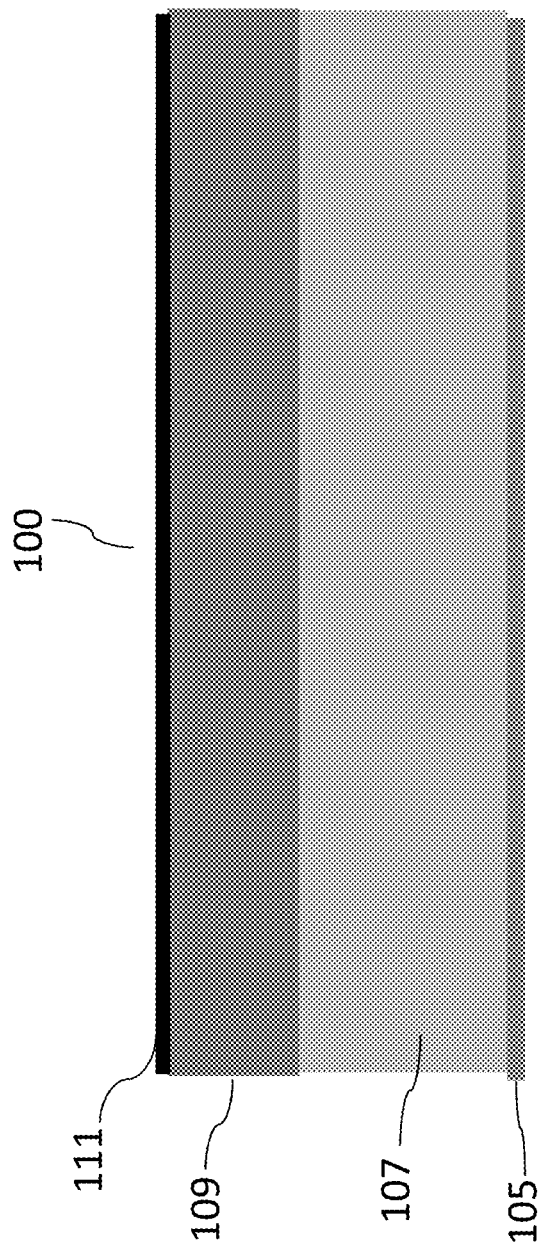

Referring initially to FIG. 1, a side section view of a silicon-on-insulator (SOI) wafer 100 comprises a lower silicon layer 103, an oxide layer 105 and an upper silicon layer 107. FIG. 2 illustrates a detailed view of a top portion of upper silicon layer 107 after a layer 109 of relatively thick bio-robust material has been deposited. In this exemplary embodiment, layer 109 comprises approximately 500 nm of silicon carbide deposited on upper silicon layer 107. As explained in more detail below, layer 109 serves as an etch landing material. Referring now to FIG. 3, a layer 111 of nanochannel material can be deposited on layer 109 to the desired thickness to form the nanochannel. In this embodiment, layer 111 comprises a layer of tungsten approximately 3 nm thick. Optionally, an additional bio-robust material can be laid under this sacrificial layer 111.

Figure 4:
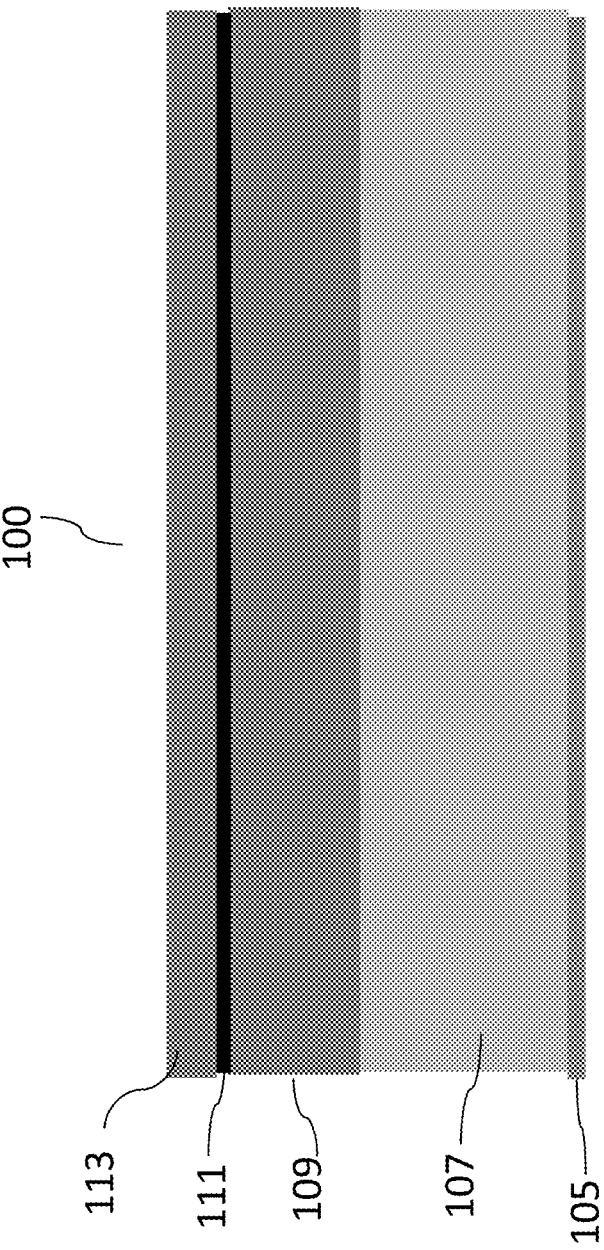
Figure 5:
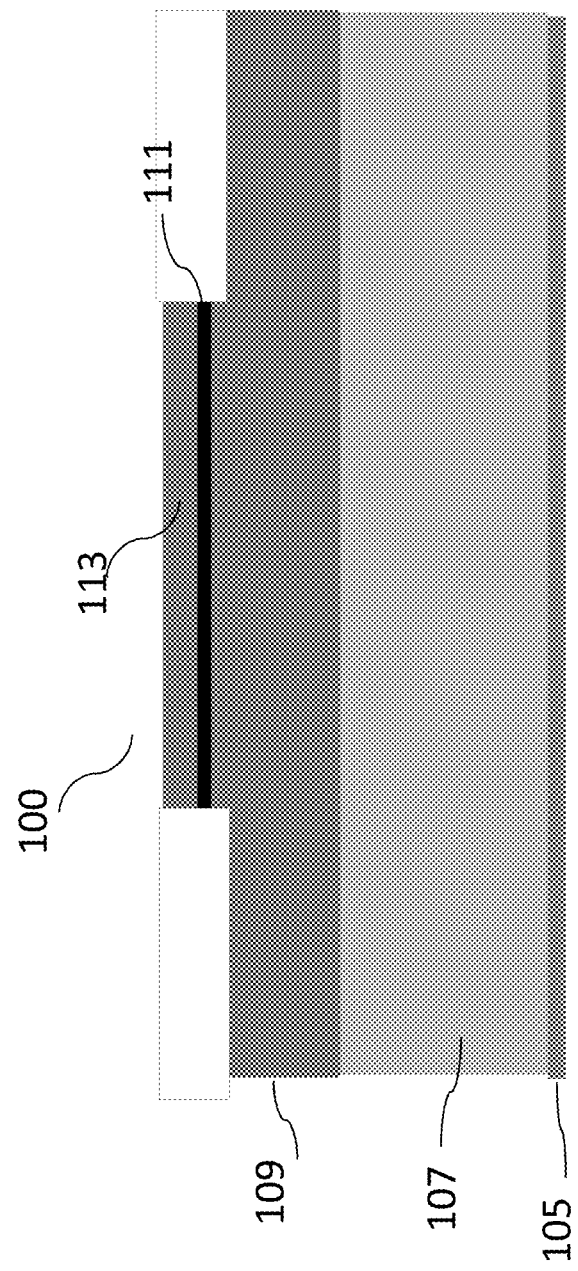
Figure 6:
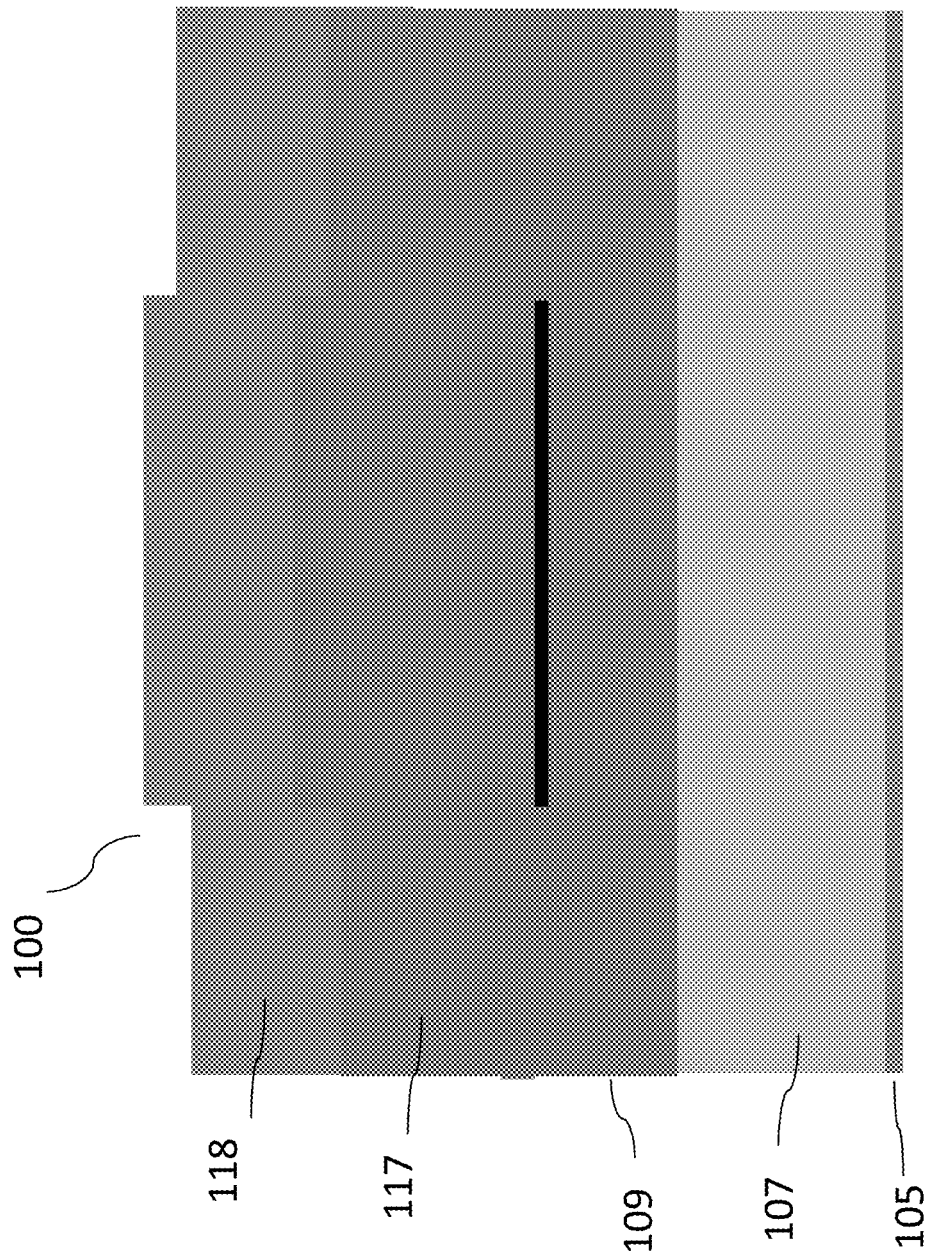
Figure 7:
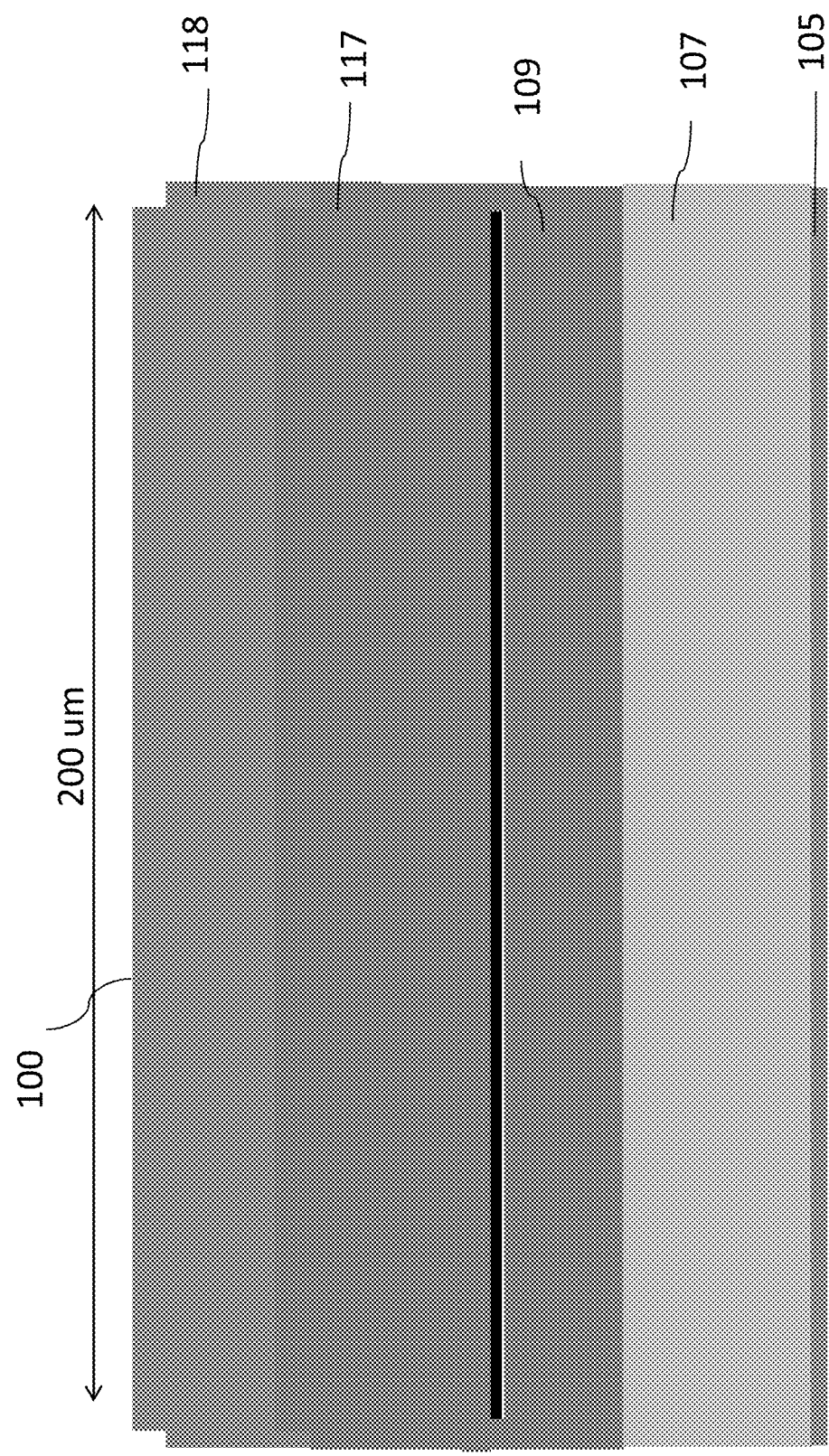

Referring now to FIG. 4, a layer 113 of relatively thin bio-robust material can be deposited on layer 111. In this embodiment, layer 113 comprises a layer of silicon carbide approximately 30 nm thick, and acts as a line protect layer. Optionally, an additional bio-robust material can be laid under this material, and over the sacrificial layer 111. As shown in FIG. 5, a mask pattern can be applied and layers 111 and 113 etched and then cleaned. Referring now to FIG. 6, a relatively thick layer 117 of bio-robust material may be deposited as a chemical-mechanical planarization (CMP) stop. In certain embodiments, layer 117 may comprise silicon carbide. An additional layer 118 that can be used as a sacrificial hardmask, such as silicon oxide is deposited. FIG. 7, shows the same stack of components as FIG. 6, but oriented perpendicular from the view shown in FIG. 6.

Figure 8:
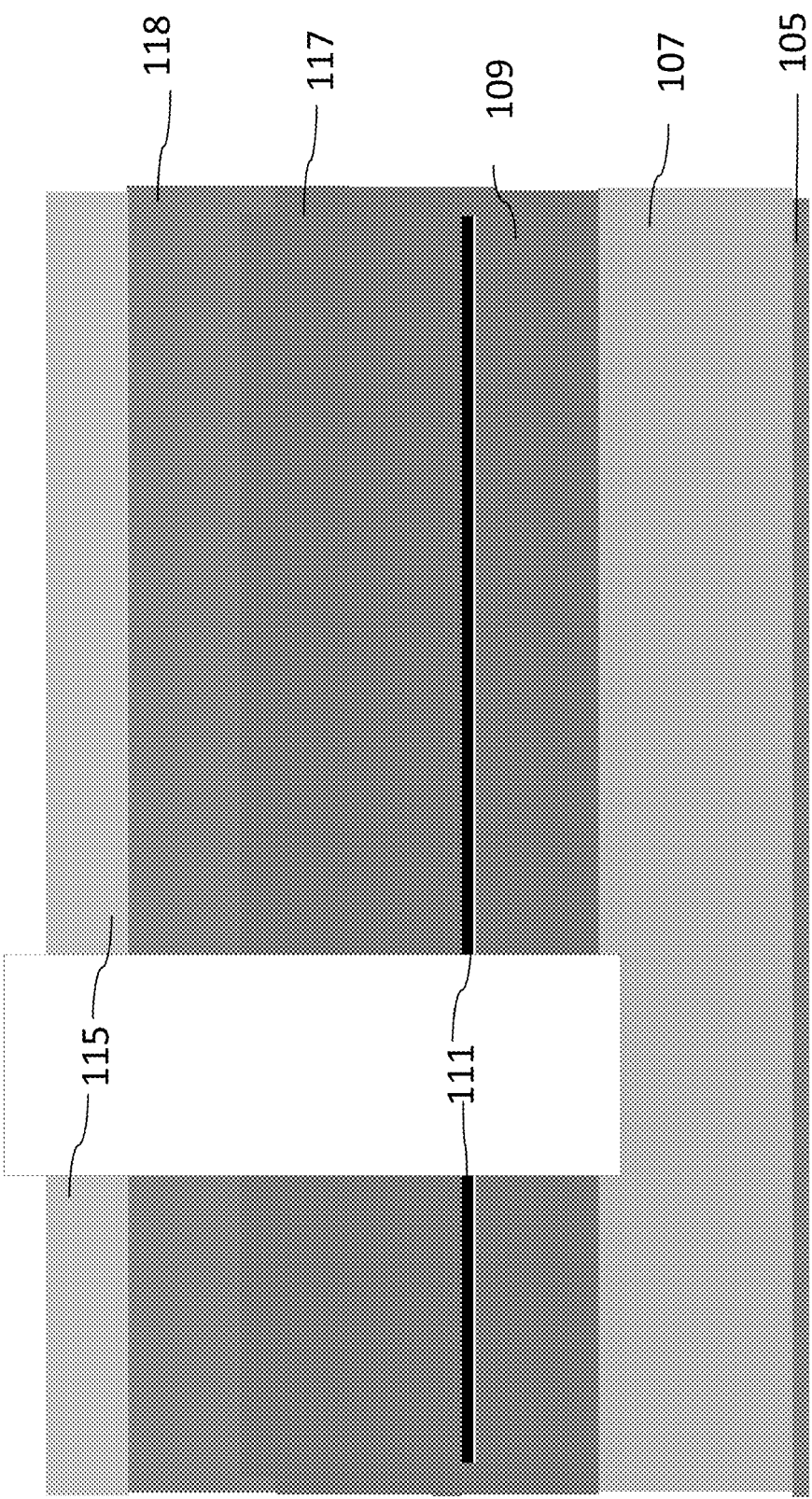
Figure 9:
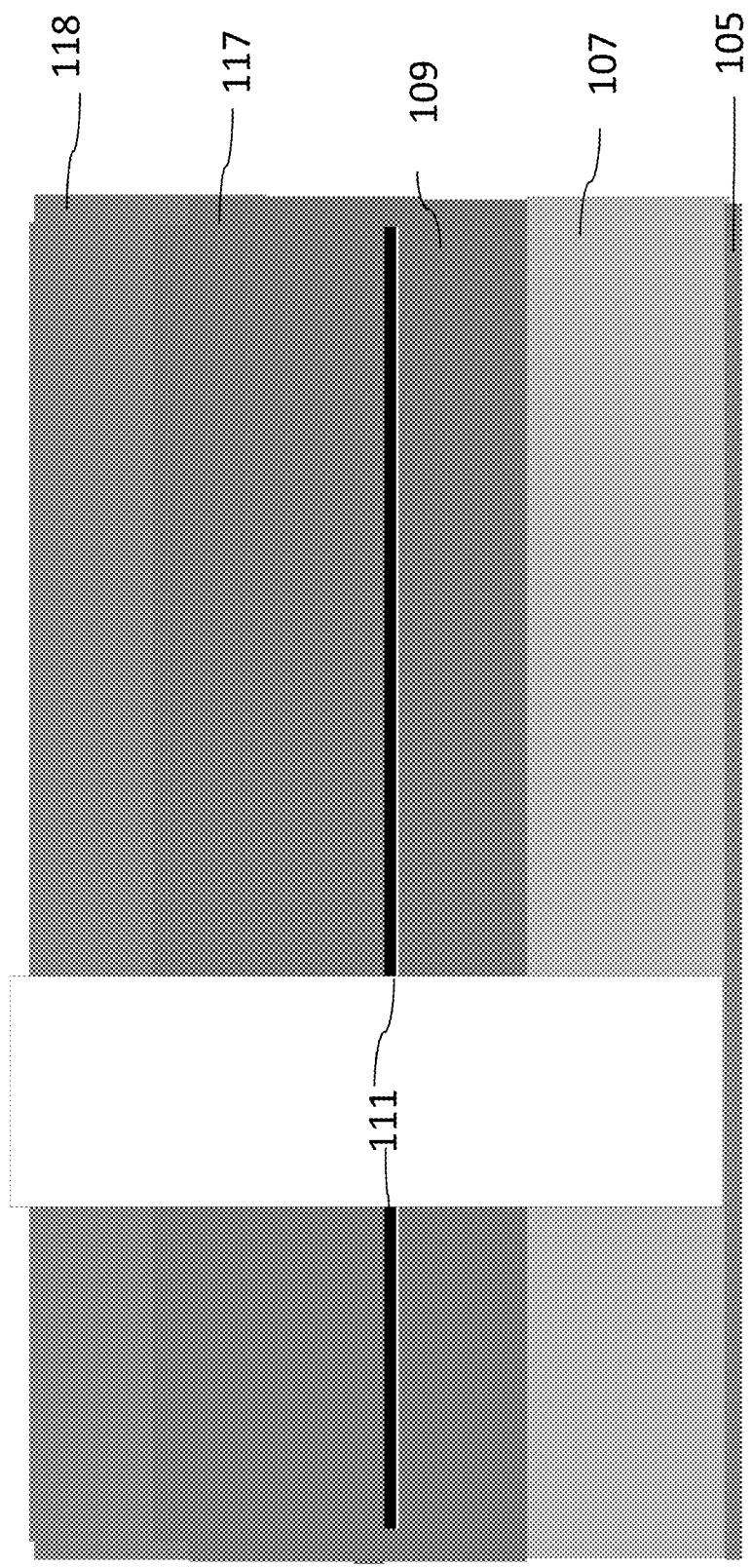
Figure 10:
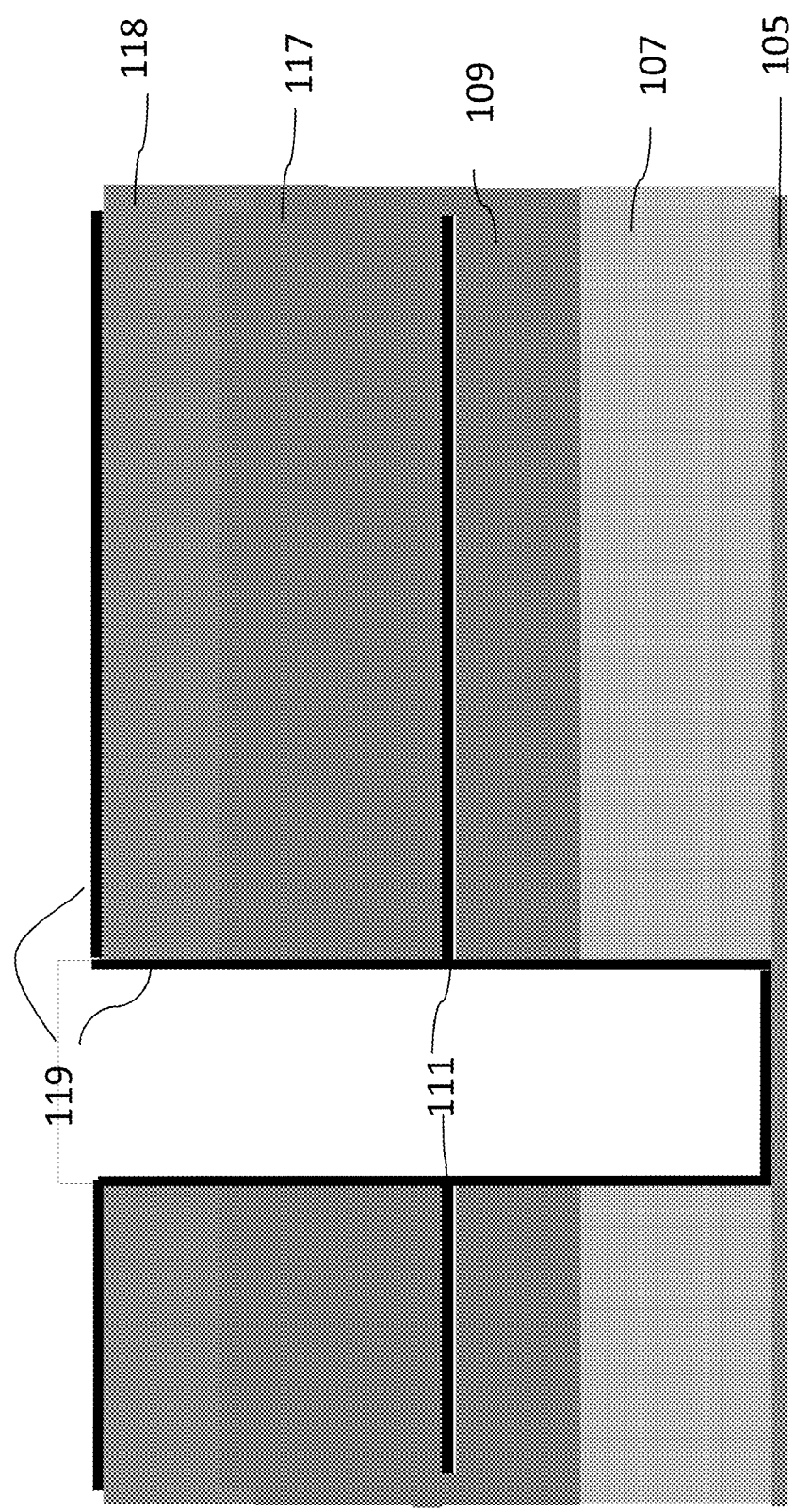

As shown in FIG. 8, the inlet microchannels can be formed by patterning with mask layer 115 and etching through the multiple deposited layers to silicon layer 107. As shown in FIG. 9, this etch is continued to stop at the oxide layer 105 and the wafer is cleaned. As shown in FIG. 10, a bio-robust layer 119 may be deposited on the wafer surface in order to coat the underlying silicon layer 107. In certain embodiments, bio-robust layer 119 may comprise ALD deposited material such as $Ta_2O_5$ since extreme conformality with the ability to cover a very high aspect ratio channel is desired.

Figure 11:
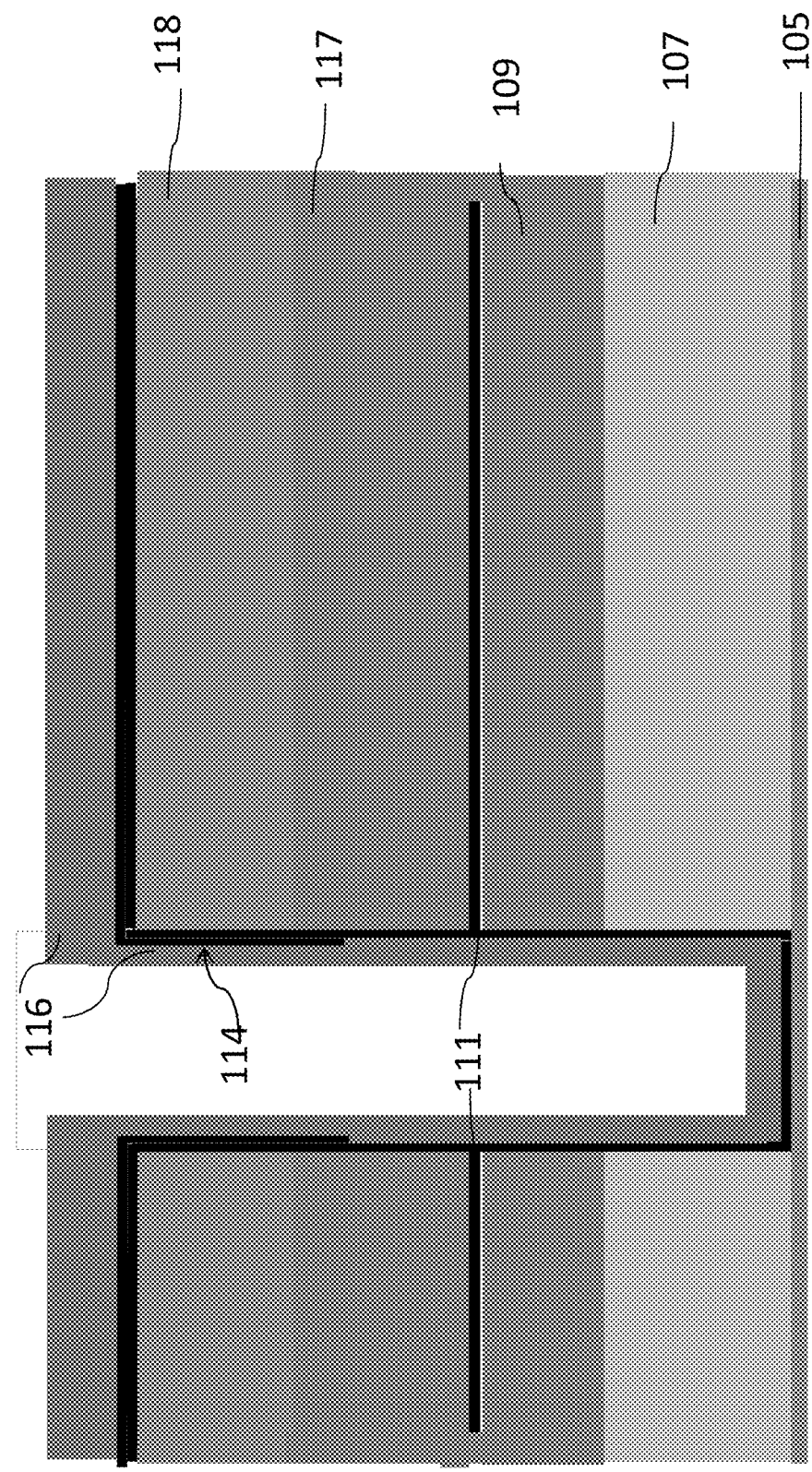

If the bio-robust material is incapable of resisting further process materials or conditions, additional sacrificial layers 114 and 116 can be deposited as shown in FIG. 11. Optionally, these materials can be TiN as layer 114 and ozone tetraethyl orthosilicate precursor deposited by a CVD technique, as layer 116, which deposits as a liner layer protecting the layer 119.

Figure 12:
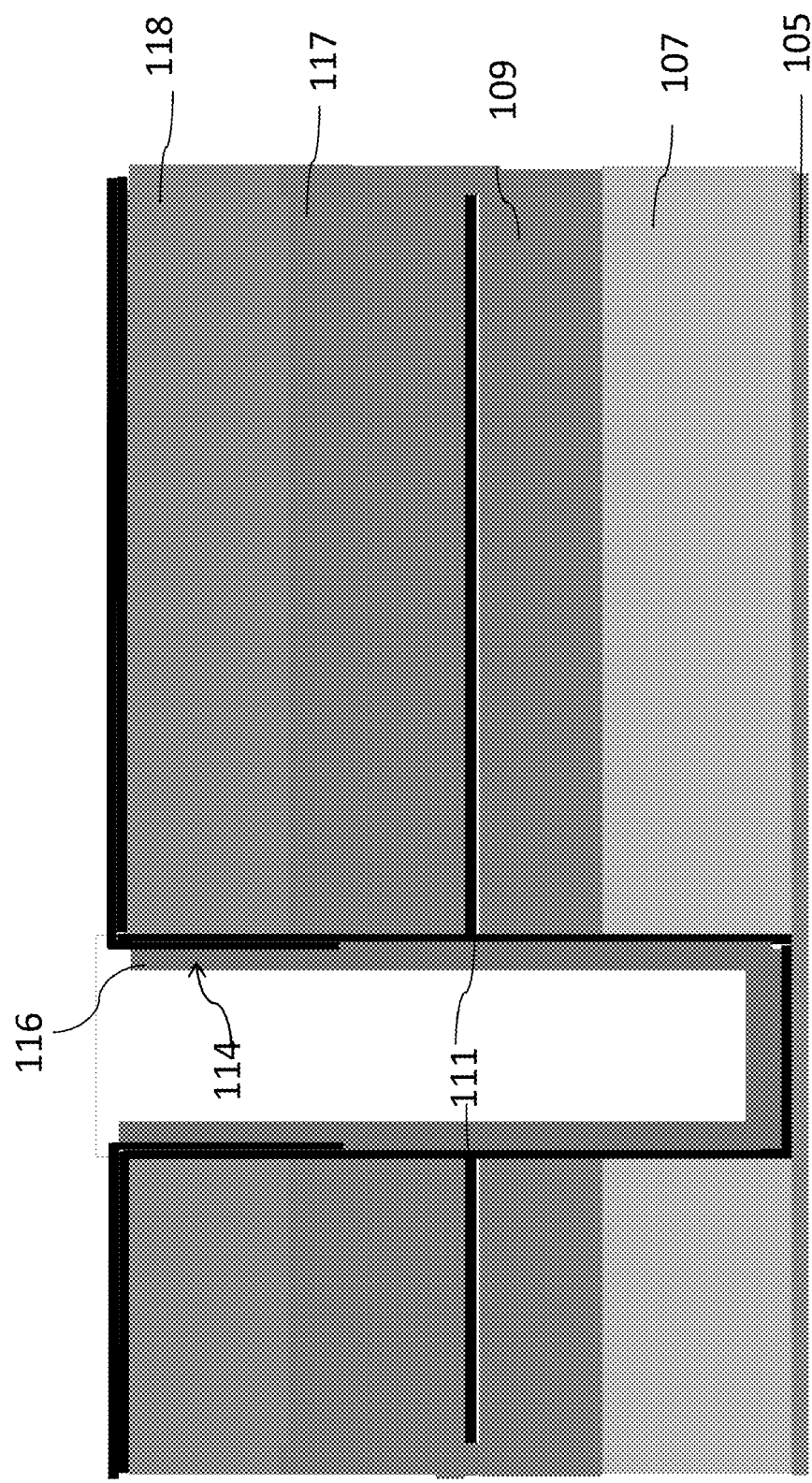

As shown in FIG. 12, the excess oxide above the layer 114 is etched away using a dry plasma process, with the etch stopping on liner layer 114, while retaining the protection of layer 119 in the sidewalls of the inlet.

Figure 13:
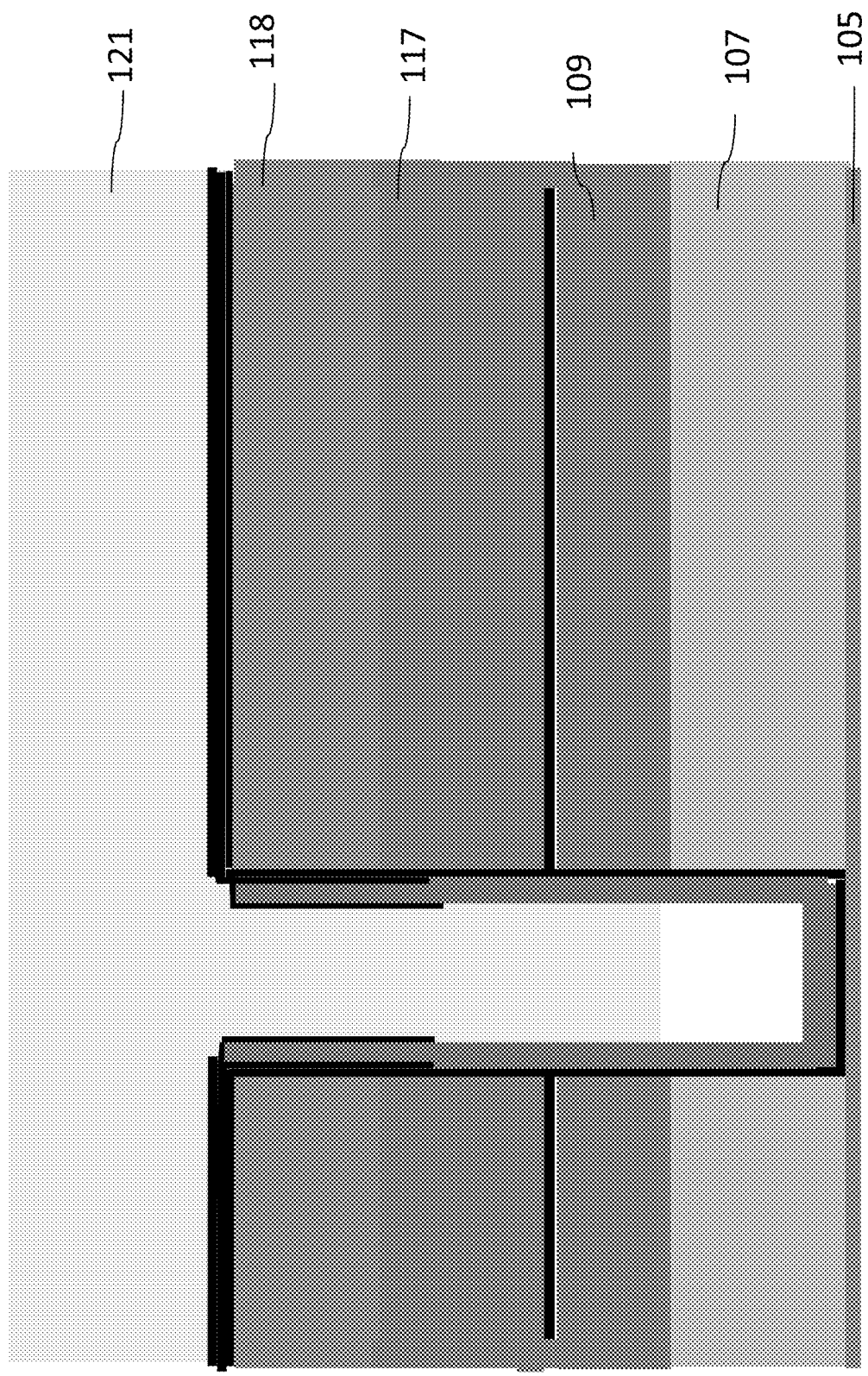

The structure may then be filled with a material 121 with a high conformality, as shown in FIG. 13. In certain embodiments, material 121 may comprise silicon dioxide deposited by the ozone tetraethyl orthosilicate precursor through a CVD technique. In other embodiments, material 121 may comprise tungsten with a Titanium nitride or a Titanium/Titanium Nitride liner.

Figure 14:
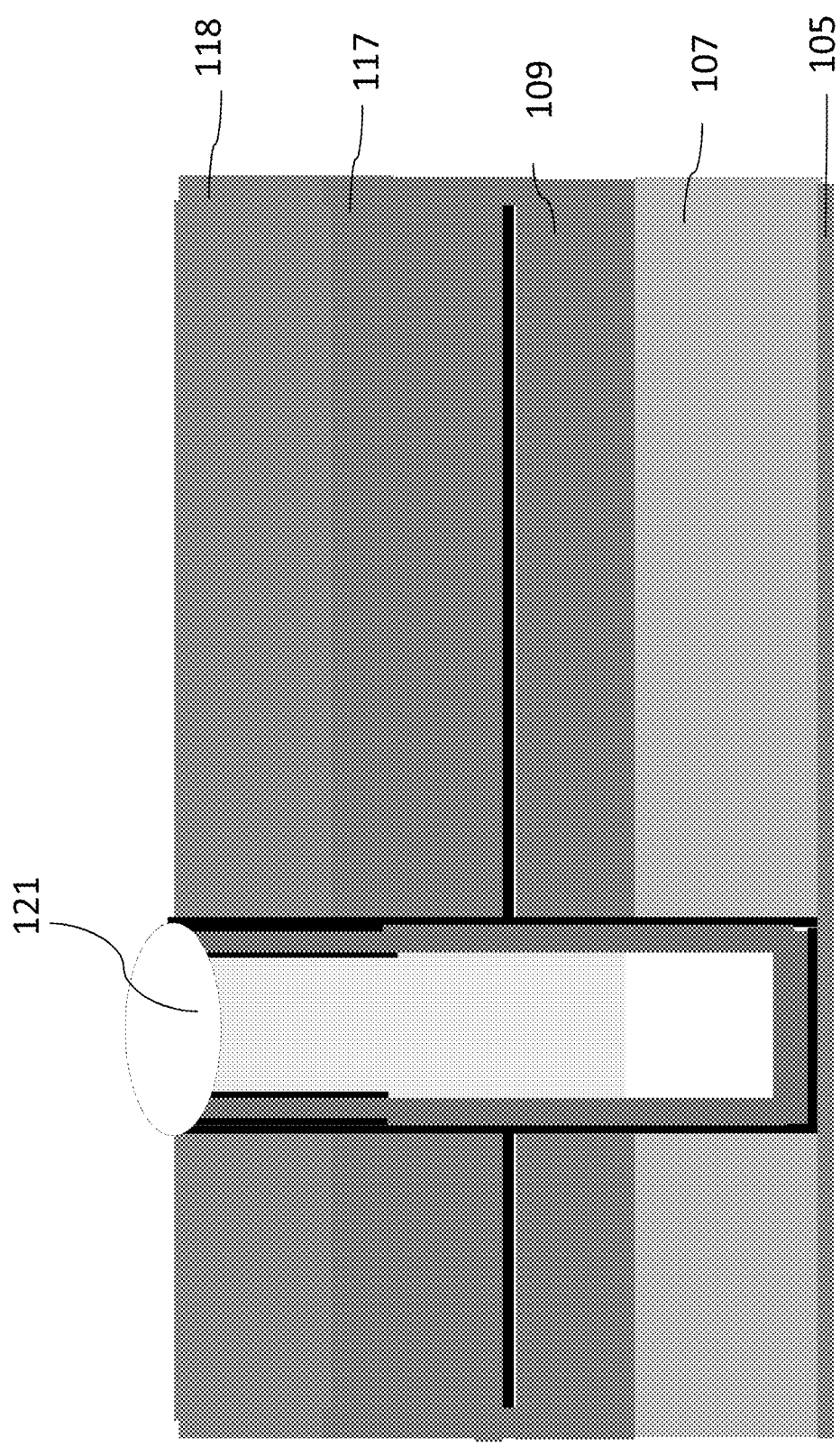

As shown in FIG. 14, the entire overburden above the layer 118 is removed by chemical mechanical planarization (CMP)

Figure 15:
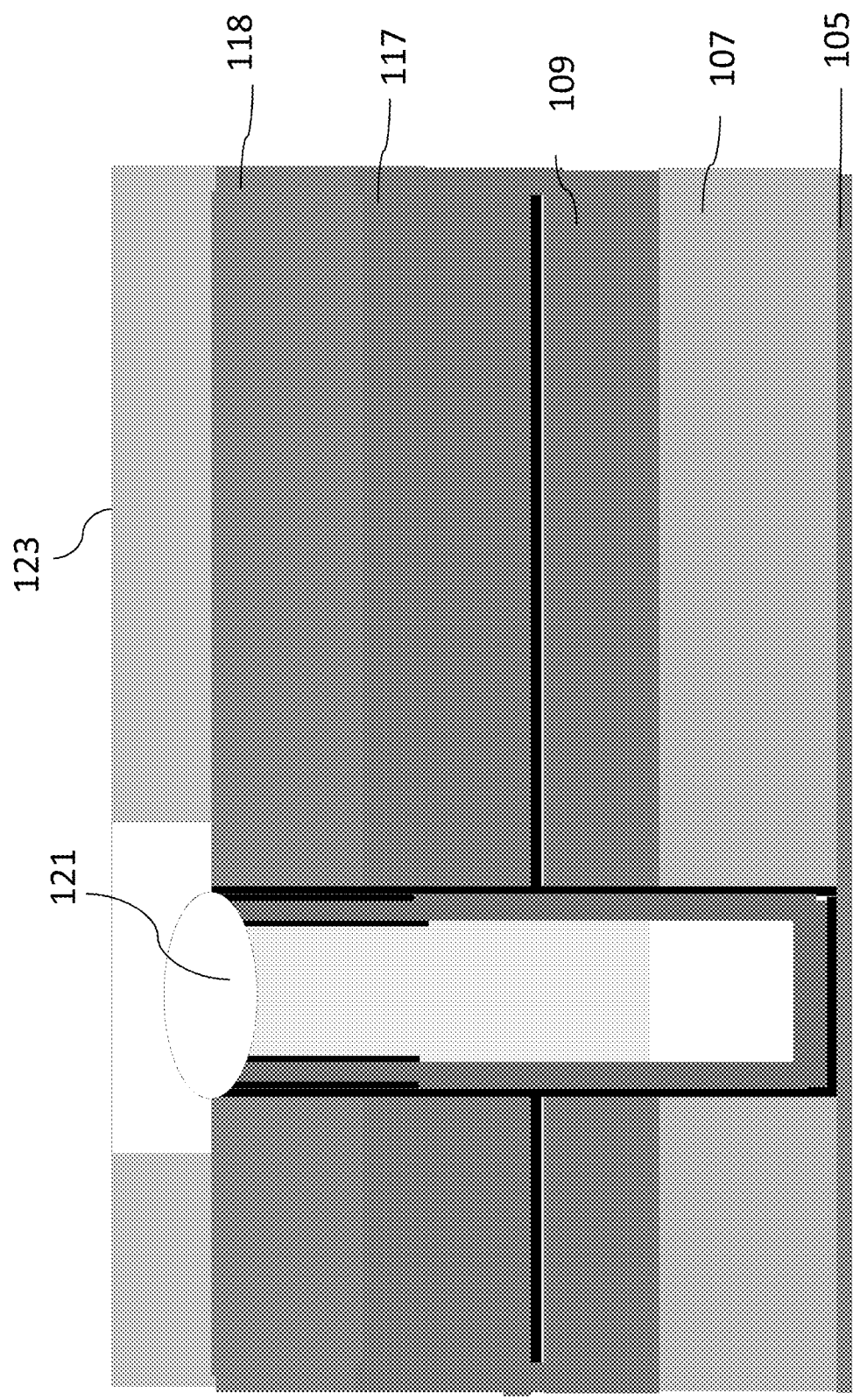
Figure 16:
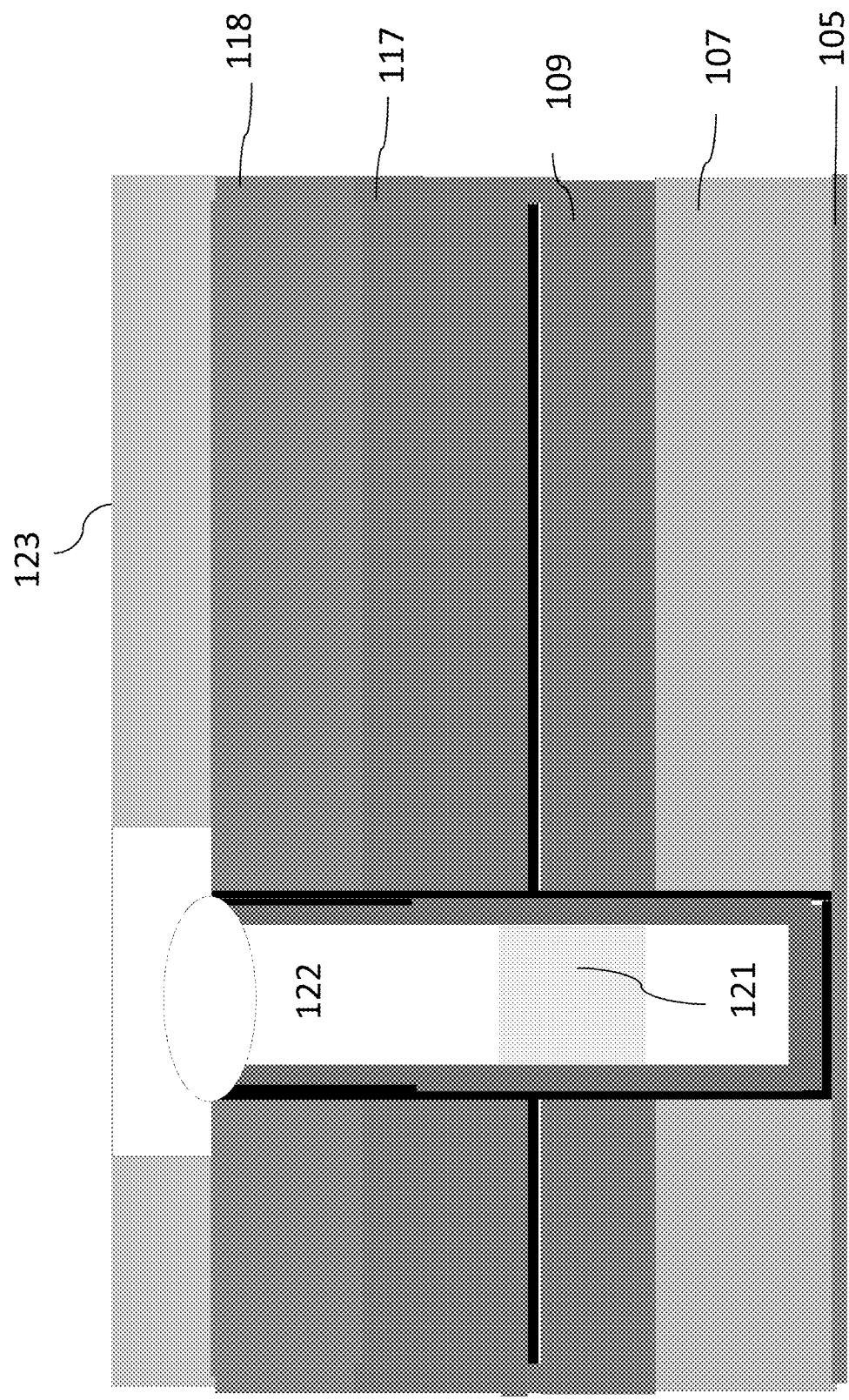
Figure 17:
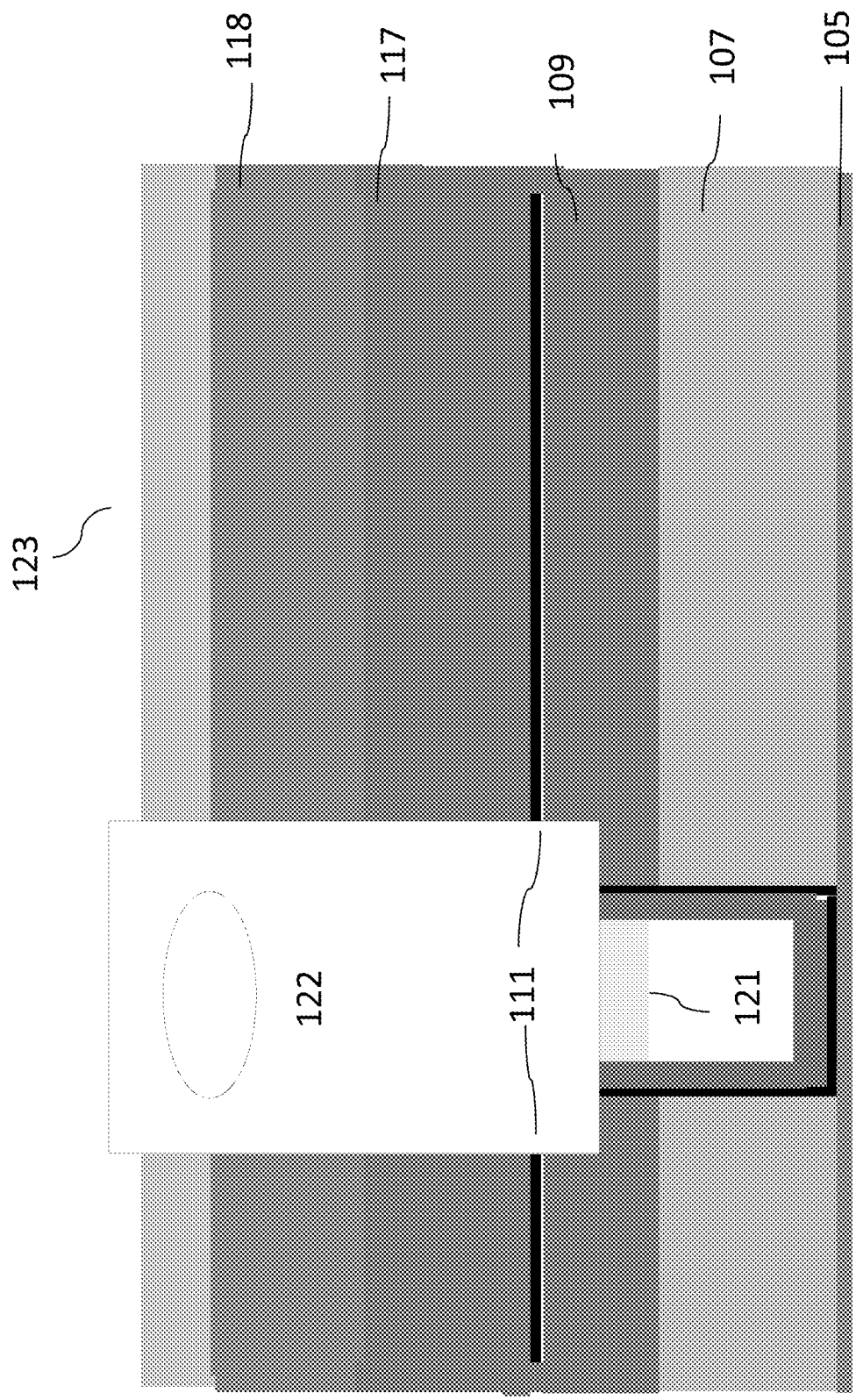
Figure 18:
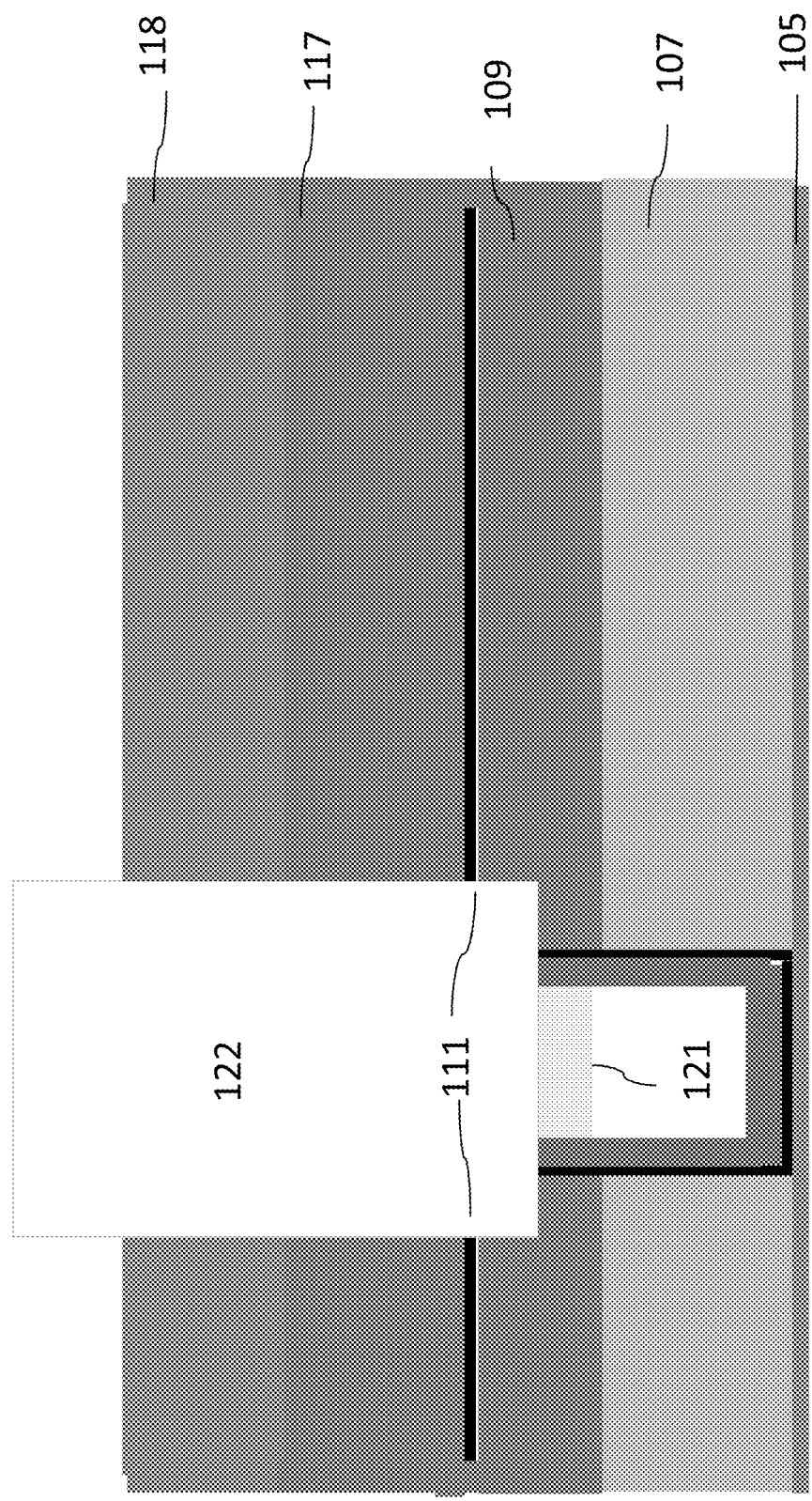
Figure 19:
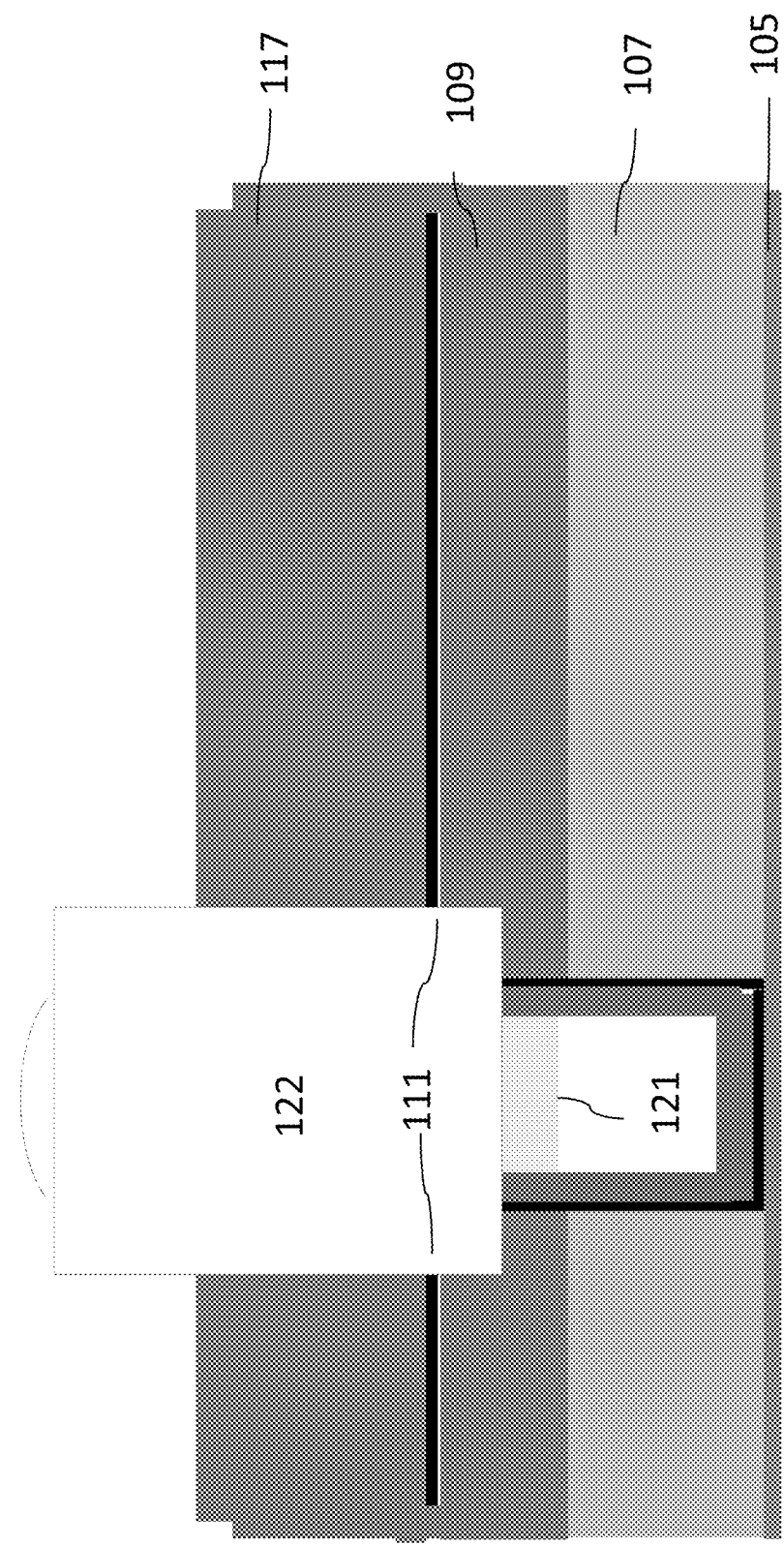

Referring now to FIG. 15 another mask 123 which is slightly larger than mask pattern 115 is patterned in resist. As shown in FIG. 16, material 121 in the vias is selectively etched with respect to material 118 by a plasma process. This is followed by another selective etch of layers 118, 117 and 111, stopping on the etch stop layer 109, as shown in FIG. 17. The etching depth can be controlled by adjusting the length of time of the etching process. In the embodiment shown, the etching stops in layer 109, below layer 111 (which is used to form the nanochannel) so that the nanochannel sidewalls are exposed. This creates inlet channels 122. Optionally, steps 16 and 17 can be combined into a single step by choosing an etch chemistry with appropriate selectivity. The remaining resist 123 can then be removed and the structure cleaned, as shown in FIG. 18. This is followed by removal of hardmask layer 118, as shown in FIG. 19.

Figure 20:
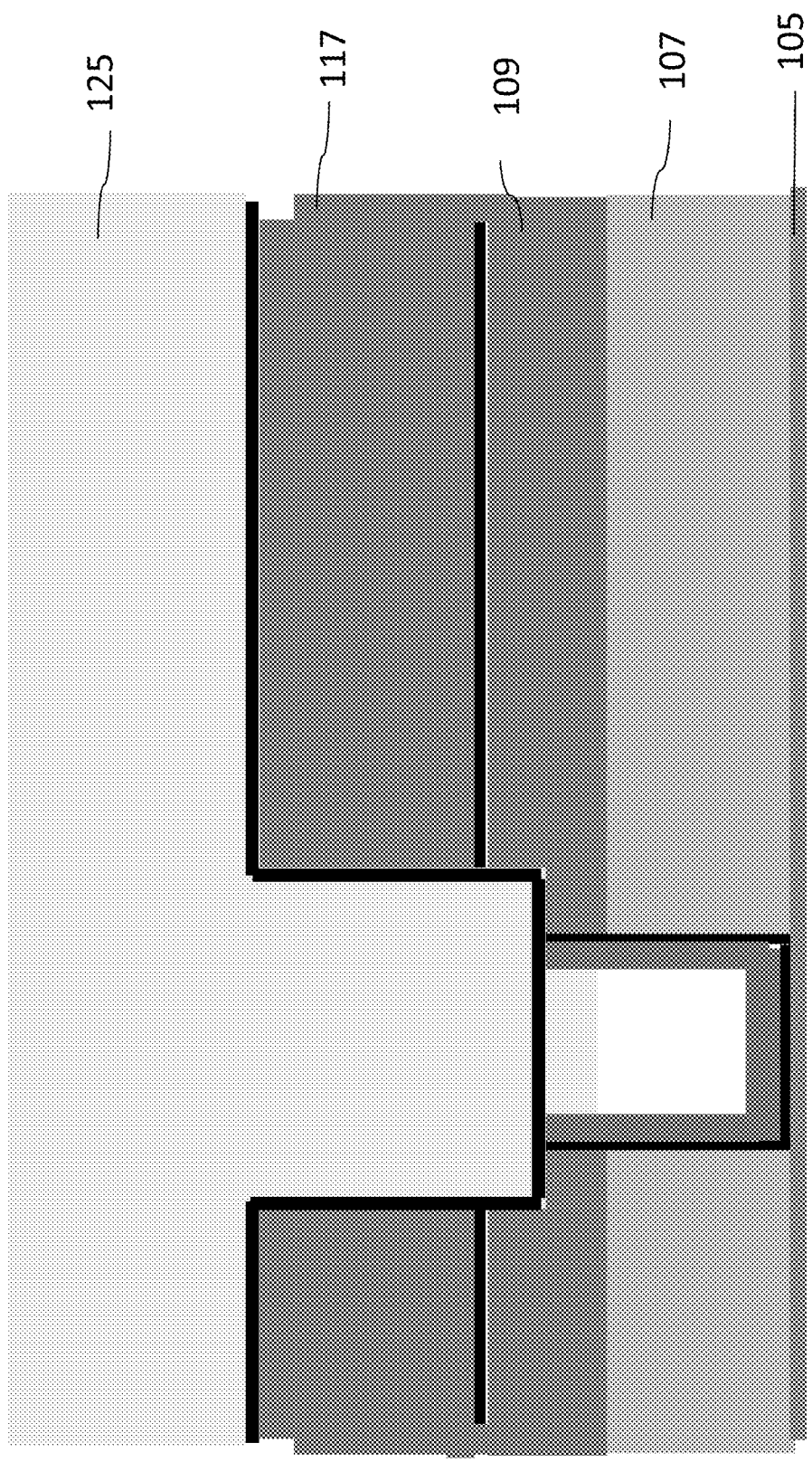
Figure 21:
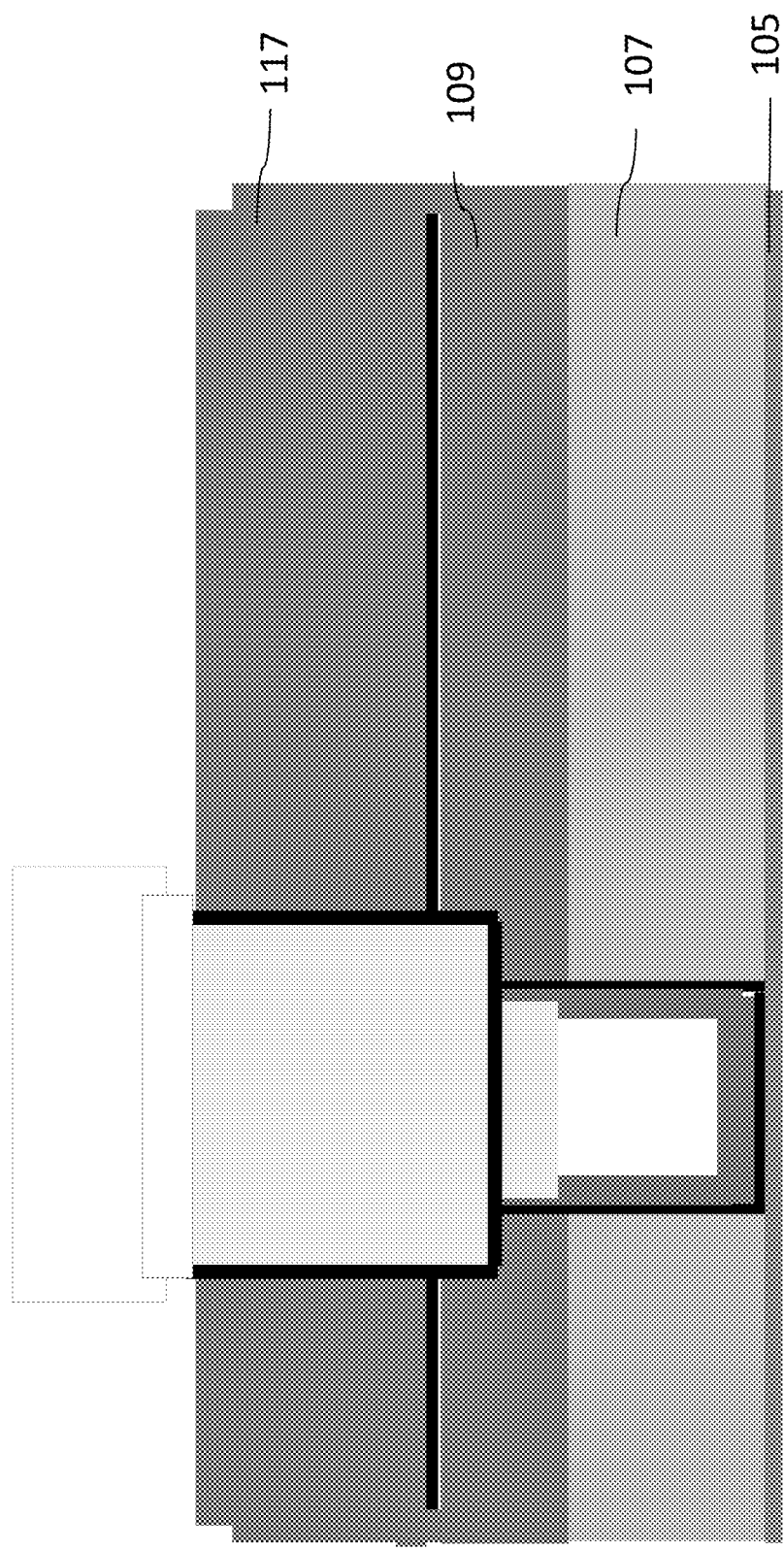

As shown in FIG. 20, a material 125 can then be deposited to fill inlet channels 122. In certain embodiments, material 125 may comprise tetraethyl orthosilicate oxide or TiN/tungsten. Referring now to FIG. 21, material 125 above the layer 117 may be removed by a CMP process, which terminates at layer 117. It is understood that the figures are not to scale, and that the top surface of layer 117 and material 125 may be generally planar or have a small topography.

Figure 22:
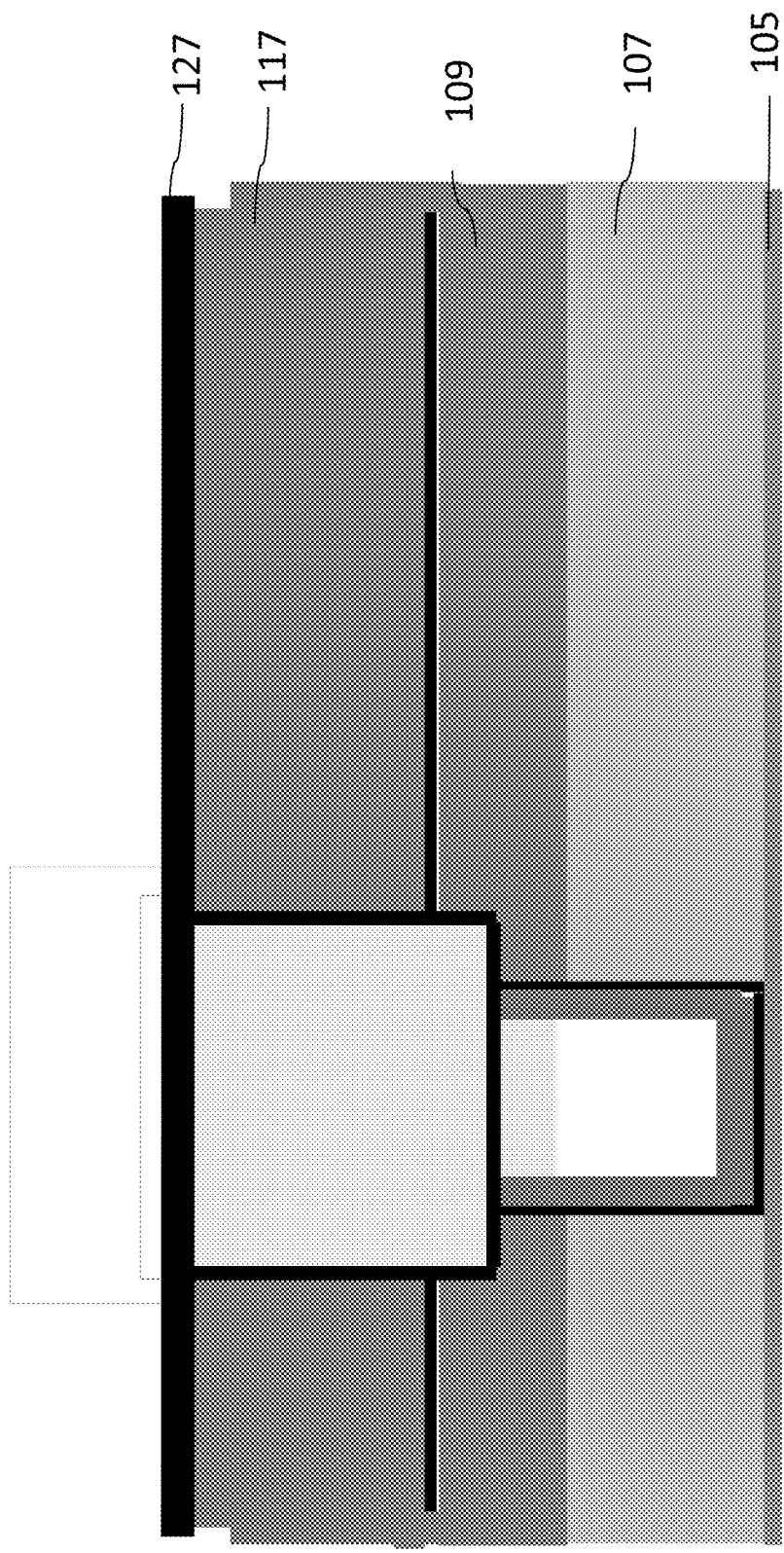
Figure 23:
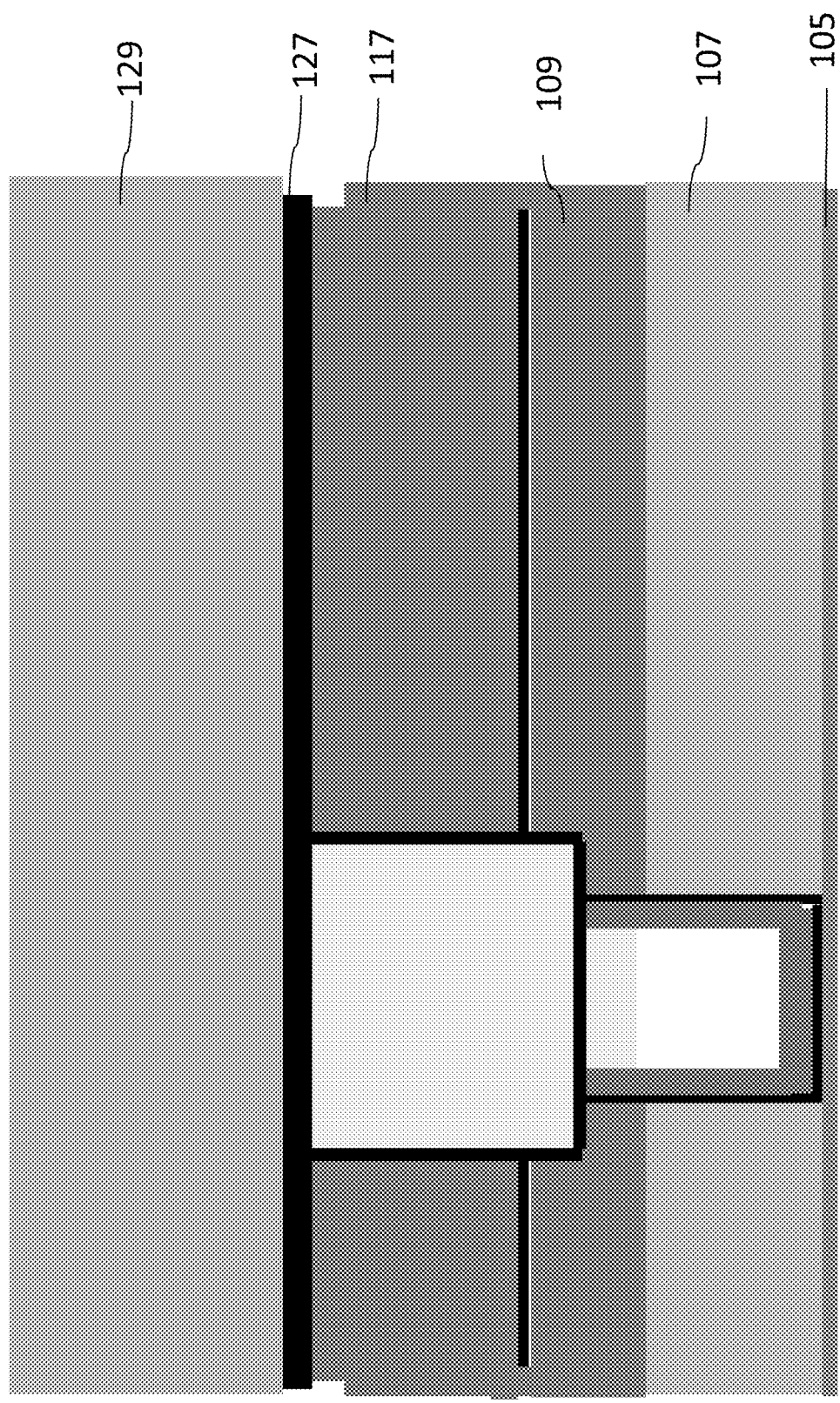

Referring now to FIG. 22, a layer 127 is deposited across the surface of wafer 100 to protect subsequently deposited layer 129 from bio-fluids in the inlet. In certain embodiments, layer 127 may comprise silicon carbide or an ALD $Ta_2O_5$ layer or a combination of the two. A layer 129 is then deposited on layer 127, as shown in FIG. 23. Layer 129 should provide structural integrity to the nanochannel device such that the aggregate stress of the overlayers above the nanochannels should be neutral or mildly tensile in nature (0-100 MPa), but need not be bio-robust. In certain embodiments, layer 129 may comprise silicon nitride.

Figure 24:
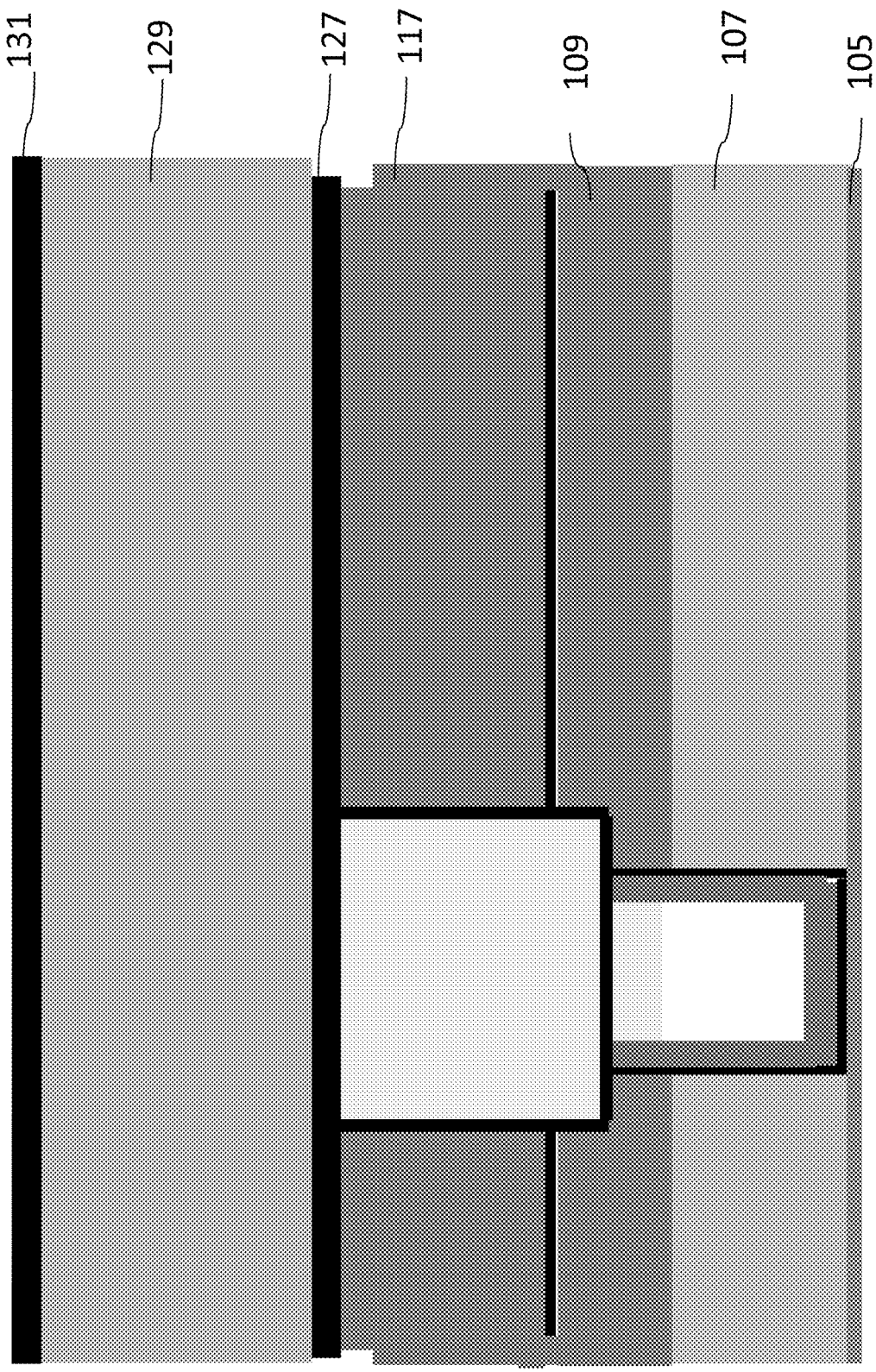
Figure 25:
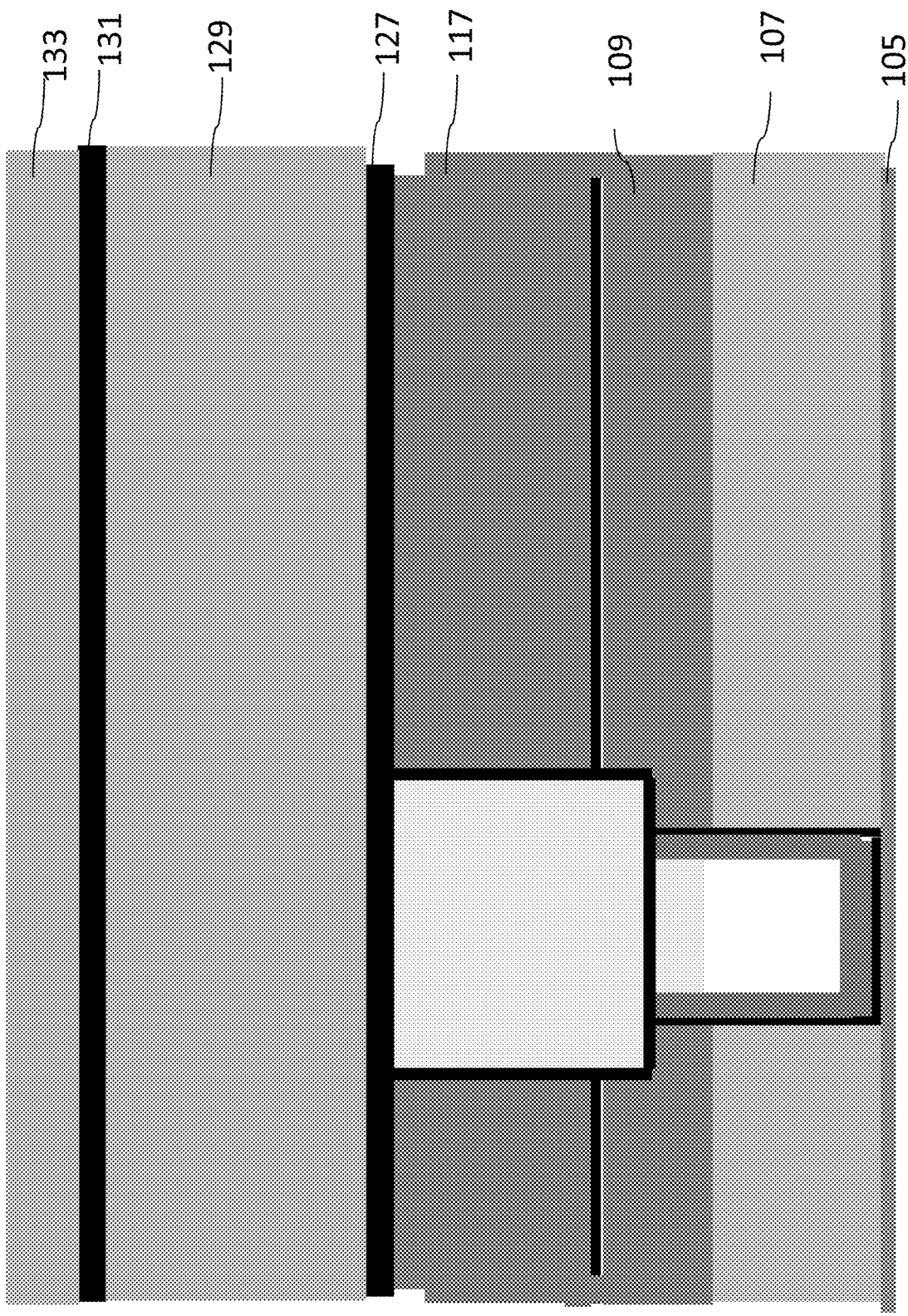
Figure 26:
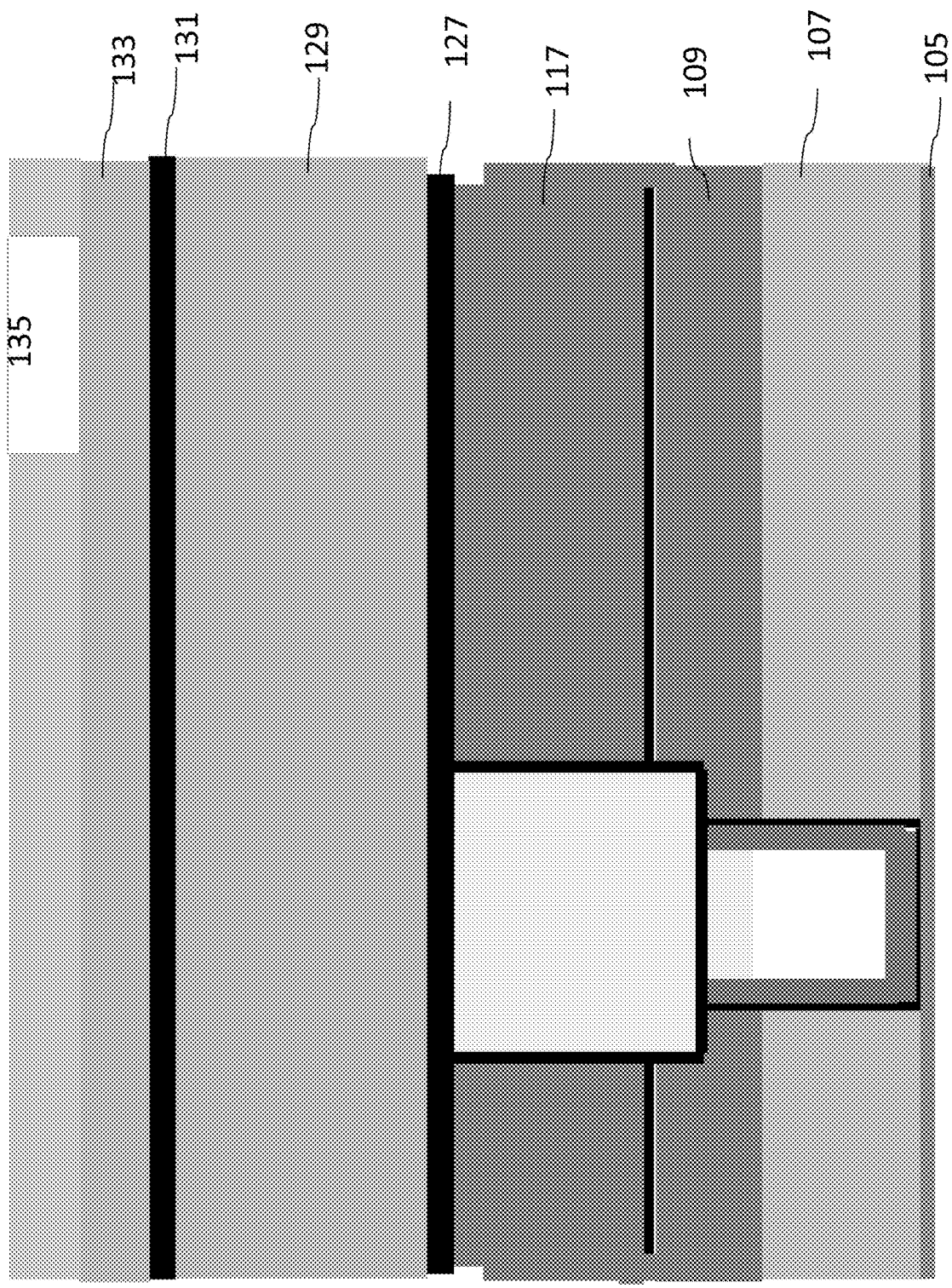
Figure 27:
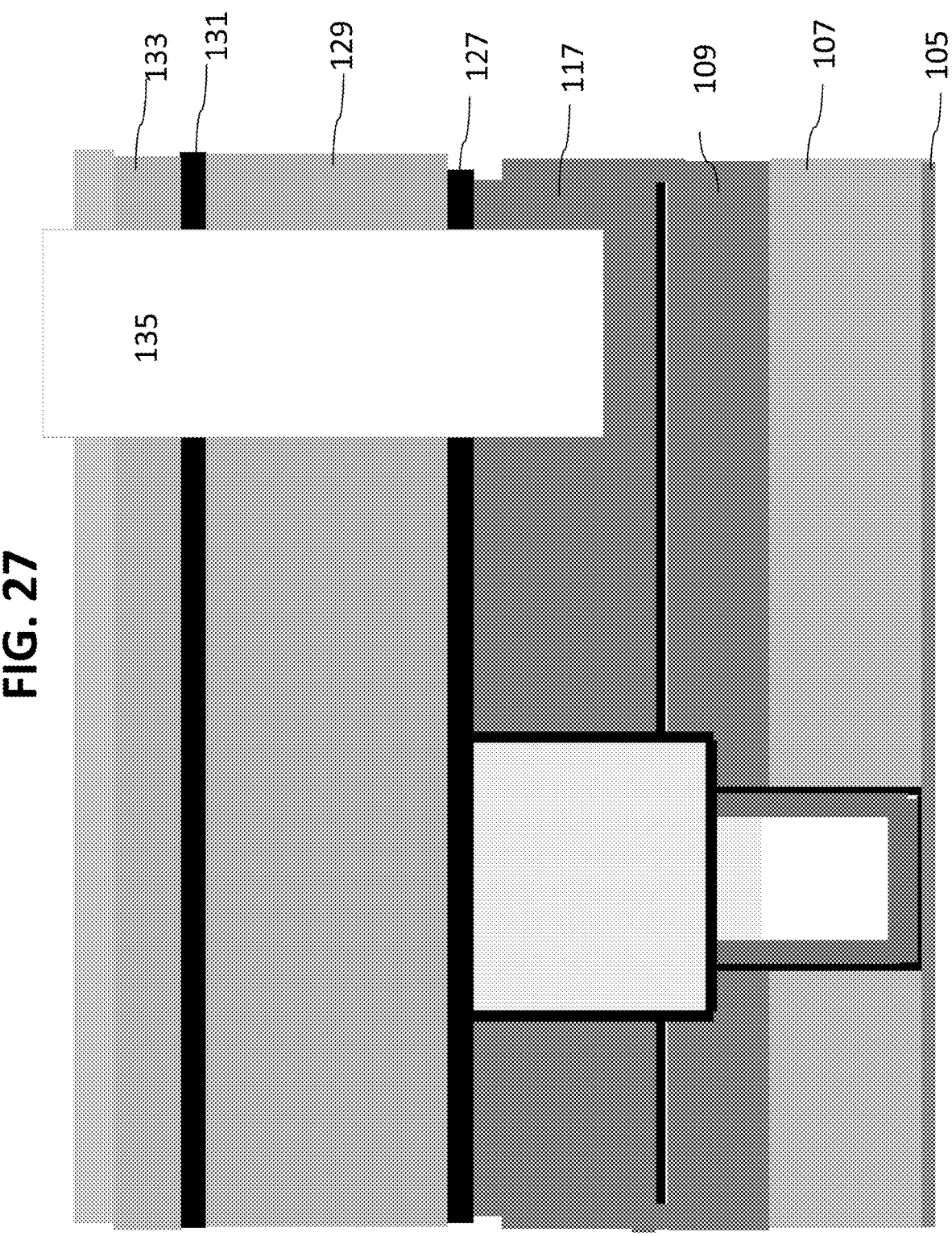
Figure 28:
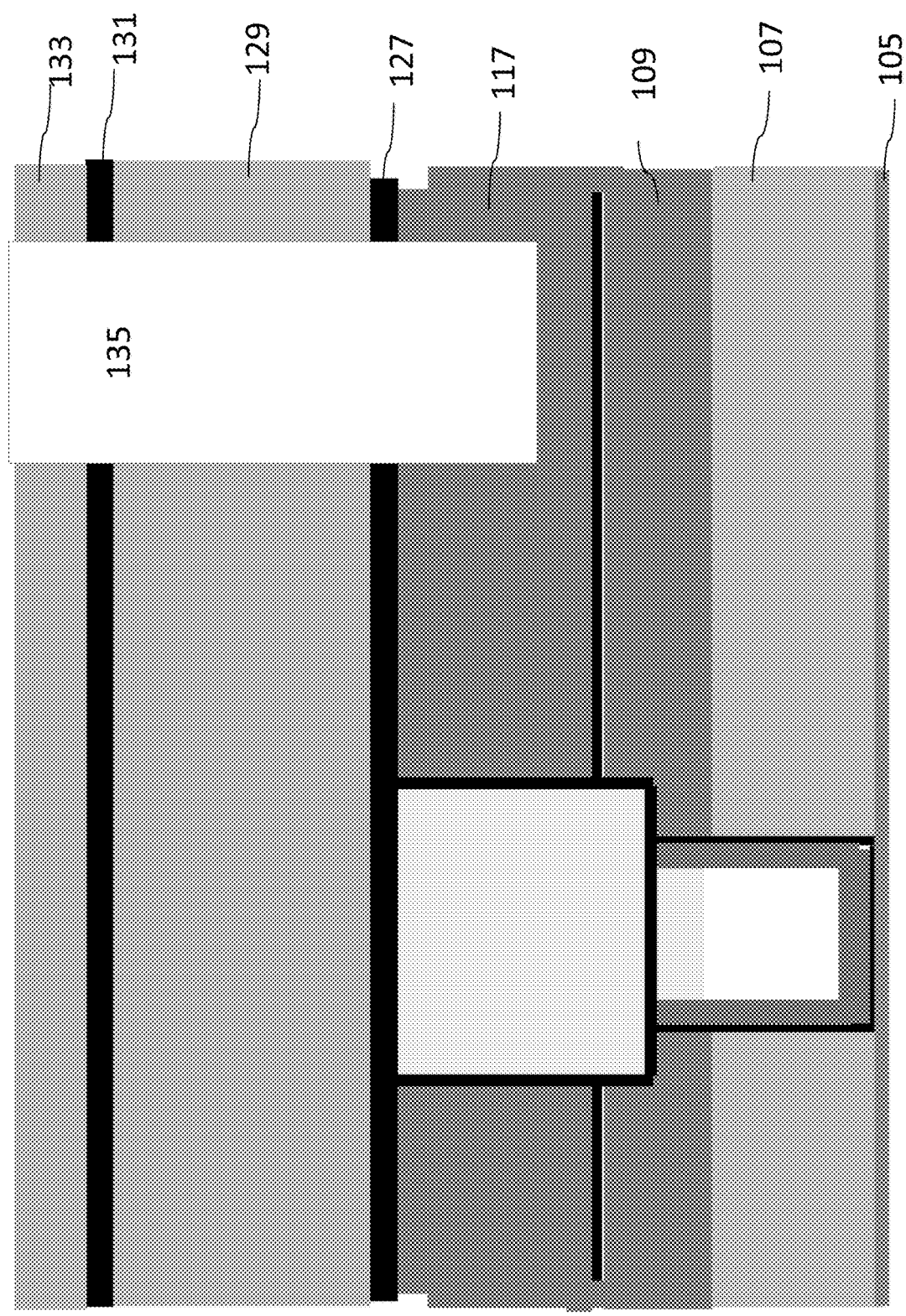

As shown in FIG. 24, a layer 131 can then be deposited on layer 129. In certain embodiments, layer 131 may comprise silicon carbide or an ALD $Ta_2O_5$ layer or a combination of the two. An oxide or a silicon nitride mask layer 133 can then be deposited onto layer 131, as shown in FIG. 25. Referring now to FIG. 26, outlet channels 135 can then be patterned on mask layer 133. As shown in FIG. 27, the wafer is etched through layers 133, 131, 129, 127 and stopping in layer 117. The photoresist material can then be stripped and wafer 100 cleaned as in FIG. 28.

Figure 29:
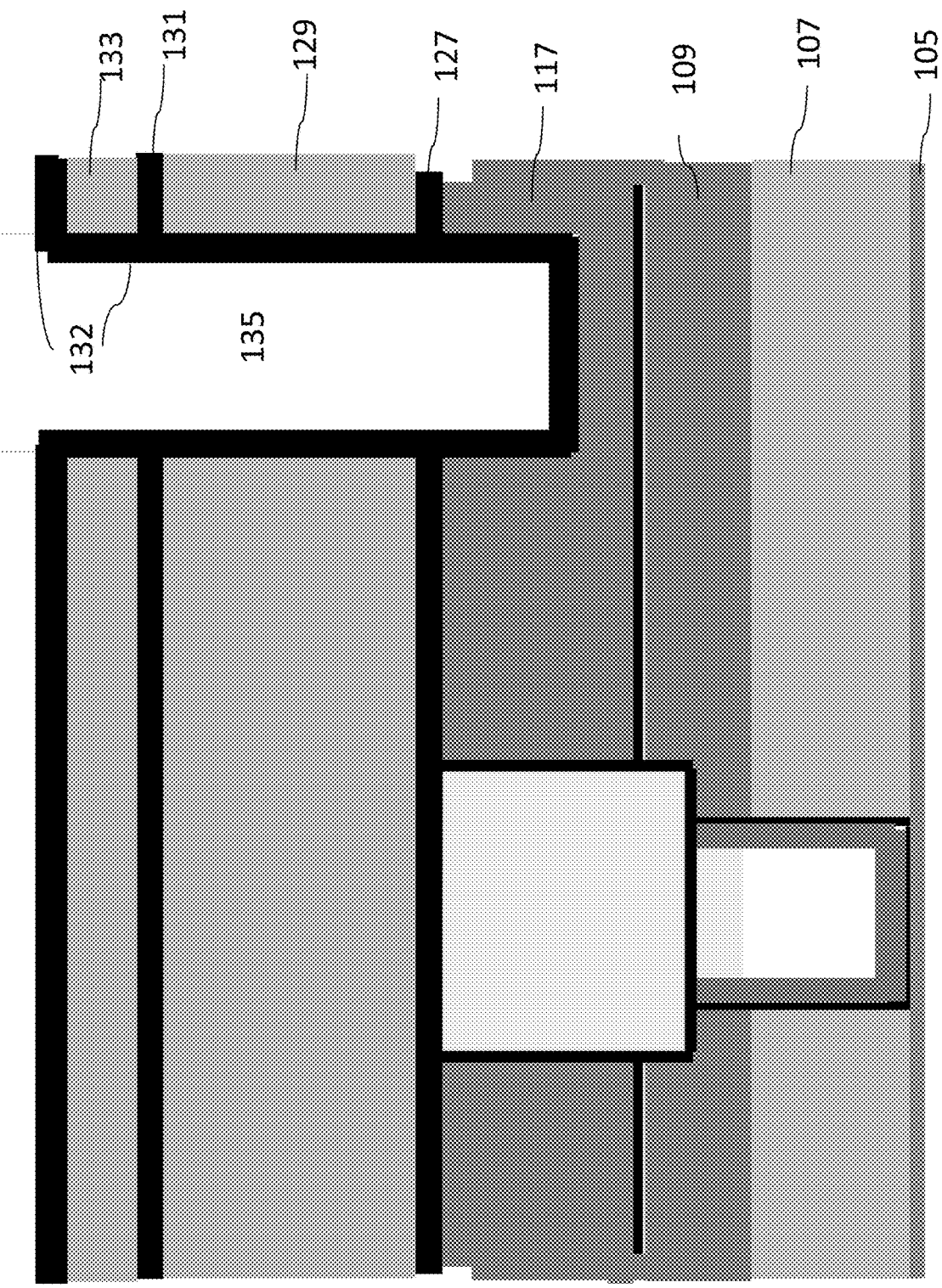
Figure 30:
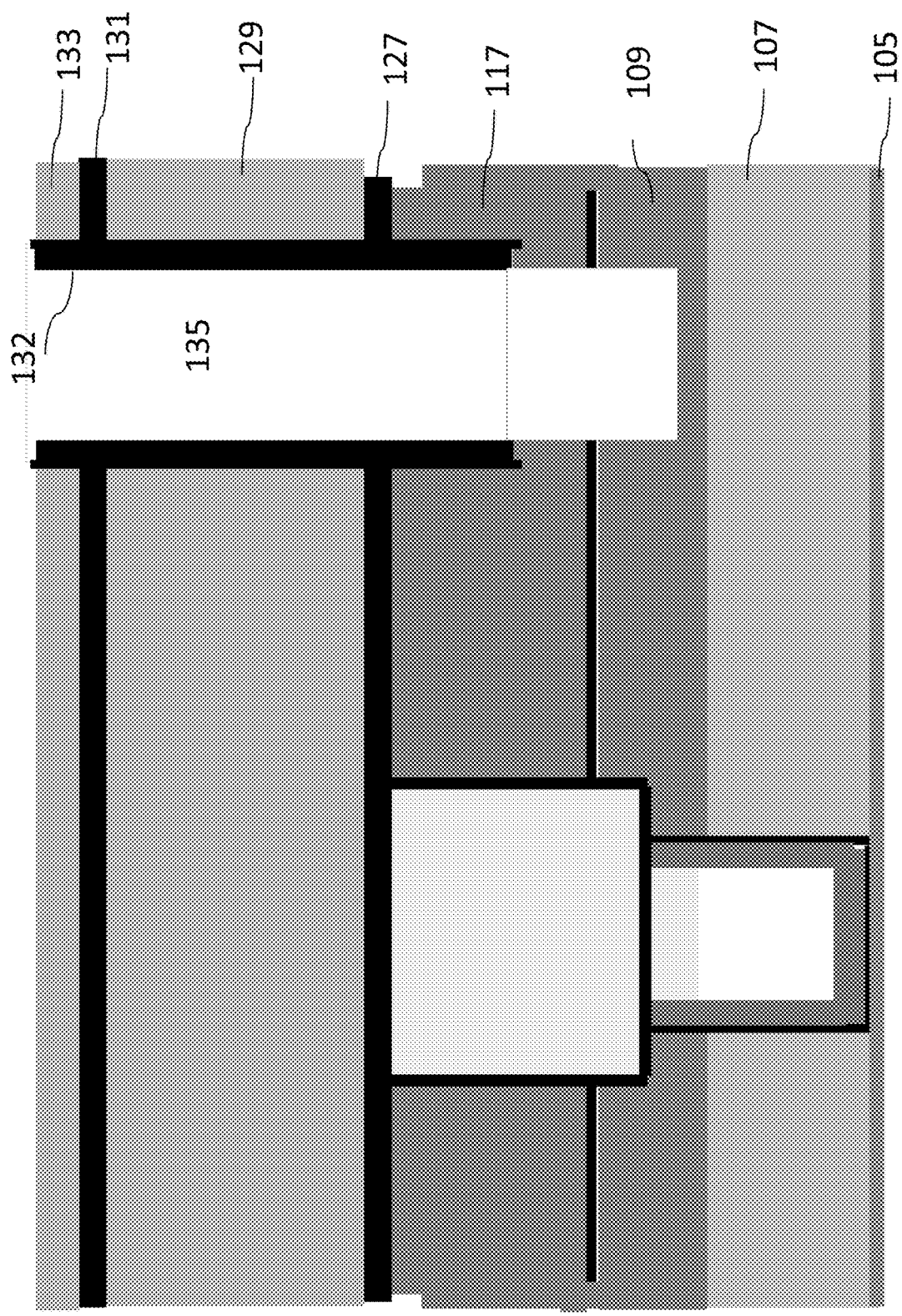
Figure 31:
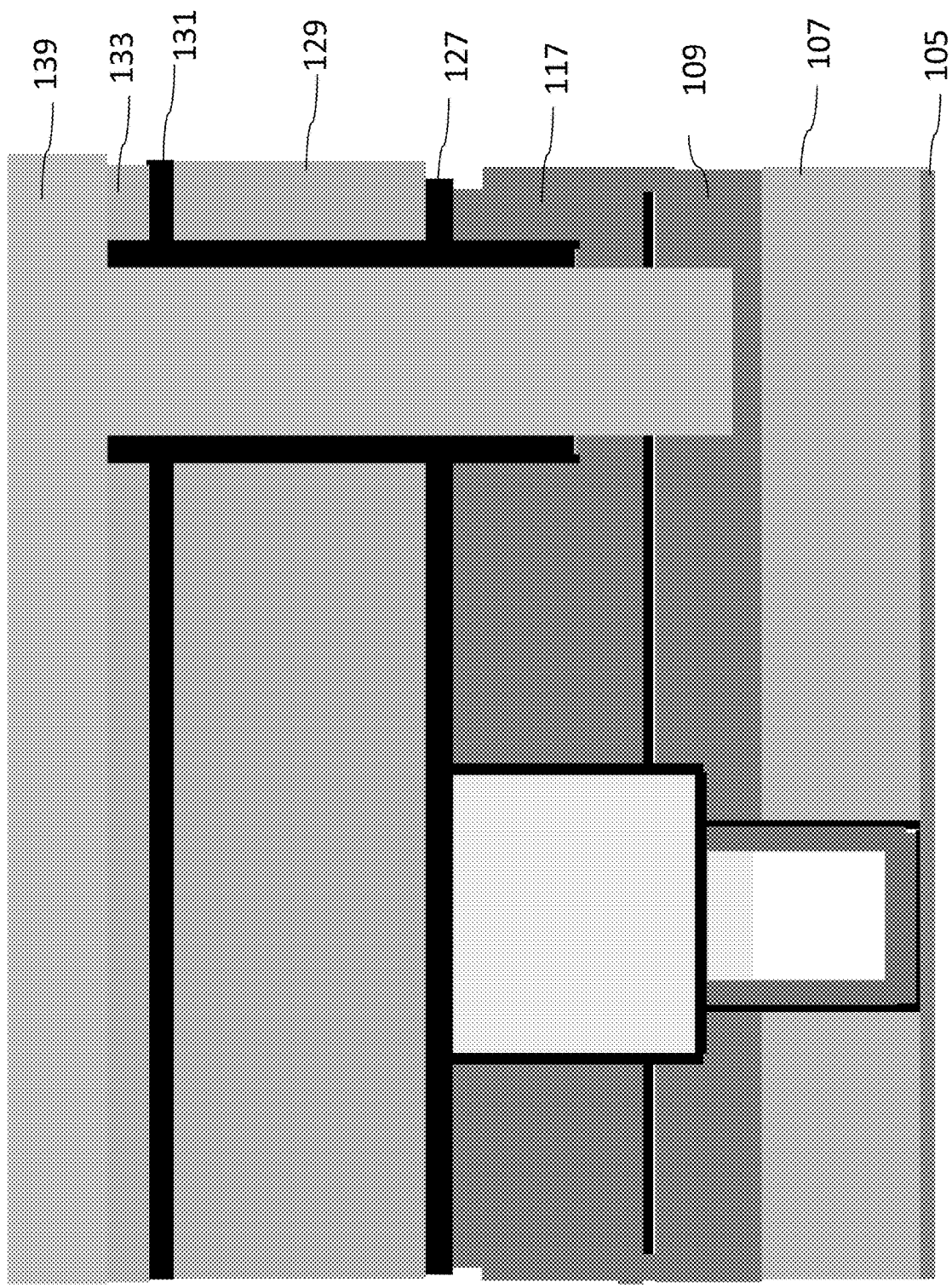

As shown in FIG. 29, a layer 132 can be deposited to form a thin layer within outlet channels 135. Layer 132 can therefore coat or cover the exposed portions of layer 129 (which possesses beneficial structural properties, but may not necessarily be bio-robust). In certain embodiments, this layer may comprise silicon carbide, or ALD $Ta_2O_5$ or a combination of the two. Referring now to FIG. 30, an additional etching step can be performed to extend outlet channels 135 through layer 117 and nanochannel layer 111 and stopping in layer 109 and the wafer cleaned. Referring now to FIG. 31, a protection layer 139 can be deposited onto layer 133 and into outlet channel 135.

Figure 32:
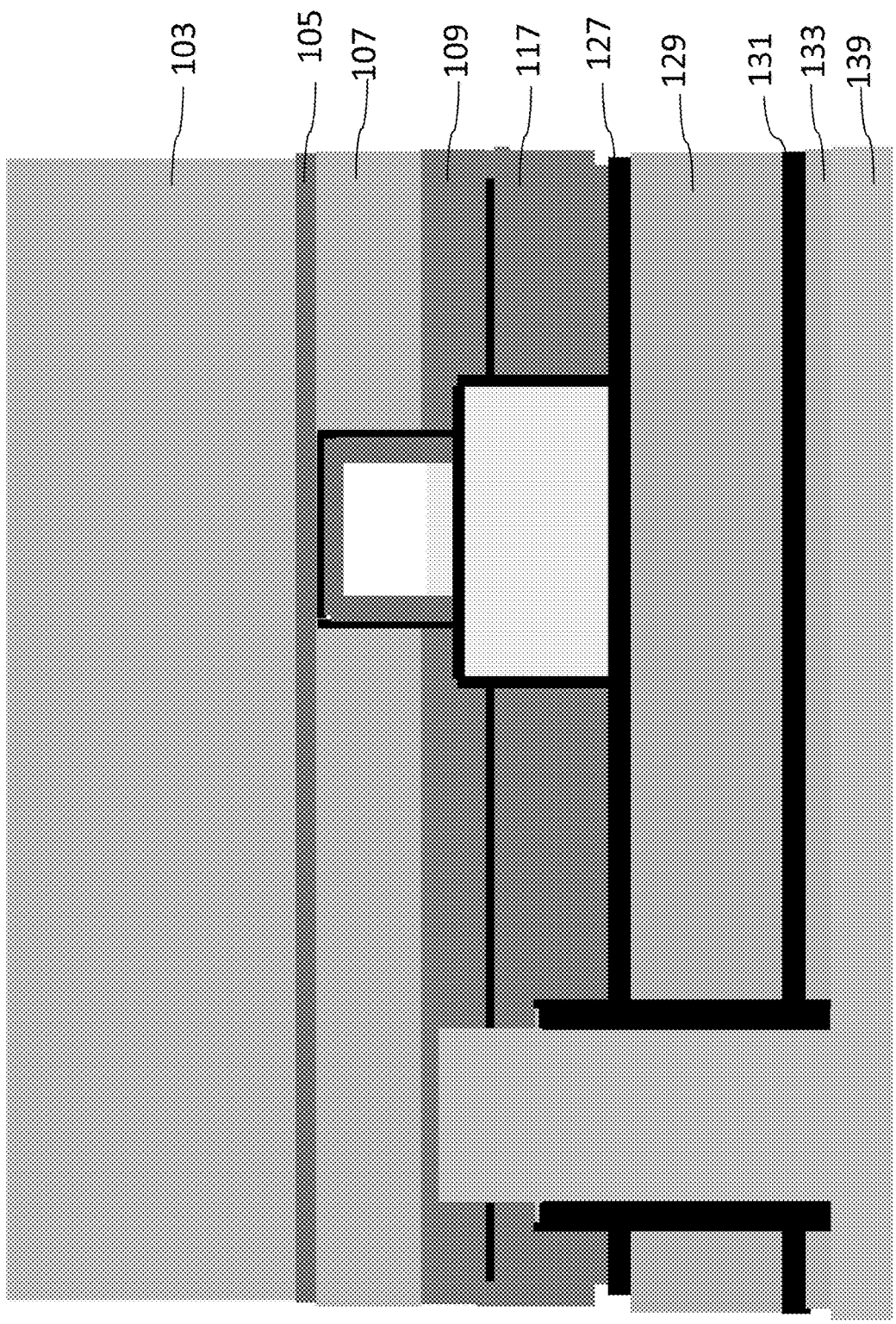
Figure 33:
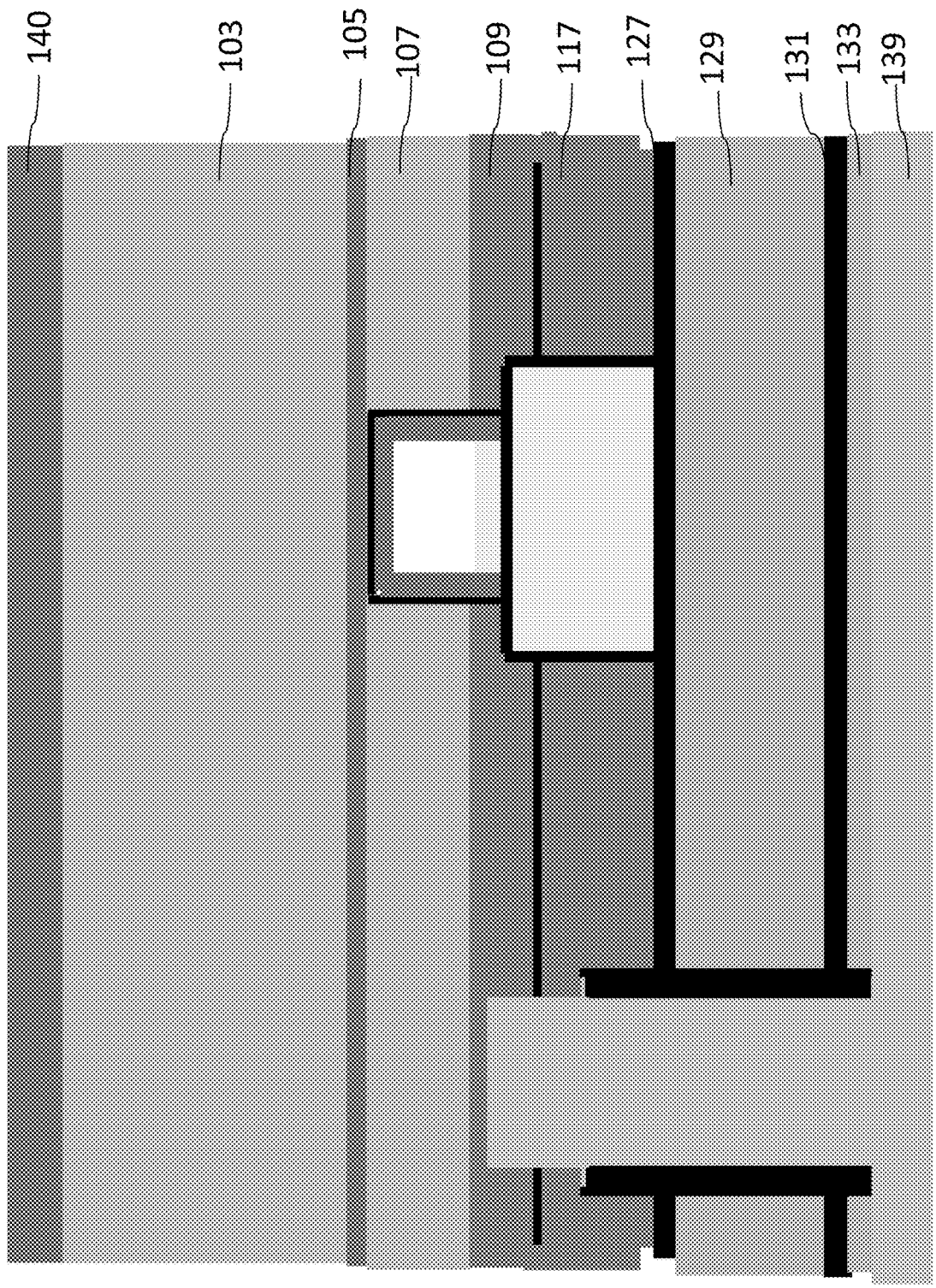
Figure 34:
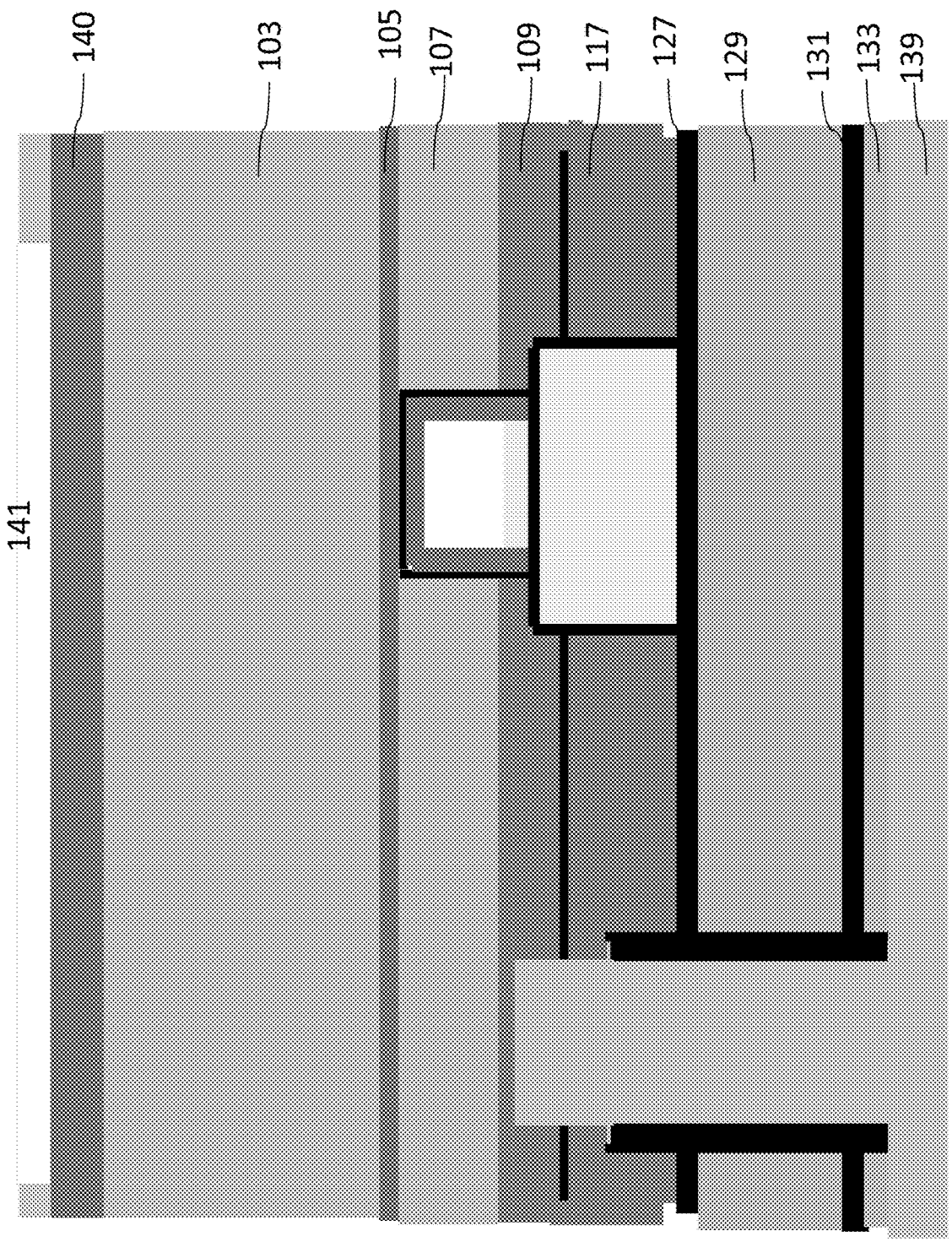

At this stage, wafer 100 can turned over, as shown in FIG. 32. A hardmask layer 140 is deposited on the backside as in FIG. 33. Macrochannels 141 are patterned with resist on this layer 140, with alignment to the frontside as shown in FIG. 34.

Figure 35:
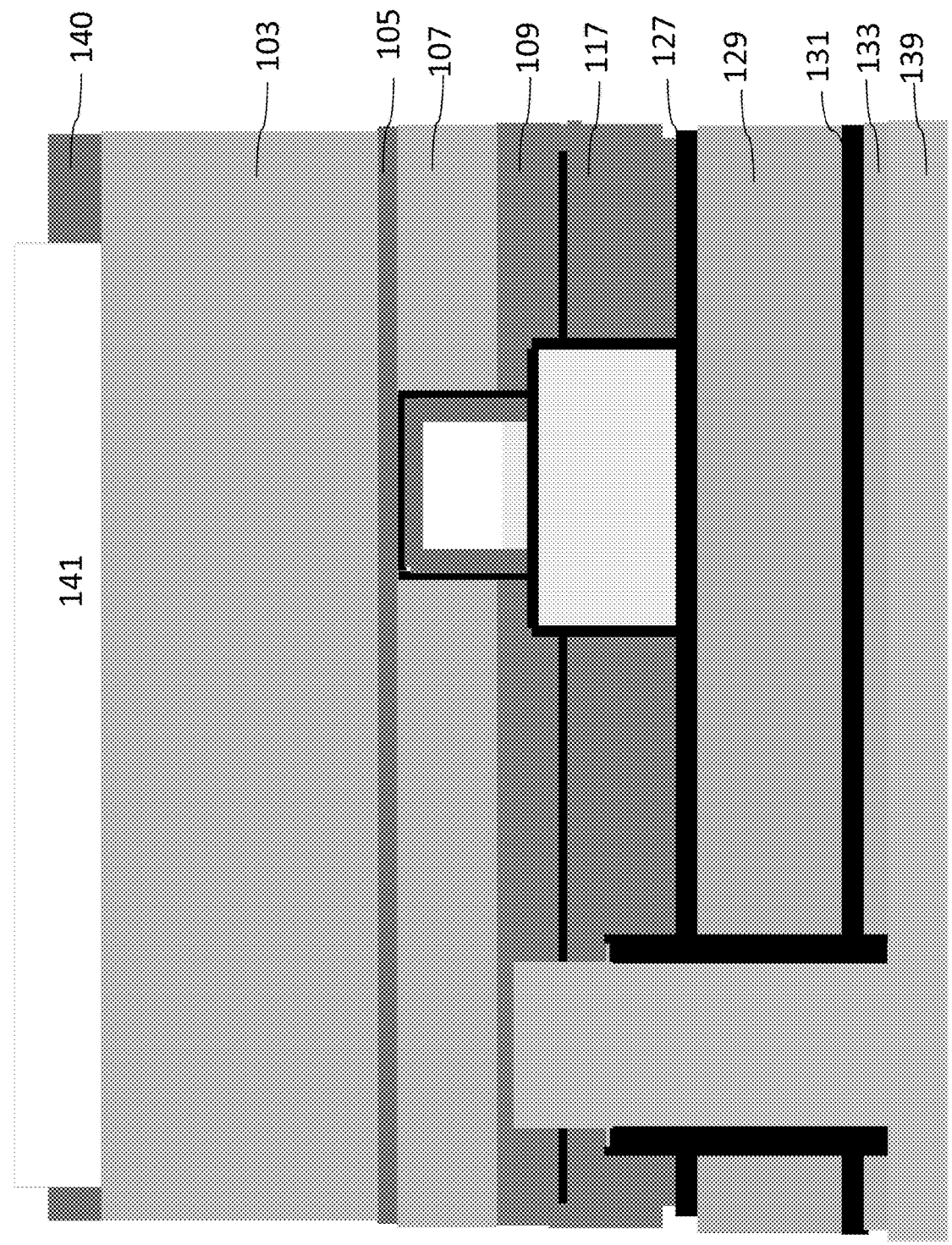

Referring to FIG. 35, layer 140 is etched and the resist stripped and cleaned, to transfer the macrochannel pattern 141 to the hardmask. Optionally, this pattern transfer to hardmask is not needed and the macrochannel pattern is made in resist only.

Figure 36:
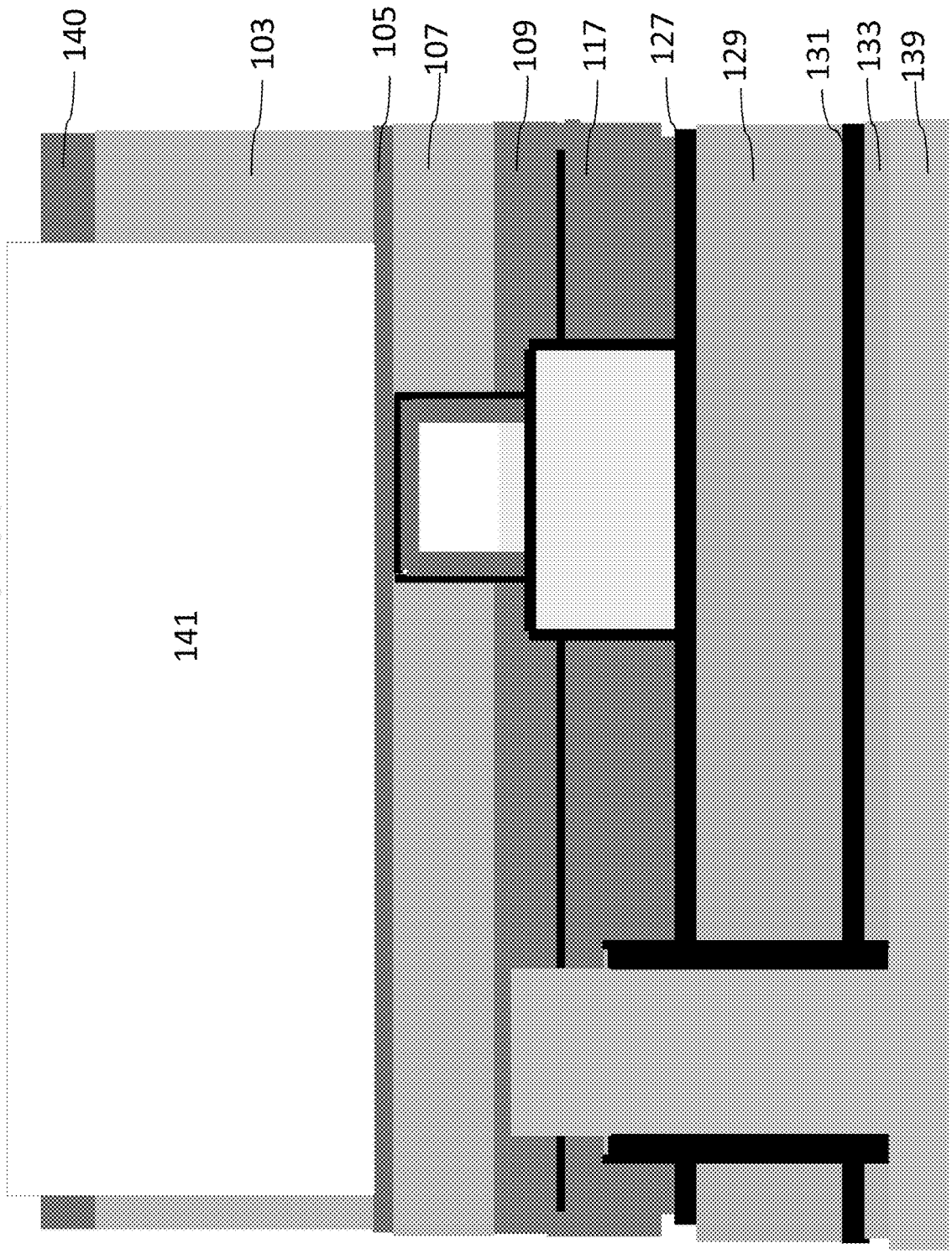
Figure 37:
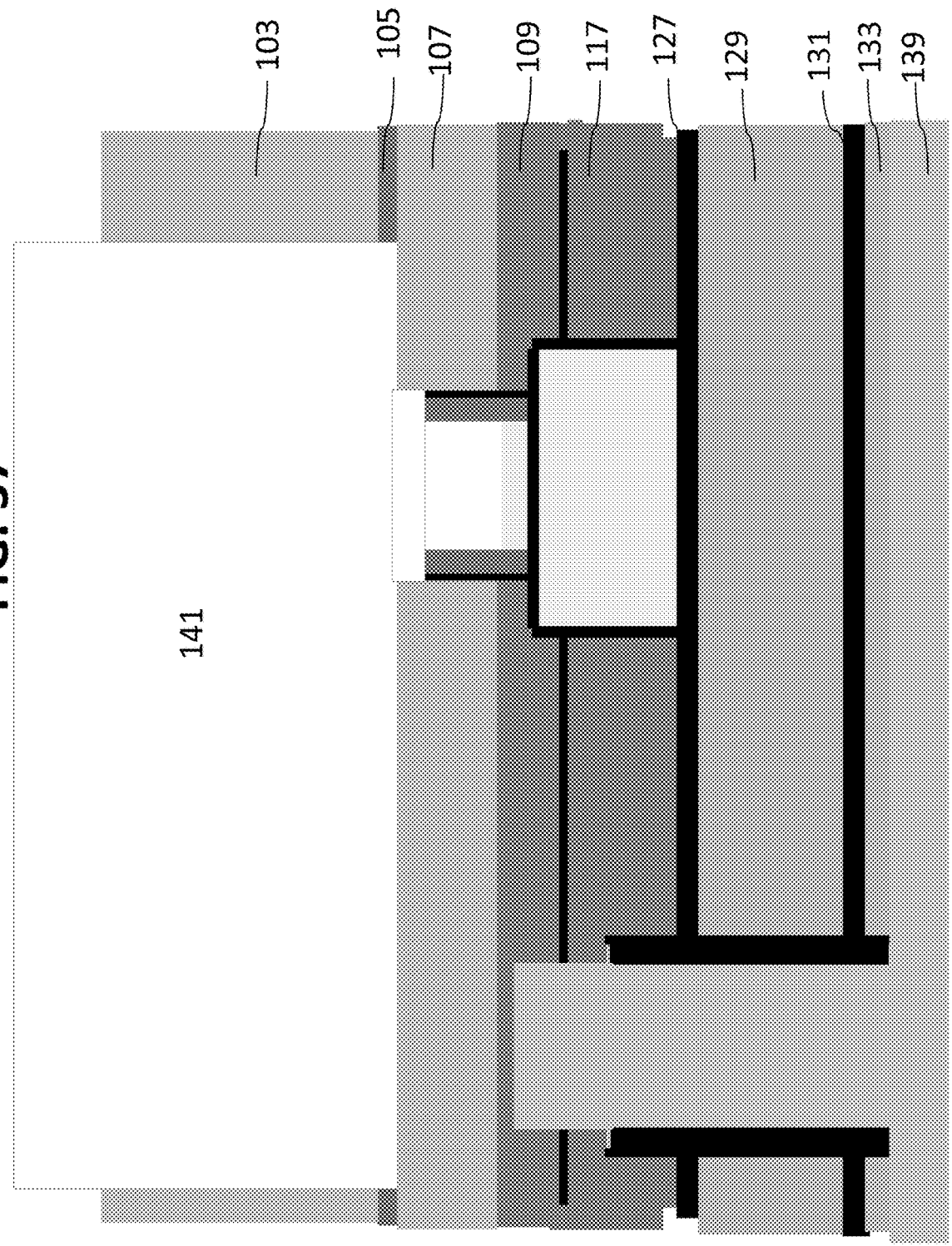
Figure 38:
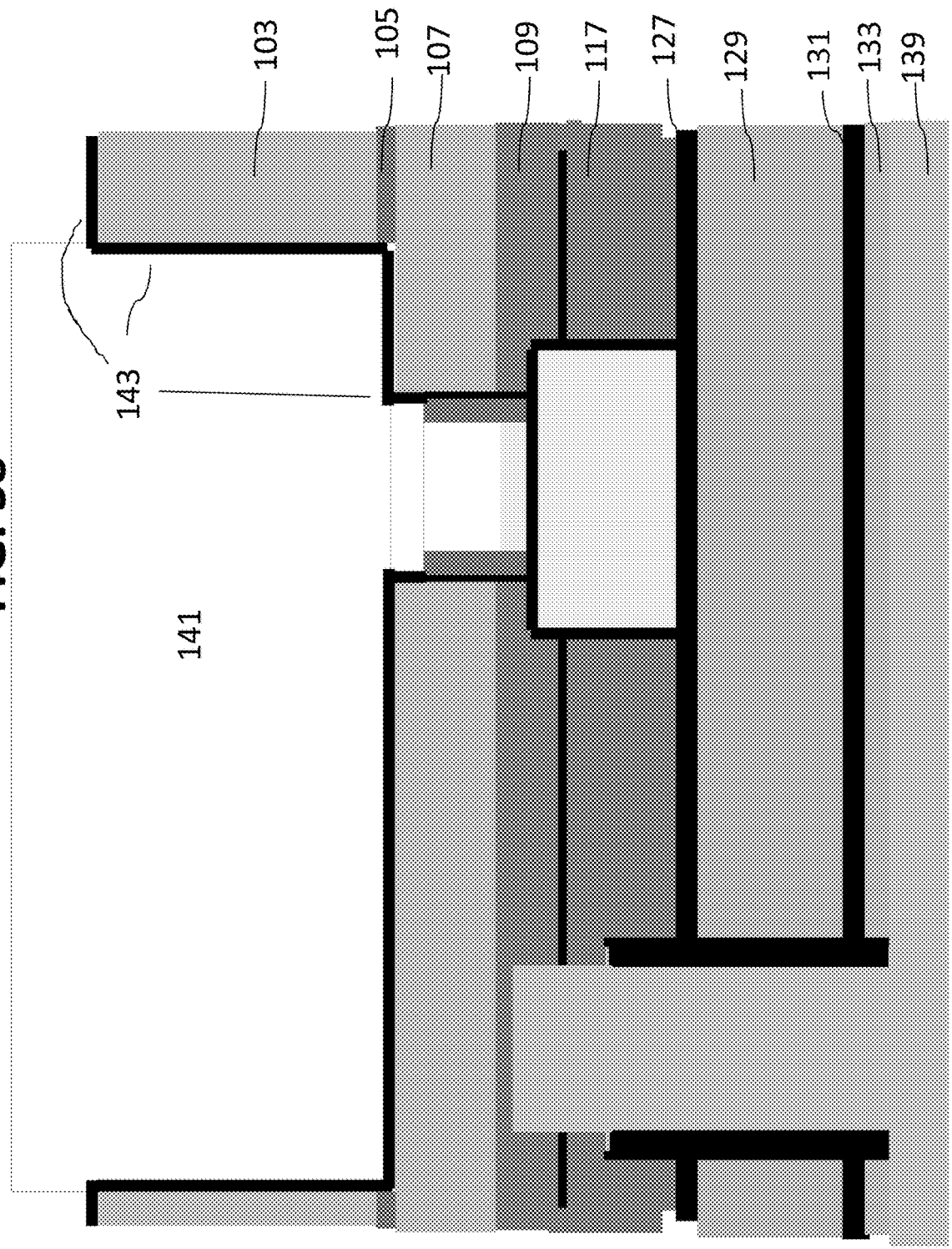

Macrochannels are then etched in layer 103, stopping at oxide layer 105, as shown in FIG. 36. Additional treatments to prepare a contamination free, smoother sidewall can be performed at this stage, for example, piranha and other cleans and KOH, $SF_6$ or other silicon etches. Referring now to FIG. 37, oxide layer 105 can then be removed and macrochannels 141 extended to the device silicon layer 107. This process also removes the hardmask layer 140. An additional layer 143 of bio-robust material can then be deposited to cover the backside of the wafer 100, as shown in FIG. 38. This, again can be silicon carbide, $Ta_2O_5$, or a combination of the two.

Figure 39:
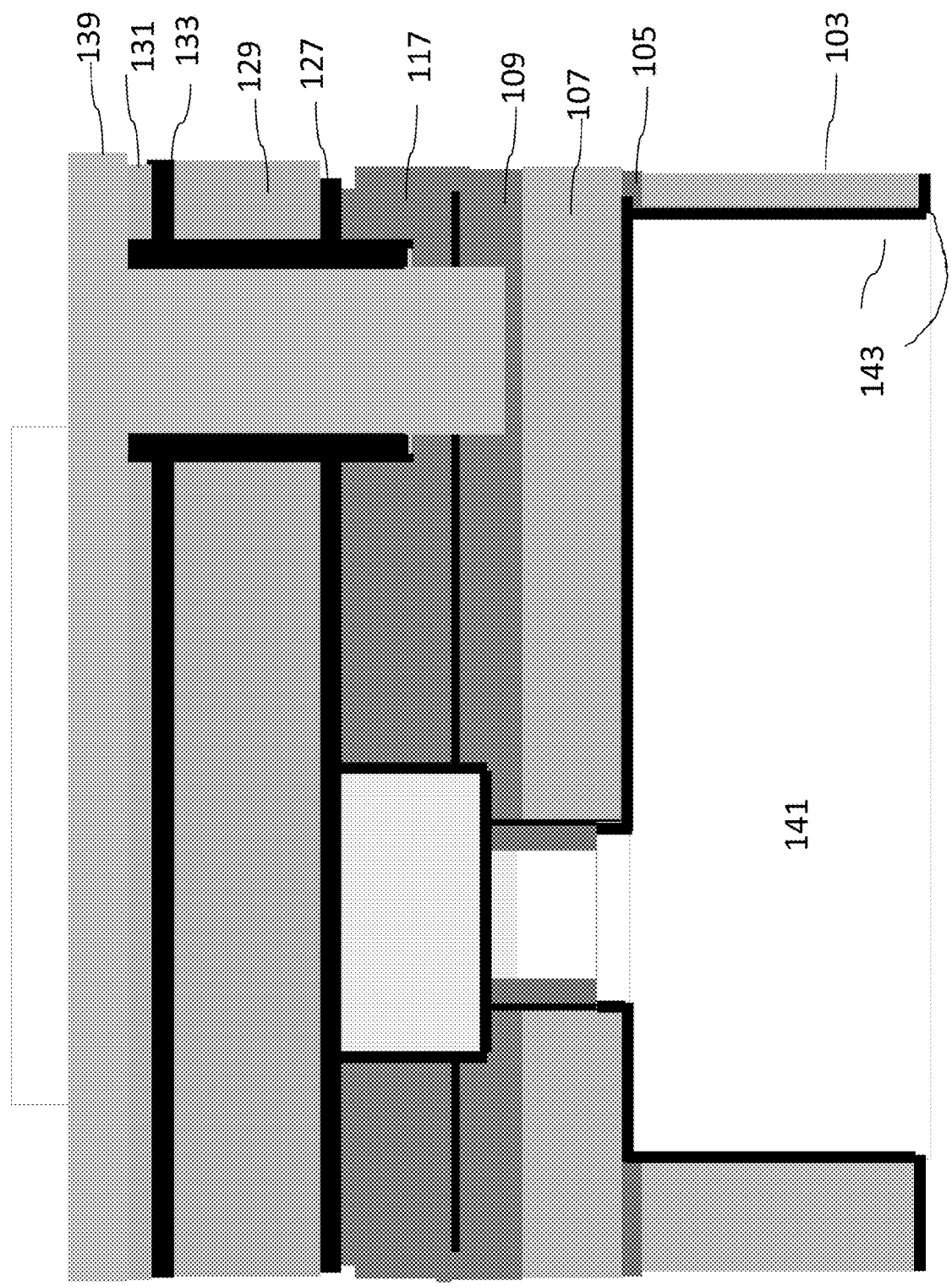
Figure 40:
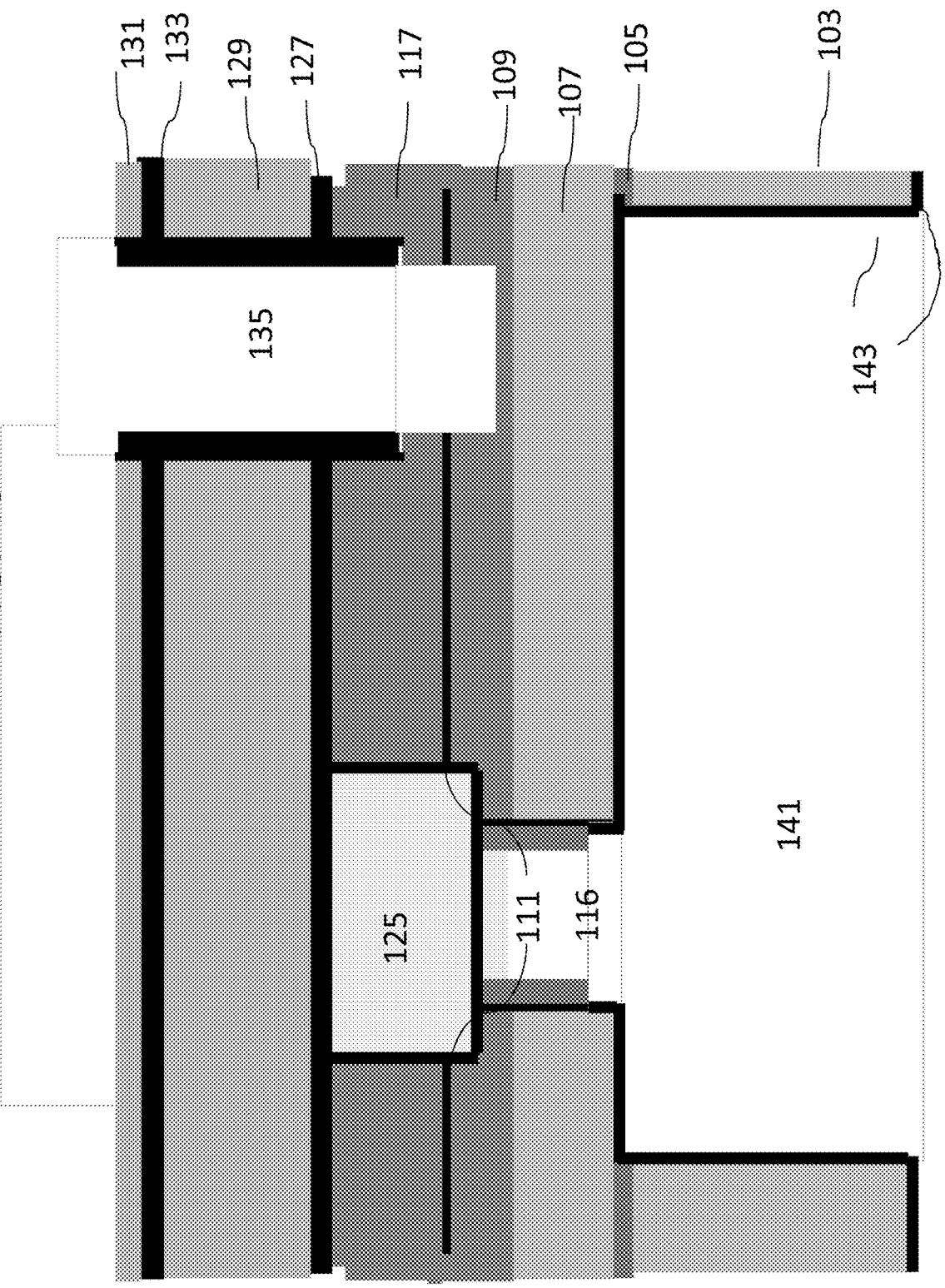
Figure 41:
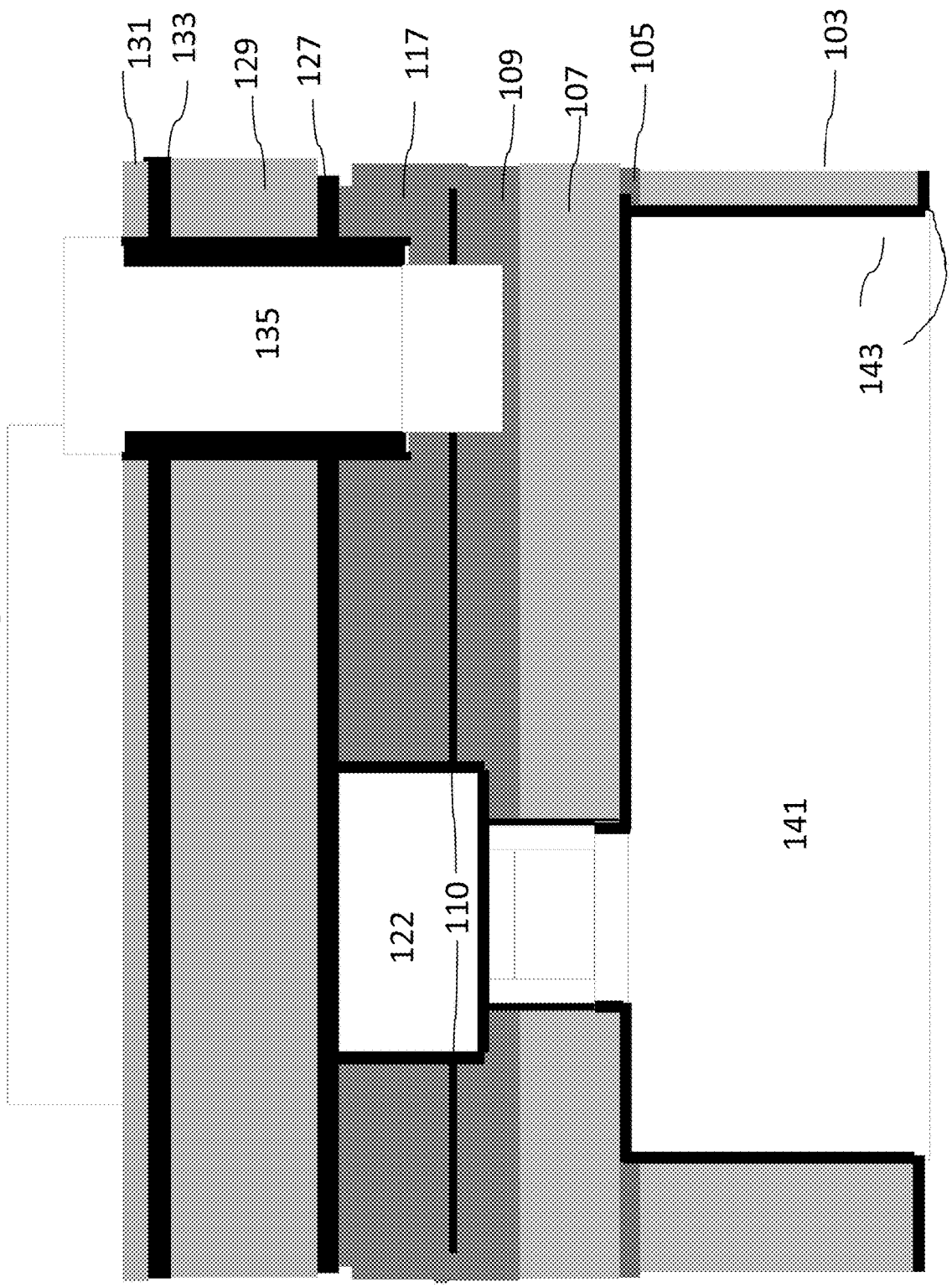

The wafer is then flipped over to face-up position, as shown in FIG. 39. As shown in FIG. 40, the frontside protection layer 139 is removed by appropriate means. Finally, as shown in FIG. 41, the sacrificial materials such as material 125, material 121, nanochannel layer 111, and protection layer 116 are removed. As shown in FIG. 41, nanochannel 110 (resulting from the removal of nanochannel layer 111) couples macrochannel 141 and inlet microchannel 122 with outlet microchannel 135.

Figure 42:
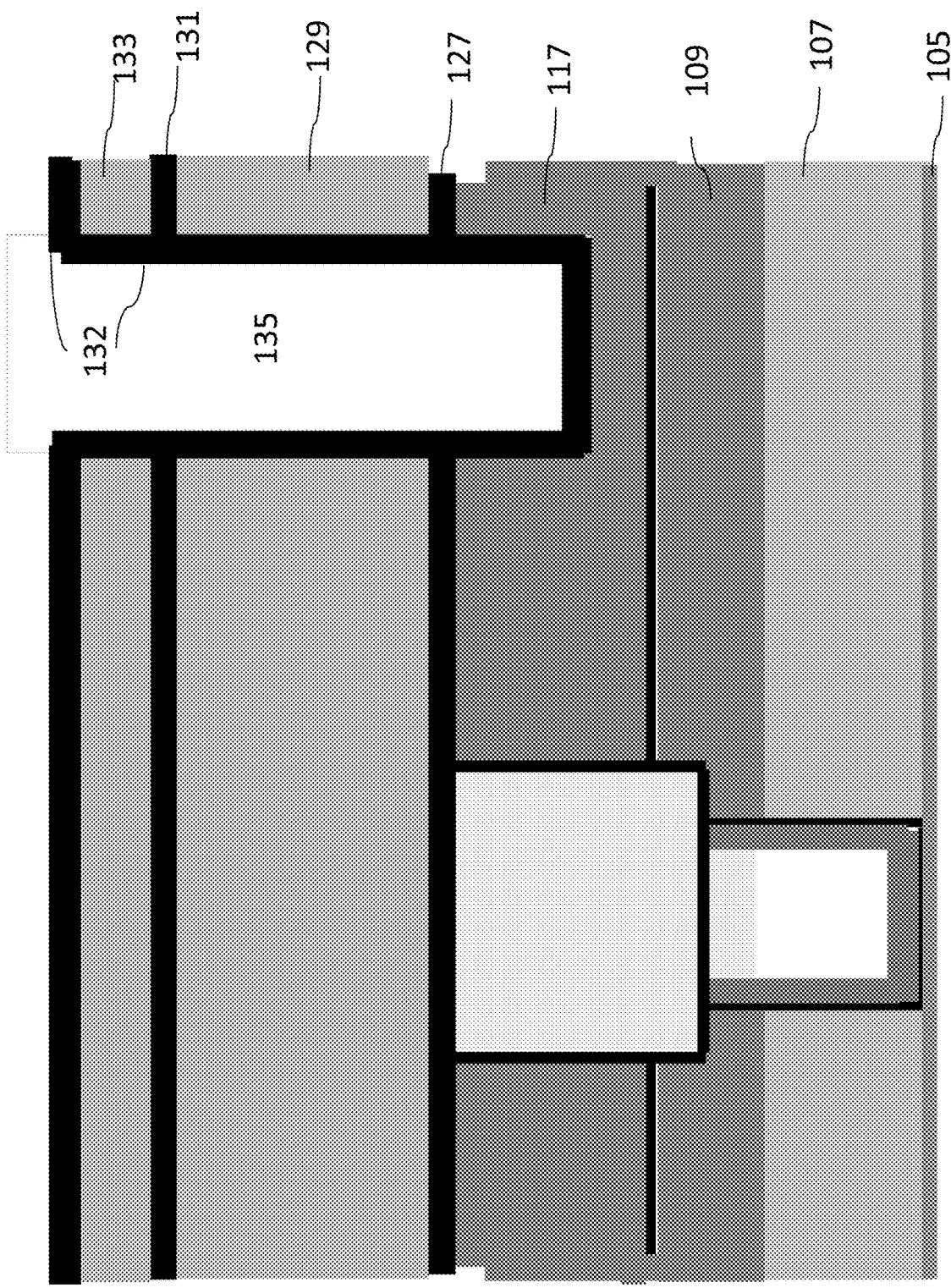
Figure 43:
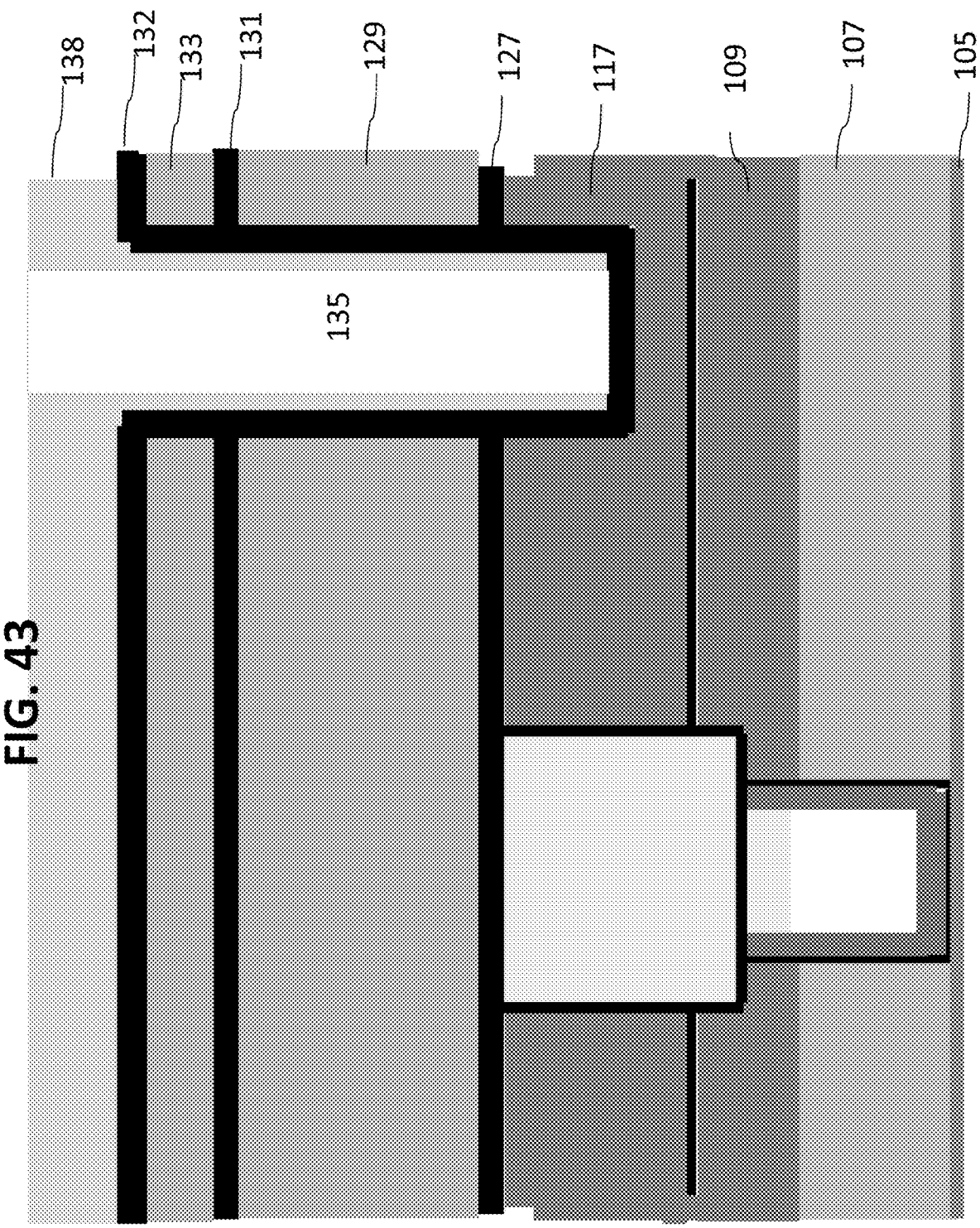
Figure 44:
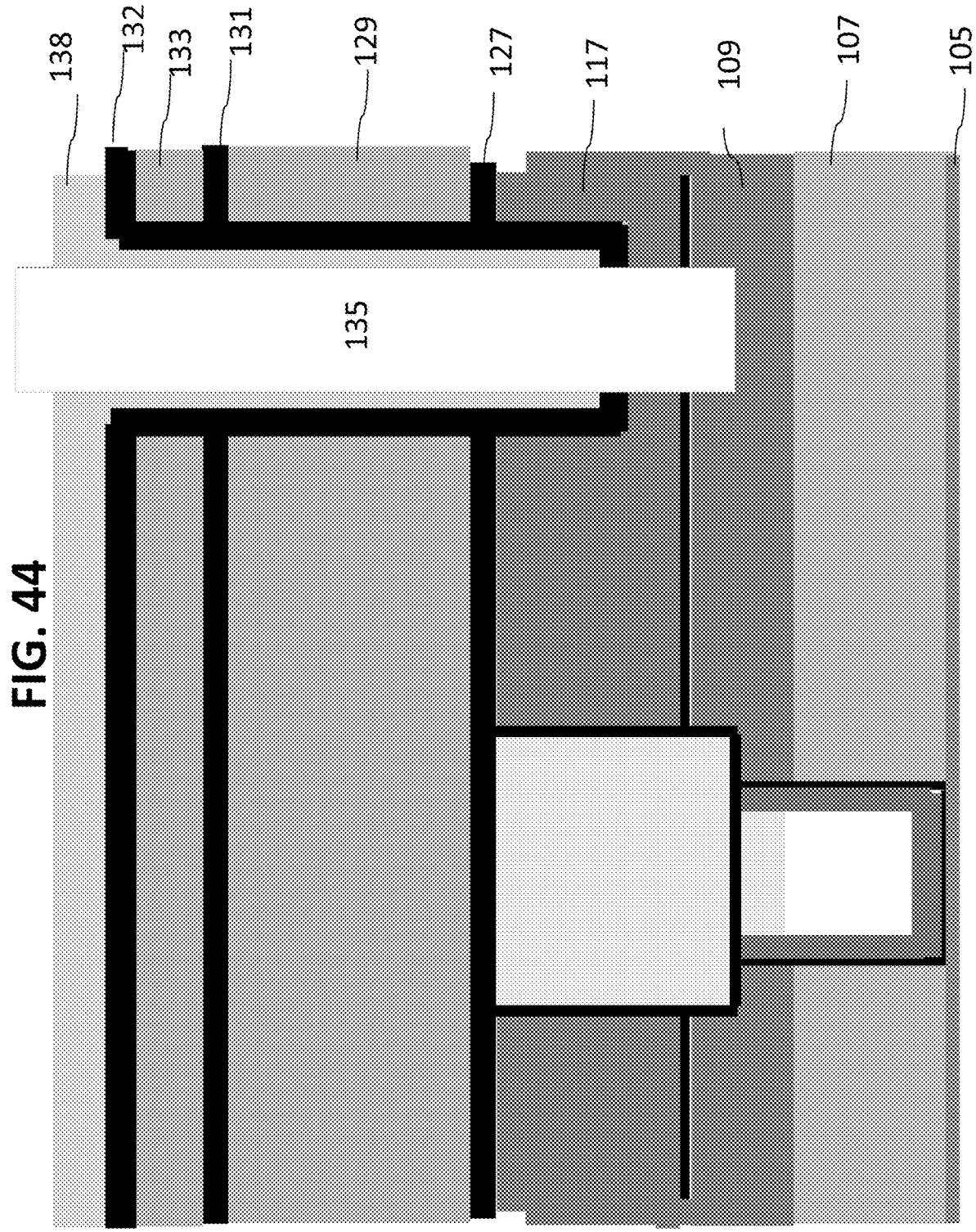
Figure 45:
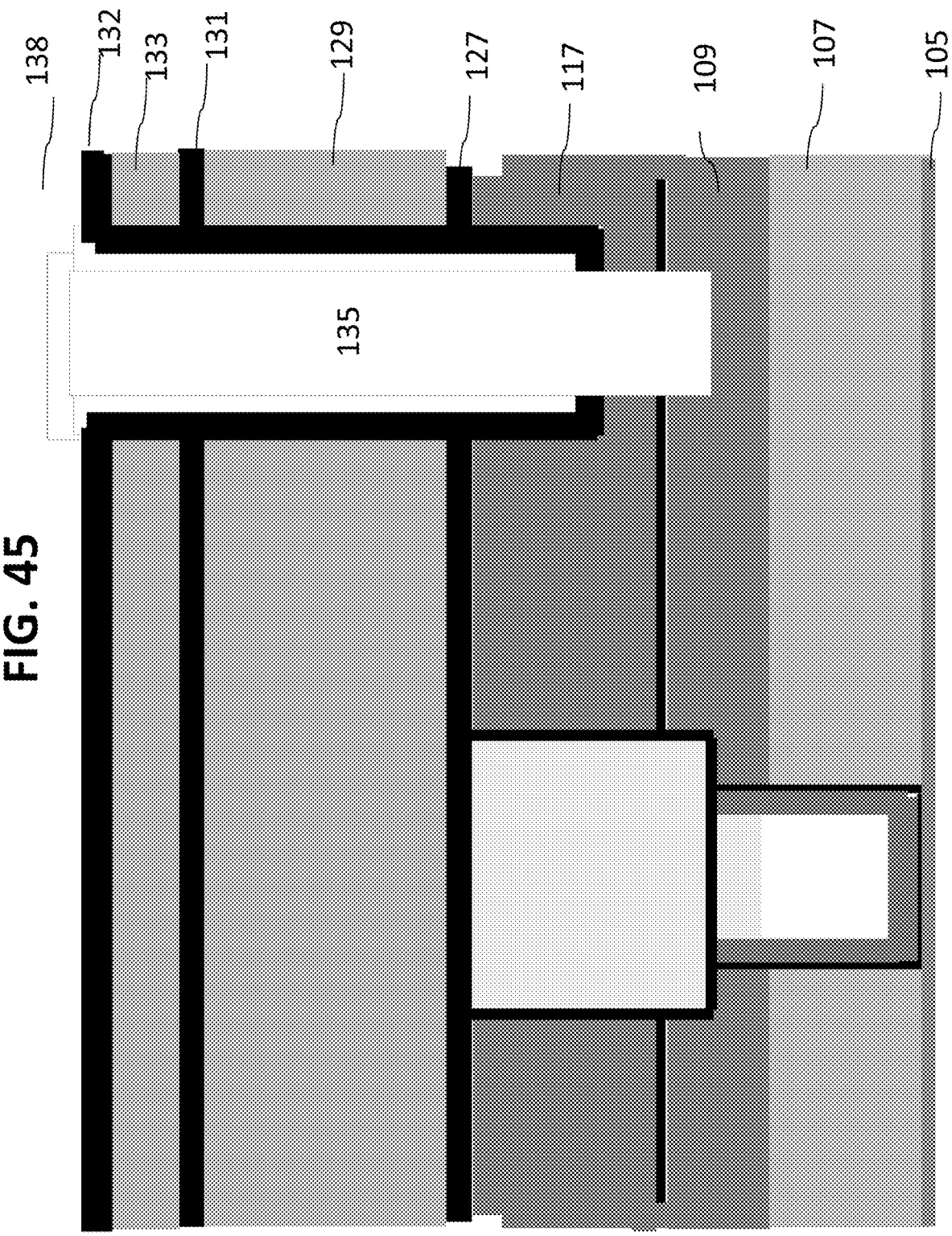

While one exemplary embodiment has been described above, other exemplary embodiments may comprise alternate processes or methods. For example, the processes described in FIGS. 29-30 may be substituted by those described in the following FIGS. 42-45. Processes described in FIGS. 29-30 are performed as a means to open the outlet side of the nanochannel, while still having a bio-robust material covering the sidewalls of the structural material. FIGS. 42-45 disclose an alternate method of accomplishing this, described by using a pattern to form a smaller via inside the original outlet microchannel (after the formation of the first outlet microchannel, followed by the $Ta_2O_5$ and/or silicon carbide deposition) and etch of this second outlet microchannel into the nanochannel, landing in the outlet etch stop material FIG. 42 describes a film stack similar to FIG. 29, that has been patterned with the outlet mask 135 and etched through materials 133, 131, 129, 127 and stopping in layer 117. Subsequently a layer 132 is deposited to cover the sidewalls of layer 129 as shown in FIG. 42. In certain embodiments, this layer can be silicon carbide or ALD Ta2O5 or combinations of the two. Resist is spun on this wafer and a second mask is exposed to pattern a smaller outlet within the larger outlet as layer 138 as shown in FIG. 43. The material from 132, any remaining material of 117 and the nanochannel material 111 is etched, stopping on the etch stop layer 109, and the residual resist removed as shown in FIG. 44. The resist is then stripped and wafer cleaned as shown in FIG. 45.

Furthermore, the process described in FIGS. 15-21 are provided as a means to open the inlet side of the nanochannel, which would otherwise be covered by the liner material. While the method described in FIGS. 15-21 uses a second mask to etch out the liner, alternate methods may be employed to remove the liner at the interface with the inlet. For example, two such methods include: (1) performing a short isotropic etch to sputter away the sidewall containing the liner and (2)) removing the liner with a chemical, etched through the nanochannel, after the nanochannel has been removed.

An alternate method to make the devices with materials protected by bio-robust layers is by changing the sequence of line and inlet formation process from line first, inlet second, to inlet first and line second. This can be accomplished, for example, in the manner described below.

Figure 46:
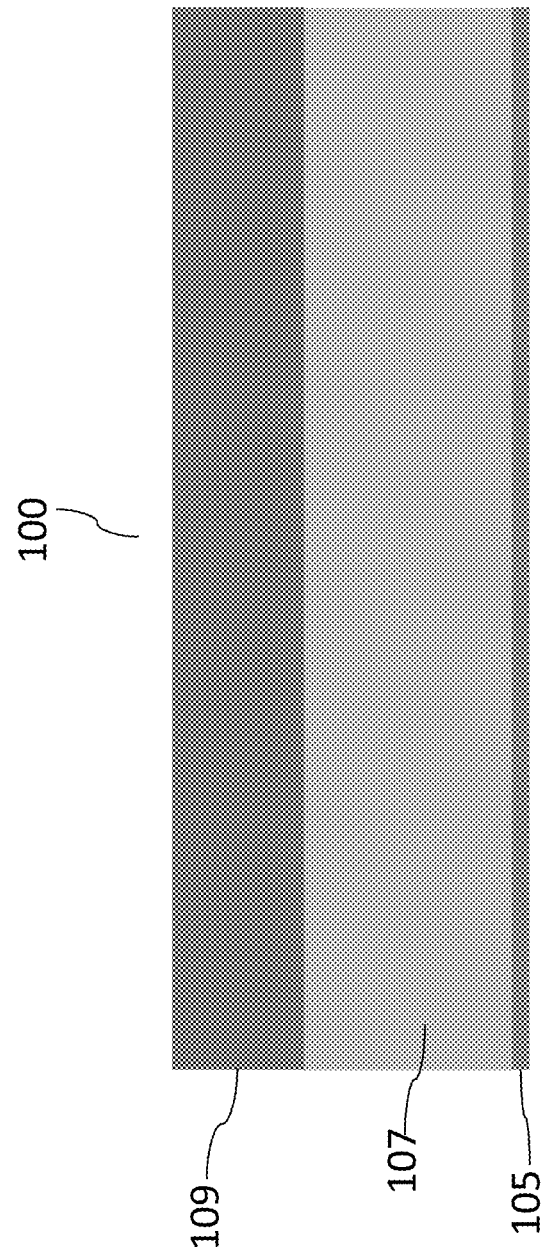
Figure 47:
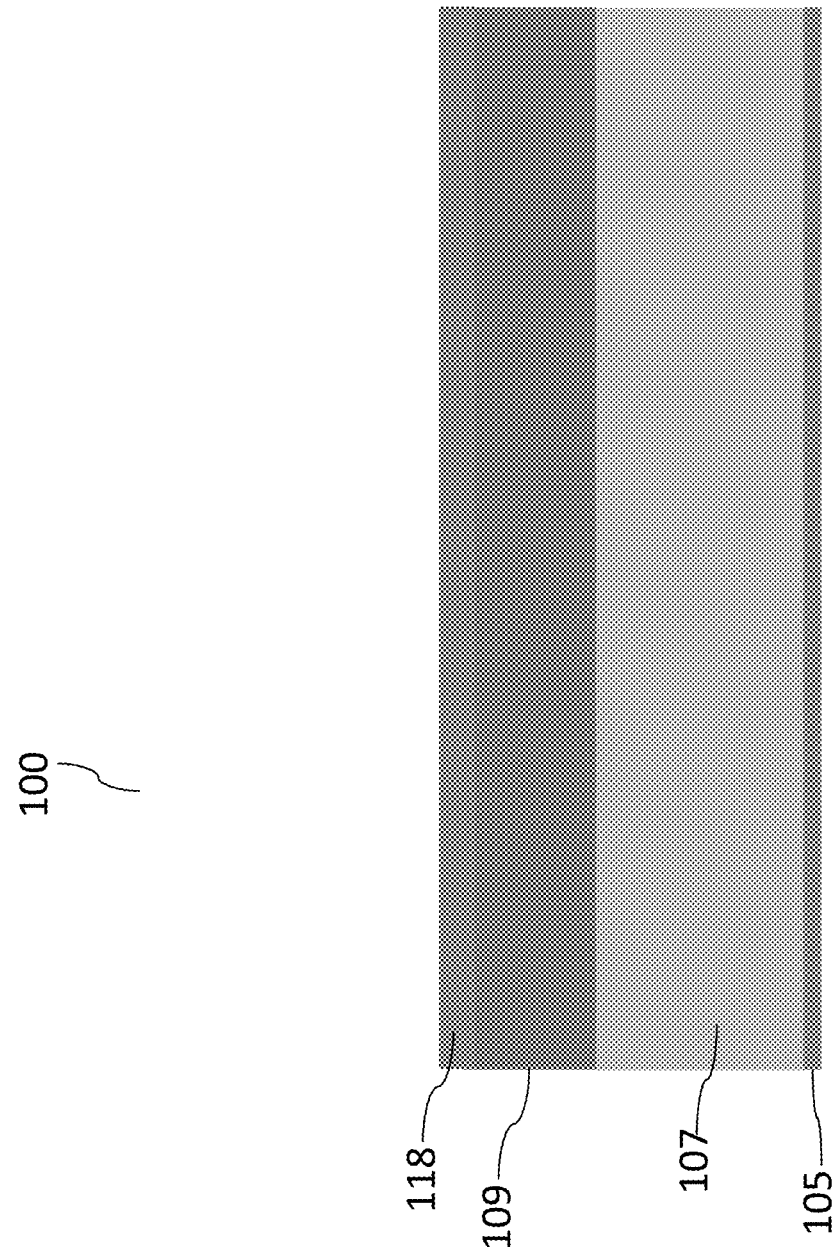
Figure 48:
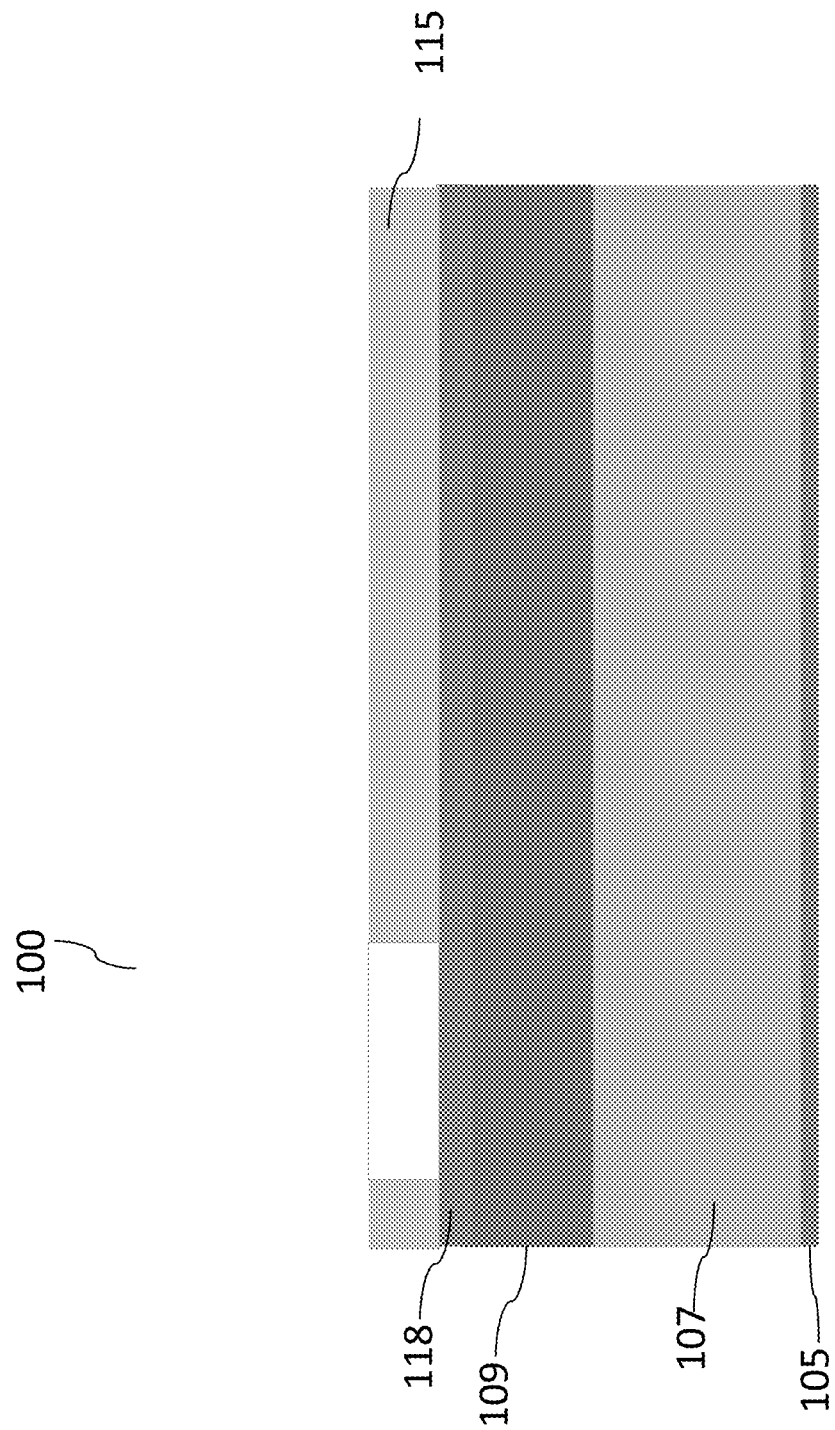
Figure 49:
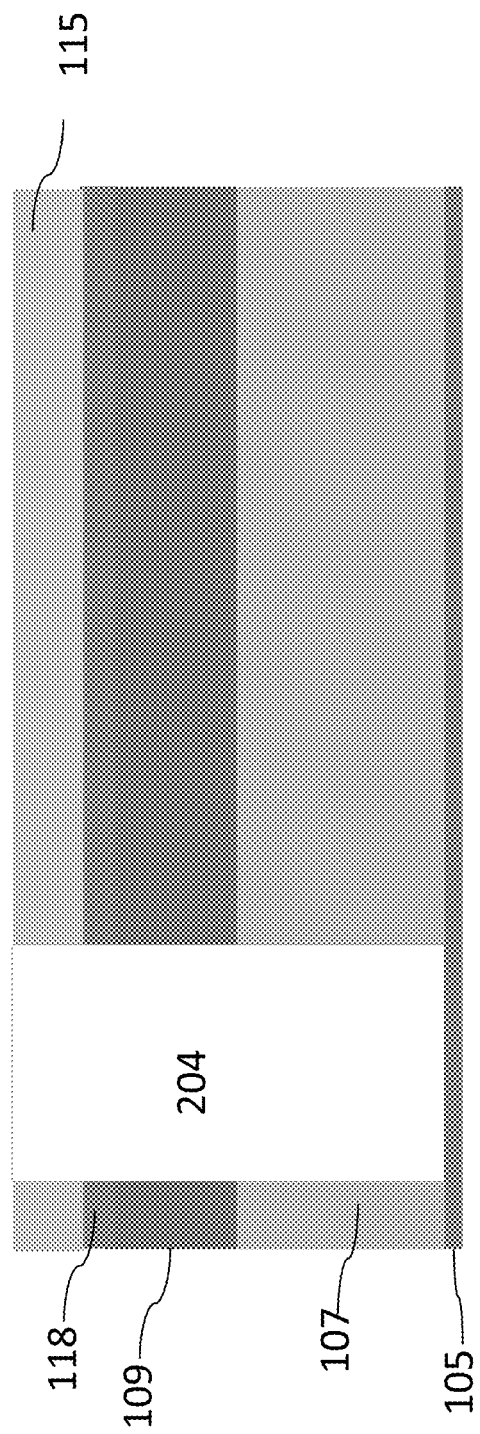
Figure 50:
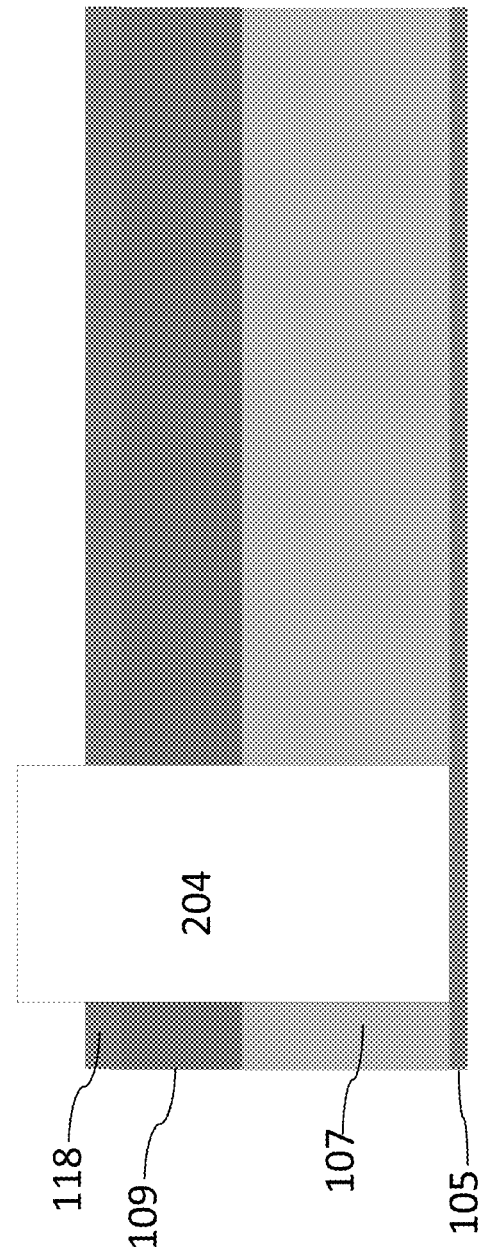

FIG. 46 has the wafer 100, with a thick silicon carbide layer 109, similar to the one in FIG. 2. A hardmask layer 118 is applied on to this surface as in FIG. 47. Referring now to FIG. 48, resist material 115 is spun on with an inlet pattern. The wafer is then subjected to a dry etch that stops at the buried oxide layer 105, to form inlets 204, as shown in FIG. 49. In FIG. 50, the resist 115 is stripped and the wafer cleaned.

Figure 51:
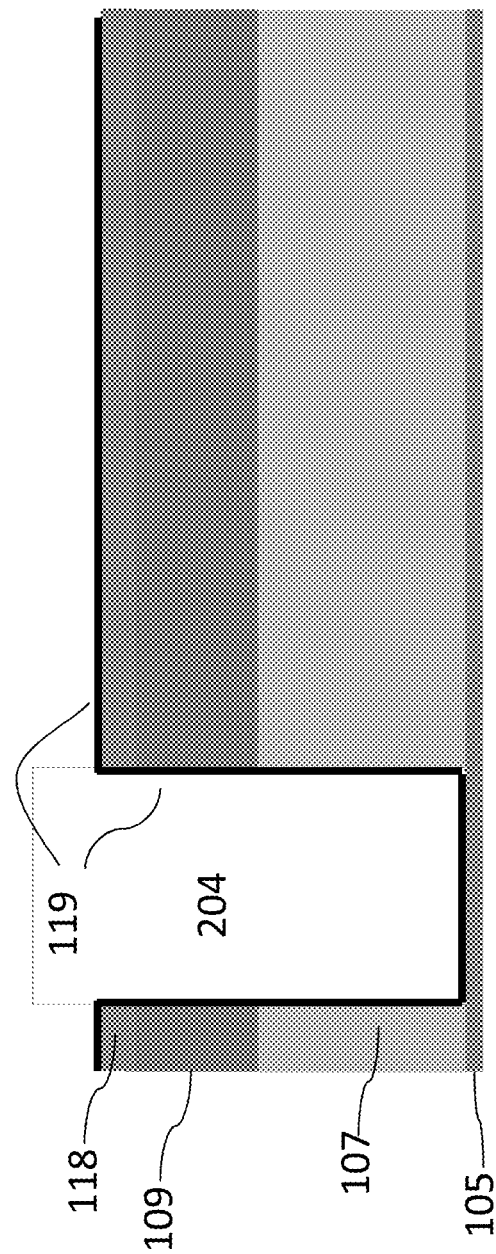
Figure 52:
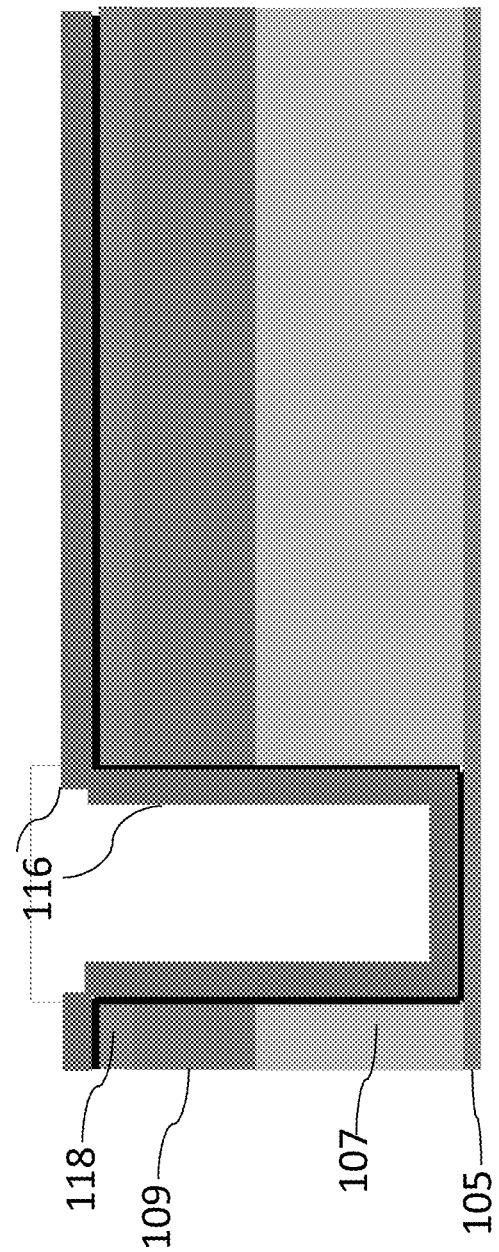
Figure 53:
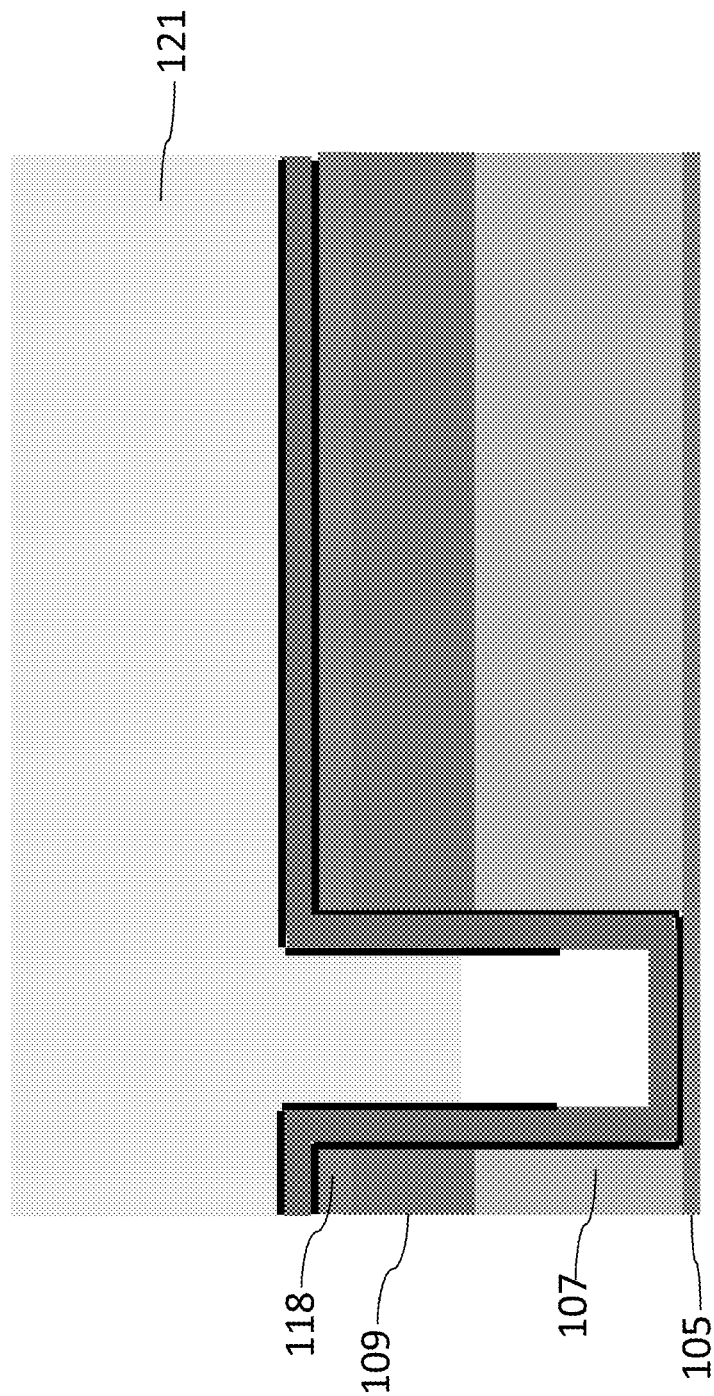
Figure 54:
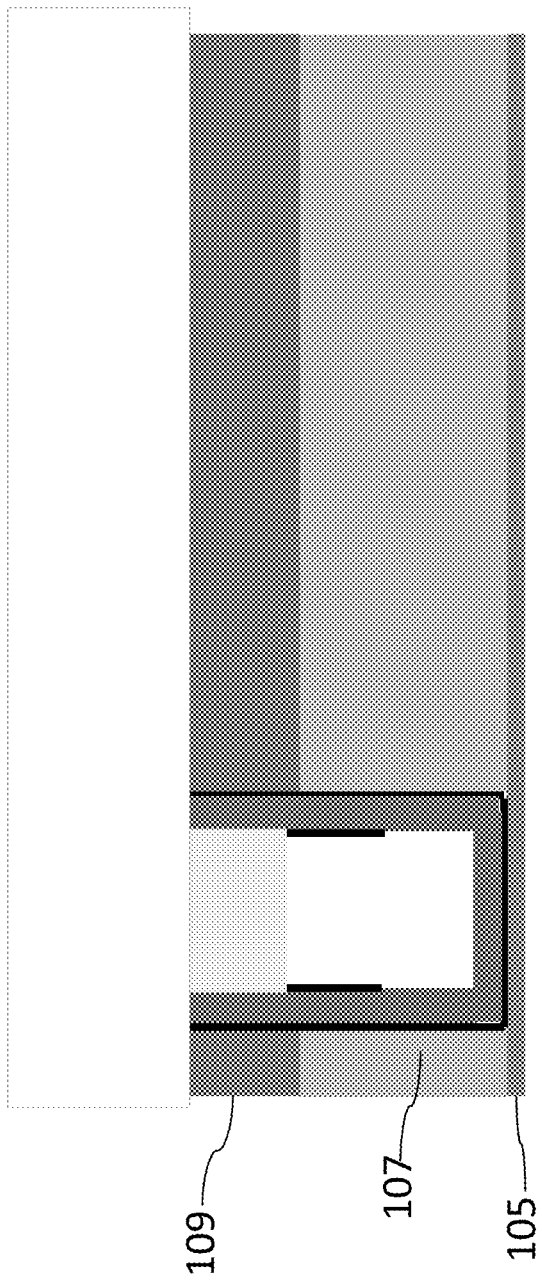

Referring now to FIG. 51, as in FIG. 10, a thin bio-robust material layer 119 is deposited. In certain embodiments, this could be ALD TaO. An additional sacrificial protection film 116, can be added as shown in FIG. 52. This structure is then coated with a film 121, with enough conformality to plug the inlets as shown in FIG. 53. In some embodiments, this layer can be TiN/W or silicon oxide deposited with Ozone and Tetraethylorthosilicate precursors. This structure is then subjected to CMP to remove all the over layers, stopping on layer 109 as shown in FIG. 54.

Figure 55:
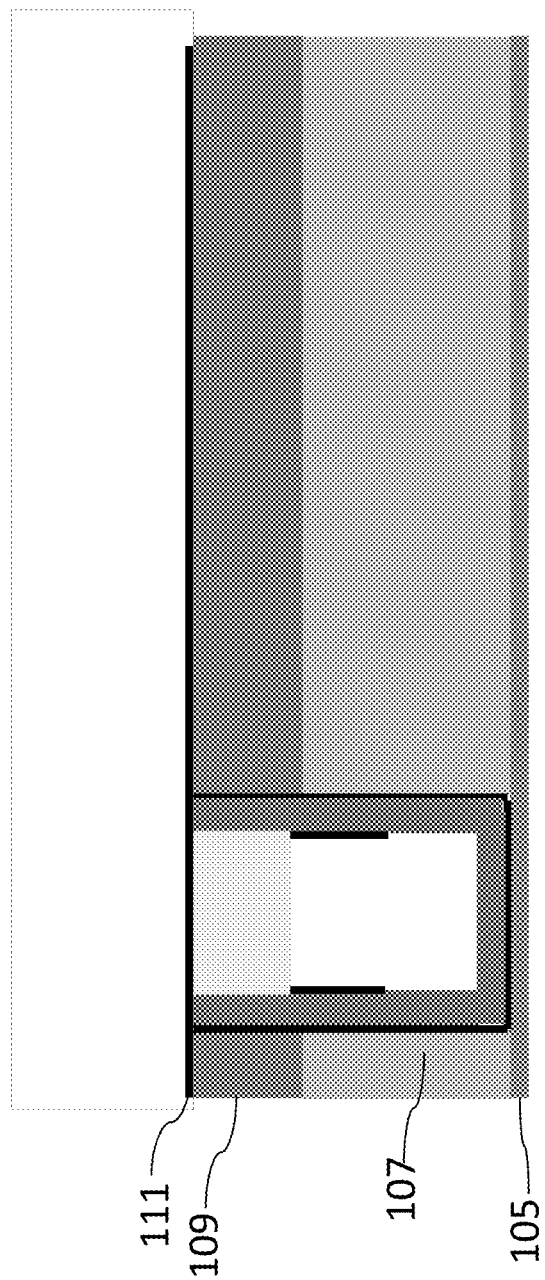
Figure 56:
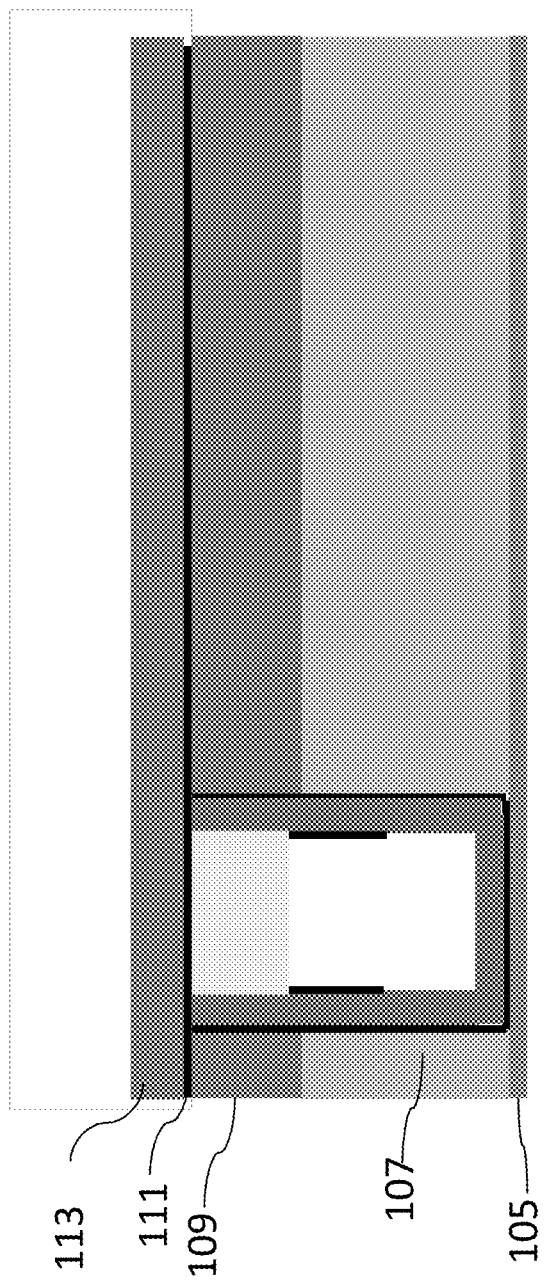
Figure 57:
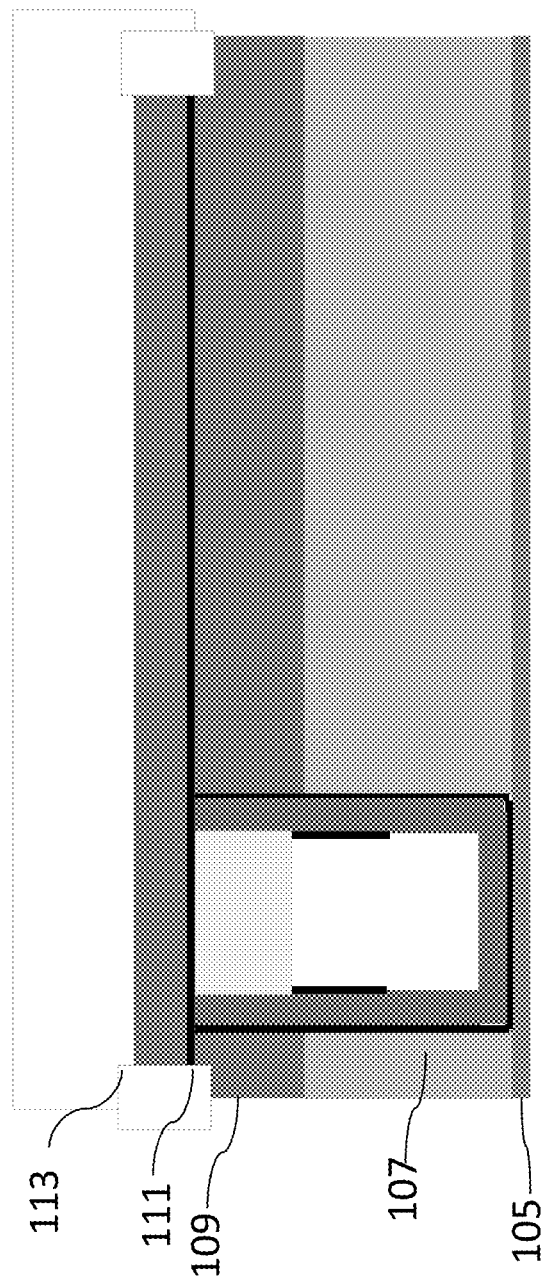

Referring now to FIG. 55, a thin sacrificial material is deposited as layer 111, which can be sputtered tungsten. A bio-robust liner layer, which is not susceptible to oxidation can also be deposited below and above this layer if needed. A thin silicon carbide layer 113 is deposited on this surface as shown in FIG. 56. This layer can then be patterned with the line mask and the structure etched back to below the level of nanochannel layer 111, into the etchstop layer 109, as show in FIG. 57. The remaining processing steps continue from process in FIG. 23 of the previously-described process.

In exemplary embodiments, it can be desirable to provide sealing of bio-robust materials so that the non-bio-robust materials are not exposed to bio-fluids. In specific embodiments, the bio-robust materials atomically seal to the non-bio-robust material that needs to be protected (without gaps for the bio-fluids to get through). In addition, the bio-robust layers seal to each other (e.g. sidewalls and top layers of channels). The bio-robust layer may also serve to adhere adjacent layers.

In particular embodiments, atomic layer deposition (ALD) may be used because the layers are extremely conformal to residual surface topography in underlying layers. Examples of materials suitable for ALD include, but are not limited, to: $Al_2O_3$, $Ta_2O_5$, $HfO_2$, $HfSiO_2$, $ZrO_2$, $AlSiO_2$, TiN, Ti, TiAlN, AlN, HfN, TaN, TaCN, HfSiN, TiO. A table of additional materials that may be used for ALD is provided below.

| Compound class | Examples |
| --- | --- |
| II-VI compounds | ZnS, ZnSe, ZnTe, $ZnS_{1-x}Se_x$, CaS, SrS, BaS, $SrS_{1-x}Se_x$, CdS, CdTe, MnTe, HgTe, $Hg_{1-x}Cd_xTe$, $Cd_{1-x}Mn_xTe$ |
| II-VI based thin-film electroluminescent (TFEL) phosphors | ZnS:M (M = Mn, Tb, Tm), CaS:M (M = Eu, Ce, Tb, Pb), SrS:M (M = Ce, Tb, Pb, Mn, Cu) |
| III-V compounds | GaAs, AlAs, AlP, InP, GaP, InAs, $Al_xGa_{1-x}As$, $Ga_xIn_{1-x}As$, $Ga_xIn_{1-x}P$ |
| Semiconductors/dielectric nitrides | AlN, GaN, InN, $SiN_x$ |
| Metallic nitrides | TiN, TaN, $Ta_3N_5$, NbN, MoN |
| Dielectric oxides | $Al_2O_3$, $TiO_2$, $ZrO_2$, $HfO_2$, $Ta_2O_5$, $Nb_2O_5$, $Y_2O_3$, $MgO,CeO_2$, $SiO_2$, $La_2O_3$, $SrTiO_3$, $BaTiO_3$ |
| Transparent conductor oxides | $In_2O_3$, $In_2O_3$:Sn, $In_2O_3$:F, $In_2O_3$:Zr, $SnO_2$, $SnO_2$:Sb, ZnO, |
| Semiconductor oxides | ZnO:Al, $Ga_2O_3$, MO, $CoO_x$ |
| Superconductor oxides | $YBa_2Cu_3O_{7-x}$ |
| Fluorides | $CaF_2$, $SrF_2$, $ZnF_2$ |

Bio-robust materials may be deposited using only ALD, only CVD, or a combination of ALD and CVD. Additionally, the ALD and CVD materials can be deposited by thermally activated as well as by plasma or UV activated processes. In certain embodiments, the ALD layer can be a single layer or a multi-layer. In case of multi layers, one or more of these can be sacrificial liners that are etched away during the processing of the device leaving behind an underlayer that can still be protective in nature.

Additionally, bio-robust materials may be deposited by sublimation, as in the case of Parylene in its various forms.

While silicon nitride has been provided as an example of one non-bio-robust material, other materials include metals such as tungsten, copper, titanium, gold, platinum, ruthenium, aluminum, silver and other, as well as dielectrics. A partial list of dielectrics includes silicon and compounds of silicon such as oxides, nitrides, carbides, oxy nitrides, carbo-nitrides and oxy-carbides. Methyl silsequioxanes, hydrogen silsequioxanes and other organic silicates can be appropriately used. In addition plastics and polymeric materials such as PolyMethylMethAcrylate (PMMA), PolyCarbonate, PolyPropylene, Teflon and SU-8 can be used.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

[1] Santen, R. J., Yue, W., Naftolin, F., Mor, G., Berstein, L. The potential of aromatase inhibitors in breast cancer prevention. *Endocrine-Related Cancer.* 6, 235-243 (1999).

[2] Goss, P. E., Strasser, K. Aromatase Inhibitors in the Treatment and Prevention of Breast Cancer. *J. Clin. Oncol.* 19, 881-894 (2001).

[3] Chlebowski, R. T. Reducing the Risk of Breast Cancer. *N. Engl. J. Med.,* 343, 191-198 (2000).

[4] Dowsett, M., Jones, A., Johnston, S. R., Jacobs, S., Trunet, P., Smith, I. E. In vivo measurement of aromatase inhibition by letrozole (CGS 20267) in postmenopausal patients with breast cancer. *Clin. Cancer Res.* 1, 1511-1515 (1995).

[5] Brueggemeier, R. W., Hackett, J. C., Diaz-Cruz, E. S. Aromatase Inhibitors in the Treatment of Breast Cancer. *Endocrine Reviews* 26, 331-345 (2005).

[6] Coates, A. S., Keshaviah, A., Thürlimann, B., et al. Five years of letrozole compared with tamoxifen as initial adjuvant therapy for postmenopausal women with endocrine-responsive early breast cancer: update of study BIG 1-98. *J. Clin. Oncol.* 25, 486-492 (2007).

[7] Goss, P. E., Ingle, J. N., Martino, S., et al. A randomized trial of letrozole in postmenopausal women after five years of tamoxifen therapy for early-stage breast cancer. *N. Engl. J. Med.* 349, 1793-1802 (2003).

[8] Garreau, J. R., Delamelena, T., Walts, D., Karamlou, K., Johnson, N. Side effects of aromatase inhibitors versus tamoxifen: the patients' perspective. *Am. J. Surg.* 192, 496-8 (2006).

[9] Luthra, R., Kirma, N., Jones, J., Tekmal, R. R. Use of letrozole as a chemopreventive agent in aromatase over-expressing transgenic mice. *The Journal of Steroid Biochemistry and Molecular Biology.* 86, 461-467 (2003).

[10] Harper-Wynne, C., Ross, G., Sacks, N., Salter, J., Nasiri, N., Iqbal, J., A'Hern, R., Dowsett, M. Effects of the aromatase inhibitor letrozole on normal breast epithelial cell proliferation and metabolic indices in postmenopausal women: a pilot study for breast cancer prevention. *Cancer Epidemiol. Biomarkers Prev.* 11,614-21 (2002).

[11] J. Maloney, S. Lipka and S. Baldwin, In Vivo Biostability of CVD Silicon Oxide and Silicon Nitride Films, *Mater. Res. Soc. Symp. Proc. Vol.* 872 (2005)

[12] H Hammerle, K. Kobuch, K. Kohler, W. Nisch, H. Sachs, M. Stelzle, *Biomaterials,* 23, p 797-804 (2002)

The invention claimed is:

1. A nanochannel delivery device comprising:
an inlet microchannel comprising a first sidewall;
an outlet microchannel comprising a second sidewall; and
a nanochannel etched between a first bio-robust layer and a second bio-robust layer, wherein:
 the first bio-robust layer is a silicon carbide layer;
 the second bio-robust layer is a silicon carbide layer;
 the etched nanochannel is in fluid communication with the inlet microchannel and the outlet microchannel;
 the inlet microchannel comprises a first bio-robust coating on the first sidewall of the inlet microchannel, wherein the first bio-robust coating is a tantalum oxide coating;
 the outlet microchannel comprises a second bio-robust coating on the second sidewall of the outlet microchannel, wherein the second bio-robust coating is a silicon carbide coating; and
 the first bio-robust coating is atomically sealed to the first bio-robust layer; and
 the second bio-robust coating is atomically sealed to the second bio-robust layer.

2. The nanochannel delivery device of claim 1 wherein the inlet microchannel comprises the first bio-robust coating atomically sealed to a non-bio-robust material.

3. The nanochannel delivery device of claim 1 wherein the outlet microchannel comprises the second bio-robust coating atomically sealed to a non-bio-robust material.

4. The nanochannel delivery device of claim 1 wherein:
the first bio-robust coating is atomically sealed to the second bio-robust layer; and
the second bio-robust coating is atomically sealed to the first bio-robust layer.

5. The nanochannel delivery device of claim 1 wherein the nanochannel is in direct fluid communication with the inlet microchannel and the outlet microchannel.

6. The nanochannel delivery device of claim 1 wherein the height of the etched nanochannel is less than 200 nm.

* * * * *